US008697885B2

(12) United States Patent
Kawakami et al.

(10) Patent No.: US 8,697,885 B2
(45) Date of Patent: Apr. 15, 2014

(54) CARBAZOLE COMPOUND, LIGHT-EMITTING ELEMENT MATERIAL, ORGANIC SEMICONDUCTOR MATERIAL, LIGHT-EMITTING ELEMENT, LIGHT EMITTING DEVICE, LIGHTING DEVICE, AND ELECTRONIC DEVICE

(75) Inventors: Sachiko Kawakami, Kanagawa (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 194 days.

(21) Appl. No.: 13/305,081

(22) Filed: Nov. 28, 2011

(65) Prior Publication Data

US 2012/0133274 A1 May 31, 2012

(30) Foreign Application Priority Data

Nov. 30, 2010 (JP) .................................. 2010-267060

(51) Int. Cl.
C07D 235/04 (2006.01)
B32B 9/00 (2006.01)
H01J 1/62 (2006.01)

(52) U.S. Cl.
USPC .................. 548/305.1; 548/302.7; 548/304.4; 428/690; 428/917; 313/504; 313/506; 315/169.3

(58) Field of Classification Search
USPC ......... 548/302.7, 304.4, 305.1; 428/690, 917; 313/504, 506; 315/169.3
See application file for complete search history.

(56) References Cited

U.S. PATENT DOCUMENTS

| | | | |
|---|---|---|---|
| 5,061,569 A | 10/1991 | Vanslyke et al. | |
| 7,838,128 B2 * | 11/2010 | Kawakami et al. | 428/690 |
| 7,897,964 B2 | 3/2011 | Kawakami et al. | |
| 7,901,791 B2 * | 3/2011 | Nakashima et al. | 428/690 |
| 7,989,644 B2 | 8/2011 | Tanabe et al. | |
| 8,093,399 B2 * | 1/2012 | Nomura et al. | 548/224 |
| 2003/0129448 A1 | 7/2003 | Lin et al. | |
| 2004/0151943 A1 | 8/2004 | Lee et al. | |
| 2004/0161633 A1 | 8/2004 | Seo et al. | |
| 2005/0067951 A1 | 3/2005 | Richter et al. | |
| 2005/0221124 A1 | 10/2005 | Hwang et al. | |
| 2006/0073357 A1 | 4/2006 | Brunner et al. | |
| 2007/0145888 A1 | 6/2007 | Yabunouchi et al. | |
| 2007/0231503 A1 | 10/2007 | Hwang et al. | |
| 2008/0014464 A1 | 1/2008 | Kawamura et al. | |
| 2008/0124572 A1 | 5/2008 | Mizuki et al. | |
| 2008/0268282 A1 | 10/2008 | Spindler et al. | |
| 2008/0284328 A1 | 11/2008 | Nakashima et al. | |
| 2009/0015140 A1 | 1/2009 | Kawakami et al. | |
| 2009/0058261 A1 | 3/2009 | Kawakami et al. | |
| 2009/0131673 A1 | 5/2009 | Tanabe et al. | |
| 2009/0160323 A1 | 6/2009 | Nomura et al. | |
| 2010/0069647 A1 | 3/2010 | Suzuki et al. | |
| 2010/0133519 A1 | 6/2010 | Chen et al. | |
| 2010/0244008 A1 | 9/2010 | Lee et al. | |
| 2010/0244672 A1 | 9/2010 | Nomura et al. | |
| 2011/0006670 A1 | 1/2011 | Katakura et al. | |
| 2011/0042654 A1 | 2/2011 | Jung et al. | |
| 2011/0127495 A1 | 6/2011 | Hong et al. | |
| 2011/0147728 A1 | 6/2011 | Kawakami et al. | |
| 2011/0248217 A1 | 10/2011 | Tanabe et al. | |
| 2011/0297924 A1 | 12/2011 | Yabunouchi et al. | |
| 2012/0074390 A1 | 3/2012 | Seo et al. | |

FOREIGN PATENT DOCUMENTS

| | | |
|---|---|---|
| EP | 1 862 524 A1 | 12/2007 |
| EP | 1 950 194 A1 | 7/2008 |
| JP | 62-280850 | 12/1987 |
| JP | 63-14156 | 1/1988 |
| JP | 9-310066 | 12/1997 |
| JP | 3210481 | 7/2001 |
| JP | 2002-241352 | 8/2002 |
| JP | 2003-89682 | 3/2003 |
| JP | 2004-103467 | 4/2004 |
| JP | 2004-178896 | 6/2004 |
| JP | 2007-15933 | 1/2007 |
| JP | 2007-110093 | 4/2007 |
| JP | 2007-520470 | 7/2007 |
| JP | 2008-21687 | 1/2008 |
| JP | 2008-545729 | 12/2008 |
| JP | 2009-155300 | 7/2009 |
| JP | 2009-158848 | 7/2009 |
| JP | 2009-267255 | 11/2009 |
| KR | 10-2008-0018218 | 2/2008 |

(Continued)

OTHER PUBLICATIONS

Nomura, R. et al, "Synthesis of Metal-Carbene Containing Polymers by Polycondensation of a Bifunctional Alkoxycarbene with Diamines," Macromolecules, American Chemical Society, vol. 33, No. 6, Mar. 1, 2000, pp. 1936-1939.
Goldsmith et al., "C-H Bond Activation by a Ferric Methoxide Complex: Modeling the Rate-Determining Step in the Mechanism of Lipoxygenase," J. Am. Chem. Soc., 2002, vol. 124, No. 1, pp. 83-96
Ohnishi et al., "A Method of Measuring an Energy Level High Molecular E1 Materials—Development of Light-Emitting High Molecular Compounds," Kyoritsu Shuppan, Dec. 25, 2004, pp. 64-67 (English translation).
Ho et al., "P-131: Novel Deep Blue Dopants for Organic Light Emitting Devices," SID Digest '05, May 24, 2005, vol. 36, pp. 802-805.
Promarak et al., "Synthesis and Properties of Stable Amorphous Hole-Transporting Molecules for Electroluminescent Devices," *Tetrahedron Letters*, 2006, vol. 47, No. 50, pp. 8949-8952.

(Continued)

Primary Examiner — Golam M M Shameem
(74) Attorney, Agent, or Firm — Husch Blackwell LLP

(57) ABSTRACT

An object is to provide a novel carbazole compound that can be used for a transport layer, a host material, or a light-emitting material in a light-emitting element. A carbazole compound where nitrogen of a carbazole group, the carbazole skeleton of which whose 3-position is bonded to the 4-position of a dibenzofuran skeleton or a dibenzothiophene skeleton, is bonded to a benzimidazole skeleton through a phenylene group, is provided. The carbazole compound has a high carrier-transport property, and can be suitably used for a material for a light-emitting element or for an organic semiconductor material.

20 Claims, 18 Drawing Sheets

(56) References Cited

FOREIGN PATENT DOCUMENTS

| | | |
|---|---|---|
| WO | WO 2005/090512 A1 | 9/2005 |
| WO | WO 2006/128800 A1 | 12/2006 |
| WO | WO 2007/013537 A1 | 2/2007 |
| WO | WO 2007/043354 A1 | 4/2007 |
| WO | WO 2007/148660 A1 | 12/2007 |
| WO | WO 2008/062636 A1 | 5/2008 |
| WO | WO 2008/069756 A1 | 6/2008 |
| WO | WO 2009/035296 A2 | 3/2009 |
| WO | WO 2009/061145 A1 | 5/2009 |
| WO | WO 2009/061156 A1 | 5/2009 |
| WO | WO 2011/004639 A1 | 1/2011 |
| WO | WO 2011/052250 A1 | 5/2011 |

OTHER PUBLICATIONS

Shen et al., "Ambipolar Conductive 2,7-Carbazole Derivatives for Electroluminescent Devices," *Adv. Funct. Mater.*, 2007, vol. 17, No. 6, pp. 983-995.

Ho et al., "P-131: Novel Deep Blue Dopants for Organic Light Emitting Devices," *Sid 05 Digest '05*, May 24, 2005, vol. 36, pp. 802-805.

Promarak et al., "Synthesis and Properties of Stable Amorphous Hole-Transporting Molecules for Electroluminescent Devices," *Tetrahedron Letters*, 2006, vol. 47, pp. 8949-8952.

Shen et al., "Arnbipolar Conductive 2,7-Carbazole Derivatives for Electroluminescent Devices," *Adv. Funct. Mater.*, 2007, vol. 17, pp. 983-995.

* cited by examiner

CARBAZOLE COMPOUND, LIGHT-EMITTING ELEMENT MATERIAL, ORGANIC SEMICONDUCTOR MATERIAL, LIGHT-EMITTING ELEMENT, LIGHT EMITTING DEVICE, LIGHTING DEVICE, AND ELECTRONIC DEVICE

BACKGROUND OF THE INVENTION

1. Field of the Invention

The present invention relates to a carbazole compound that can be used for a light-emitting element material. The present invention further relates to a light-emitting element material, an organic semiconductor material, and a light-emitting element each using the carbazole compound.

2. Description of the Related Art

As next generation lighting devices or display devices, display devices using light-emitting elements (organic EL elements) in which organic compounds are used as light-emitting substances have been developed at an accelerated pace because of their advantages of thinness, lightweightness, high speed response to input signals, low power consumption, etc.

In an organic EL element, voltage application between electrodes, between which a light-emitting layer is interposed, causes recombination of electrons and holes injected from the electrodes, which brings a light-emitting substance into an excited state, and the return from the excited state to the ground state is accompanied by light emission. Since the wavelength of light emitted from a light-emitting substance is peculiar to the light-emitting substance, use of different types of organic compounds as light-emitting substances makes it possible to obtain light-emitting elements which exhibit various wavelengths, i.e., various colors.

In the case of display devices which are expected to display images, such as displays, at least three-color light, i.e., red light, green light, and blue light is necessary for reproduction of full-color images. Further, in application to lighting devices, light having wavelength components uniformly in the visible light region is ideal for obtaining a high color rendering property, but in reality, light obtained by mixing two or more kinds of light having different wavelengths is used for lighting application in many cases. It is known that, with a mixture of three-color light, i.e., red light, green light, and blue light, white light having a high color rendering property can be obtained.

Light emitted from a light-emitting substance is peculiar to the substance, as described above. However, important performances as a light-emitting, element, such as lifetime, power consumption, and even emission efficiency, are not only dependent on a light-emitting substance but also greatly dependent on layers other than a light-emitting layer, an element structure, properties of an emission center substance and a host material, compatibility between them, carrier balance, or the like. Therefore, it is true that many kinds of light-emitting element materials are necessary for the growth of this field. For the above-described reasons, light-emitting element materials with a variety of molecular structures have been proposed (e.g., see Patent Document 1).

As is generally known, the generation ratio of a singlet excited state to a triplet excited state in a light-emitting element using electroluminescence is 1:3. Therefore, a light-emitting element in which a phosphorescent material capable of converting the triplet excited state to light emission is used as an emission center substance can theoretically realize higher emission efficiency than a light-emitting element in which a fluorescent material capable of converting the singlet excited state to light emission is used as an emission center substance.

However, since the triplet excited state of a substance is at a lower energy level than the singlet excited state of the substance, a substance that emits phosphorescence has a larger band gap than a substance that emits fluorescence when the emissions are at the same wavelength.

As a substance serving as a host material in a host-guest type light-emitting layer or a substance contained in each transport layer in contact with a light-emitting layer, a substance having a larger band gap or higher triplet excitation energy (energy difference between a triplet excited state and a singlet ground state) than an emission center substance is used for efficient conversion of excitation energy to light emission from the emission center substance.

Therefore, a host material and a carrier-transport material each having a further larger band gap or higher triplet excitation energy are necessary in order that fluorescence at a shorter wavelength than blue fluorescence or phosphorescence at a shorter wavelength than green phosphorescence be efficiently obtained. There are however not many variations of materials that have a sufficiently large band gap or high triplet excitation energy in addition to good characteristics as a light-emitting element material, and as described above, the performance of a light-emitting element depends also on the compatibility between substances. In consideration of the above, it is difficult to say that there are sufficient variations of materials with which light-emitting elements having good characteristics can be manufactured.

REFERENCE

Patent Document 1: Japanese Published Patent Application No. 2007-15933

SUMMARY OF THE INVENTION

Therefore, an object of one embodiment of the present invention is to provide a novel carbazole compound that can be used for a transport layer, a host material, or a light-emitting material in a light-emitting element.

Another object of one embodiment of the present invention is to provide a light-emitting element material using the above novel carbazole compound.

Another object of one embodiment of the present invention is to provide an organic semiconductor material using the above novel carbazole compound.

Another object of one embodiment of the present invention is to provide a light-emitting element having high emission efficiency.

Another object of one embodiment of the present invention is to provide a light-emitting device, a lighting device, or an electronic device having low power consumption. Note that in one embodiment of the present invention, it is only necessary that at least one of the above-described objects should be achieved.

The present inventors have been able to synthesize a carbazole compound where nitrogen of a carbazole group, the carbazole skeleton of which whose 3-position is bonded to the 4-position of a dibenzofuran skeleton or a dibenzothiophene skeleton, is bonded to a benzimidazole skeleton through a phenylene group. Further, the inventors have found out that the carbazole derivative has a high carrier-transport property and can be suitably used for a material of a light-emitting element or for an organic semiconductor material.

In other words, one embodiment of the present invention is a carbazole compound where nitrogen of a carbazole group, the carbazole skeleton of which whose 3-position is bonded to the 4-position of a dibenzofuran skeleton or a dibenzothiophene skeleton, is bonded to a benzimidazole skeleton through a phenylene group. Further, nitrogen at the 1-position of the benzimidazole skeleton has an aryl group having 6 to 12 carbon atoms.

Note that in the above carbazole compound, carbon in the benzimidazole skeleton and carbon in the dibenzofuran skeleton or in the dibenzothiophene skeleton may separately have a substituent. When the benzimidazole skeleton has a substituent, the substituent can be either an alkyl group having 1 to 4 carbon atoms or a phenyl group. When the dibenzofuran skeleton or the dibenzothiophene skeleton has a substituent, the substituent can be either an alkyl group having 1 to 4 carbon atoms or an aryl group having 6 to 12 carbon atoms.

Further, the carbazole skeleton in the above carbazole compound may have a substituent at the 6-position, and the substituent can be selected from an alkyl group having 1 to 4 carbon atoms and an aryl group having 6 to 12 carbon atoms.

The carbazole compound with such a structure has a high carrier-transport property and can be suitably used for a host material or a carrier-transport layer in a light-emitting element. Owing to the high carrier-transport property of the carbazole compound, a light-emitting element having low driving voltage can be fabricated.

Further, the carbazole compound has a wide band gap, and therefore can be suitably used for a host material, into which an emission center substance that emits blue fluorescence and fluorescence at a longer wavelength than blue or an emission center substance that emits green phosphorescence and phosphorescence at a longer wavelength than green is dispersed. Since the carbazole compound has a wide band gap and thus high triplet excitation energy, the energy of carriers that are recombined in the host material can be effectively transferred to the emission center substance. Accordingly, a light-emitting element with high emission efficiency can be fabricated.

Also for a carrier-transport layer adjacent to a light-emitting layer containing an emission center substance that emits blue fluorescence or an emission center substance that emits green phosphorescence, the carbazole compound having a wide band gap can be suitably used without deactivating excitation energy of the emission center substance. Accordingly, a light-emitting element with high emission efficiency can be fabricated.

The above-described carbazole compound will be more specifically described. One embodiment of the present invention is a carbazole compound represented by a general formula (G1) below.

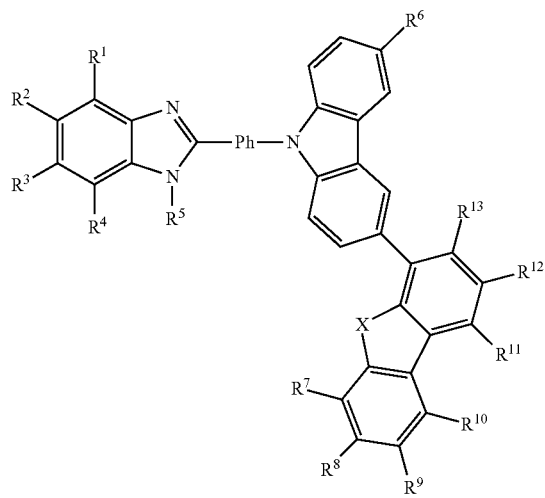

(G1)

In the formula, $R^1$ to $R^4$ separately represent any one of hydrogen, an alkyl group having 1 to 4 carbon atoms, a phenyl group, and a tolyl group, and $R^5$ represents an aryl group having 6 to 12 carbon atoms. Further, $R^6$ to $R^{13}$ separately represent any one of hydrogen, an alkyl group having 1 to 4 carbon atoms, and an aryl group having 6 to 12 carbon atoms. In addition, Ph represents a substituted or unsubstituted phenylene group; when the phenylene group has a substituent, the substituent can be an alkyl group having 1 to 4 carbon atoms. Furthermore, X represents a sulfur atom or an oxygen atom.

Another structure of the present invention is a carbazole compound represented by a general formula (G2) below.

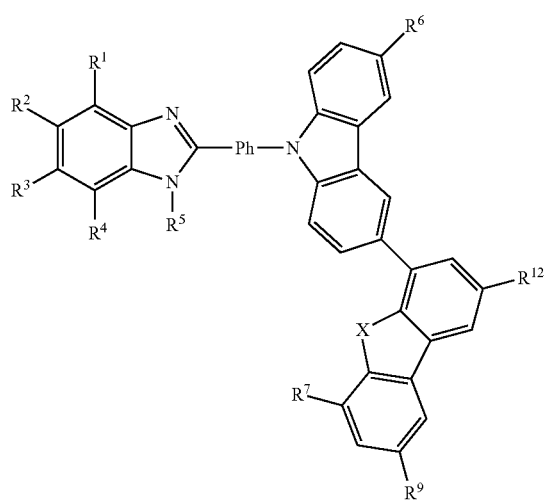

(G2)

In the formula, $R^1$ to $R^4$ separately represent any one of hydrogen, an alkyl group having 1 to 4 carbon atoms, a phenyl group, and a tolyl group, and $R^5$ represents an aryl group having 6 to 12 carbon atoms. Further, $R^6$, $R^7$, $R^9$, and $R^{12}$ separately represent any one of hydrogen, an alkyl group having 1 to 4 carbon atoms, and an aryl group having 6 to 12 carbon atoms. In addition, Ph represents a substituted or unsubstituted phenylene group; when the phenylene group has a substituent, the substituent can be an alkyl group having 1 to 4 carbon atoms. Furthermore, X represents a sulfur atom or an oxygen atom.

The carbazole compound can be synthesized easily.

Another structure of the present invention is a carbazole compound represented by a general formula (G3) below.

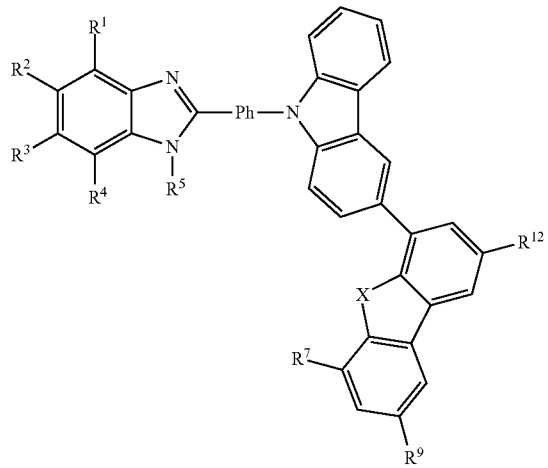

(G3)

In the formula, $R^1$ to $R^4$ separately represent any one of hydrogen, an alkyl group having 1 to 4 carbon atoms, a phenyl group, and a tolyl group, and $R^5$ represents an aryl group having 6 to 12 carbon atoms. Further, $R^7$, $R^9$, and $R^{12}$ separately represent any one of hydrogen, an alkyl group having 1 to 4 carbon atoms, and an aryl group having 6 to 12 carbon atoms. In addition, Ph represents a substituted or unsubstituted phenylene group; when the phenylene group has a substituent, the substituent can be an alkyl group having 1 to 4 carbon atoms. Furthermore, X represents a sulfur atom or an oxygen atom.

The carbazole compound is a carbazole derivative having a preferable structure because the evaporation rate tends to stabilize.

Another structure of the present invention is a carbazole compound represented by a general formula (G4) below.

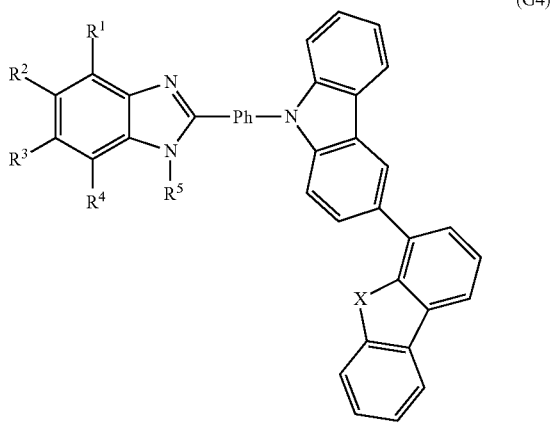

(G4)

In the formula, $R^1$ to $R^4$ separately represent any one of hydrogen, an alkyl group having 1 to 4 carbon atoms, a phenyl group, and a tolyl group, and $R^5$ represents an aryl group having 6 to 12 carbon atoms. In addition, Ph represents a substituted or unsubstituted phenylene group; when the phenylene group has a substituent, the substituent can be an alkyl group having 1 to 4 carbon atoms. Furthermore, X represents a sulfur atom or an oxygen atom.

The carbazole compound can be synthesized inexpensively because of the high availability of a material.

Another structure of the present invention is a carbazole compound represented by a general formula (G5) below.

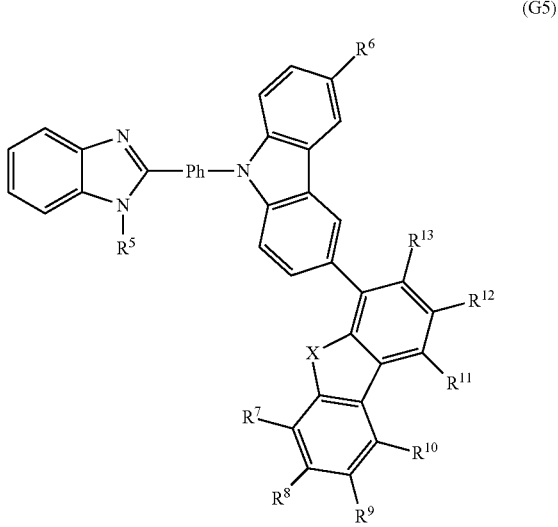

(G5)

In the formula, $R^5$ represents an aryl group having 6 to 12 carbon atoms. Further, $R^6$ to $R^{13}$ separately represent any one of hydrogen, an alkyl group having 1 to 4 carbon atoms, and an aryl group having 6 to 12 carbon atoms. In addition, Ph represents a substituted or unsubstituted phenylene group; when the phenylene group has a substituent, the substituent can be an alkyl group having 1 to 4 carbon atoms. Furthermore, X represents a sulfur atom or an oxygen atom.

The carbazole compound can be synthesized inexpensively because of the high availability of a material.

Another structure of the present invention is a carbazole compound represented by a general formula (G6) below.

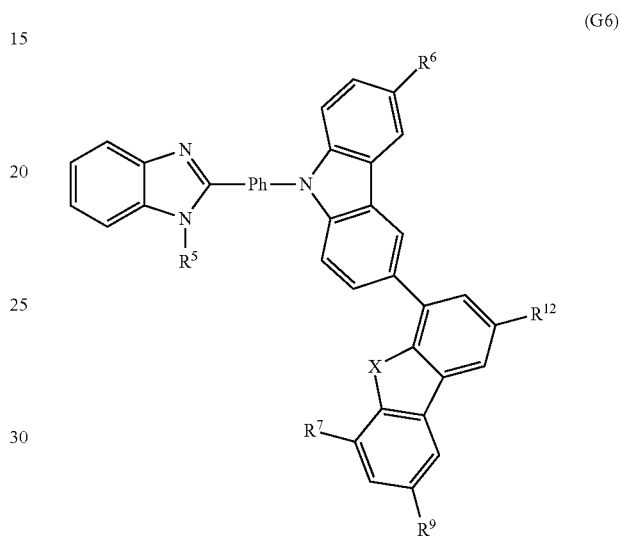

(G6)

In the formula, $R^5$ represents an aryl group having 6 to 12 carbon atoms. Further, $R^6$, $R^7$, $R^9$, and $R^{12}$ separately represent any one of hydrogen, an alkyl group having 1 to 4 carbon atoms, and an aryl group having 6 to 12 carbon atoms. In addition, Ph represents a substituted or unsubstituted phenylene group; when the phenylene group has a substituent, the substituent can be an alkyl group having 1 to 4 carbon atoms. Furthermore, X represents a sulfur atom or an oxygen atom.

The carbazole compound can be synthesized easily.

Another structure of the present invention is a carbazole compound represented by a general formula (G7) below.

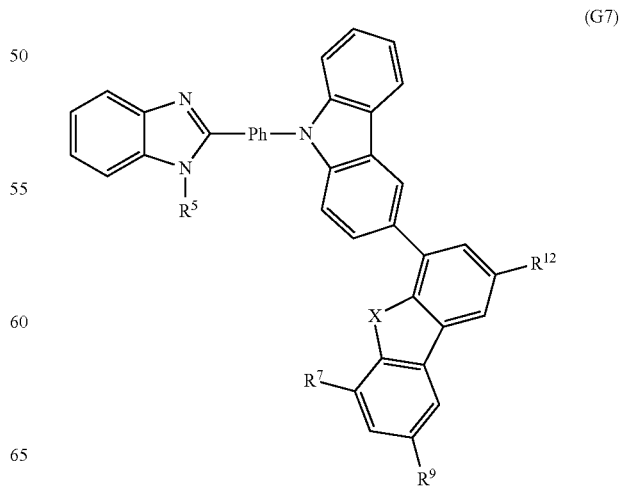

(G7)

In the formula, $R^5$ represents an aryl group having 6 to 12 carbon atoms. Further, $R^7$, $R^9$, and $R^{12}$ separately represent any one of hydrogen, an alkyl group having 1 to 4 carbon atoms, and an aryl group having 6 to 12 carbon atoms. In addition, Ph represents a substituted or unsubstituted phenylene group; when the phenylene group has a substituent, the substituent can be an alkyl group having 1 to 4 carbon atoms. Furthermore, X represents a sulfur atom or an oxygen atom.

The carbazole compound is a preferable evaporation material because the evaporation rate is extremely stable.

Another structure of the present invention is a carbazole compound represented by a general formula (G8) below.

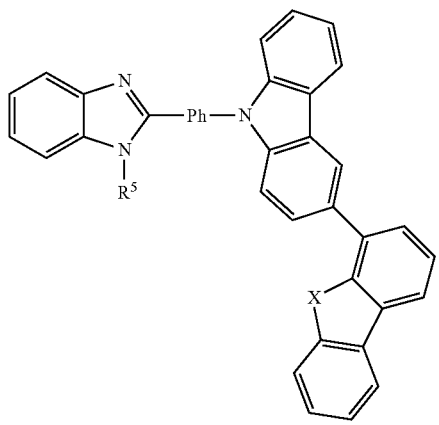

(G8)

In the formula, $R^5$ represents an aryl group having 6 to 12 carbon atoms. In addition, Ph represents a substituted or unsubstituted phenylene group; when the phenylene group has a substituent, the substituent can be an alkyl group having 1 to 4 carbon atoms. Furthermore, X represents a sulfur atom or an oxygen atom.

The structure of the carbazole compound can be synthesized inexpensively because of the high availability of a material.

Another structure of the present invention is a carbazole compound represented by a general formula (G9) below.

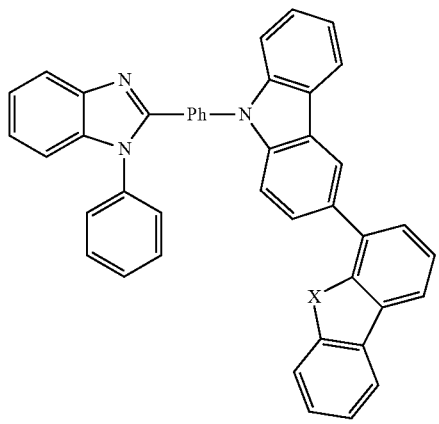

(G9)

In the formula, Ph represents a substituted or unsubstituted phenylene group; when the phenylene group has a substituent, the substituent can be an alkyl group having 1 to 4 carbon atoms. Further, in the formula, X represents a sulfur atom or an oxygen atom.

Another structure of the present invention is a carbazole compound represented by a general formula (G10) below.

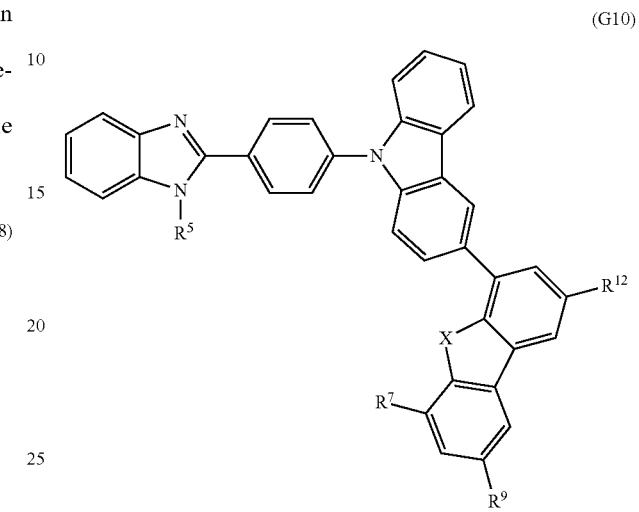

(G10)

In the formula, $R^5$ represents an aryl group having 6 to 12 carbon atoms. Further, $R^7$, $R^9$, and $R^{12}$ separately represent any one of hydrogen, an alkyl group having 1 to 4 carbon atoms, and an aryl group having 6 to 12 carbon atoms. Furthermore, X represents a sulfur atom or an oxygen atom.

The carbazole compound has a high carrier-transport property.

Another structure of the present invention is a carbazole compound represented by a general formula (G11) below.

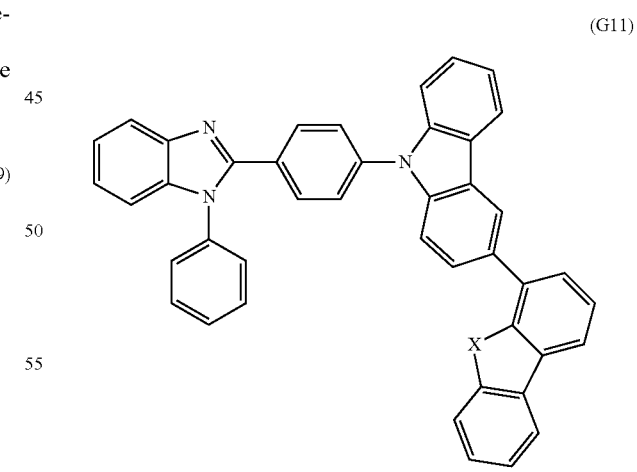

(G11)

In the formula, X represents a sulfur atom or an oxygen atom.

Another embodiment of the present invention is a carbazole compound represented by the following structural formula.

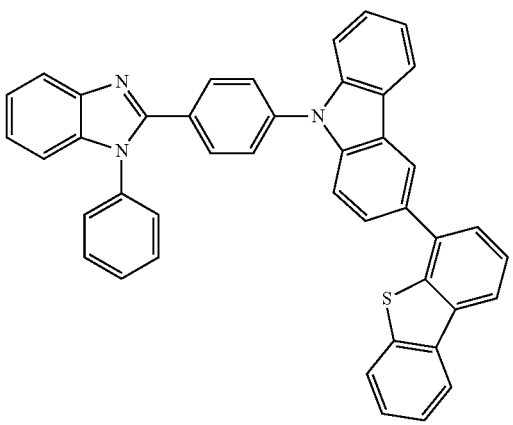 [SMILES: c1ccc(-n2c(-c3ccc(-n4c5ccccc5c5cc(-c6cccc7c6sc6ccccc67)ccc54)cc3)nc3ccccc32)cc1]

Another embodiment of the present invention is a carbazole compound represented by the following structural formula.

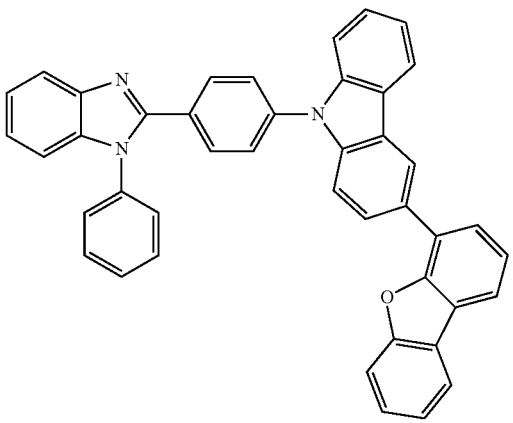 [SMILES: c1ccc(-n2c(-c3ccc(-n4c5ccccc5c5cc(-c6cccc7c6oc6ccccc67)ccc54)cc3)nc3ccccc32)cc1]

Another structure of the present invention is an organic semiconductor material containing any of the above carbazole compounds.

Another structure of the present invention is a light-emitting element including a layer containing an organic compound between a pair of electrodes, in which light emission is obtained from the layer containing an organic compound by voltage application between the electrodes and the layer containing an organic compound contains any of the above-described carbazole compounds.

Another structure of the present invention is a light-emitting device including the above light-emitting element and a means for controlling the light-emitting element.

Another embodiment of the present invention is an electronic device including the above light-emitting device.

Another structure of the present invention is a lighting device including the above light-emitting element.

A carbazole compound having any of the above-described structures is a substance having both an excellent carrier-transport property and a wide band gap, and can be suitably used for a material included in a transport layer or a host material or an emission center substance in a light-emitting layer for a light-emitting element. A light-emitting element using a light-emitting element material including the carbazole compound can be a light-emitting element having high emission efficiency. In addition, a light-emitting element using a light-emitting element material including the carbazole compound can be a light-emitting element having low voltage. Further, the carbazole compound can also be used for an organic semiconductor material.

DETAILED DESCRIPTION OF THE INVENTION

Figure 1A:
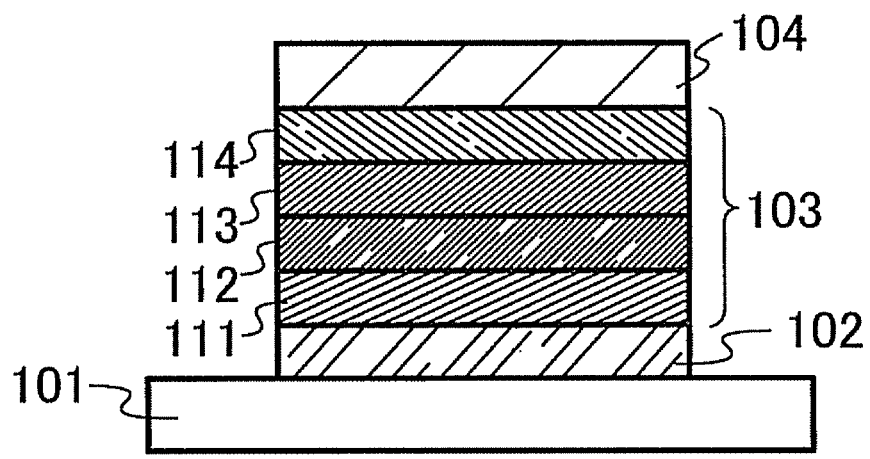
FIGS. 1A and 1B are conceptual diagrams of light-emitting elements.

Hereinafter, embodiments of the present invention are described. It is easily understood by those skilled in the art that modes and details disclosed herein can be modified in various ways without departing from the spirit and scope of the present invention. Therefore, the present invention is not construed as being limited to description of the embodiments.

Embodiment 1

Carbazole compounds in this embodiment each have a structure in which nitrogen of a carbazole group, the carbazole skeleton of which whose 3-position is bonded to the 4-position of a dibenzofuran skeleton or a dibenzothiophene skeleton, is bonded to a benzimidazole skeleton through a phenylene group. Note that nitrogen at the 1-position of the benzimidazole skeleton has an aryl group having 6 to 12 carbon atoms.

The carbazole compound is a novel compound that has a high carrier-transport property and can be suitably used for a material of a light-emitting element or for an organic semiconductor material.

Note that in the above carbazole compound, carbon in a benzene ring in the benzimidazole skeleton may have a substituent. The substituent can be any one of an alkyl group having 1 to 4 carbon atoms, a phenyl group, and a tolyl group. Specific examples of the alkyl group having 1 to 4 carbon atoms are a methyl group, an ethyl group, a propyl group, a butyl group, and the like. When there are two or more carbon atoms having substituents, the substituents may be different from each other.

Further, specific examples of the aryl group having 6 to 12 carbon atoms which is bonded to nitrogen at the 1-position of the benzimidazole skeleton are a phenyl group, a naphthyl group, a biphenyl group, and a tolyl group.

Carbon in the dibenzofuran skeleton or the dibenzothiophene skeleton may also have a substituent. The substituent can be either an alkyl group having 1 to 4 carbon atoms or an aryl group having 6 to 12 carbon atoms. Specific examples of the alkyl group having 1 to 4 carbon atoms are a methyl group, an ethyl group, a propyl group, and a butyl group, and specific examples of the aryl group having 6 to 12 carbon atoms are a phenyl group, a naphthyl group, a biphenyl group, and a tolyl group.

Further, the carbazole skeleton in the above carbazole compound may have a substituent at the 6-position, and the substituent can be selected from an alkyl group having 1 to 4 carbon atoms and an aryl group having 6 to 12 carbon atoms. Specific examples of the alkyl group having 1 to 4 carbon atoms are a methyl group, an ethyl group, a propyl group, and a butyl group, and specific examples of the aryl group having 6 to 12 carbon atoms are a phenyl group, a naphthyl group, a biphenyl group, and a tolyl group.

The carbazole compound with such a structure has a high carrier-transport property and can be suitably used for a host material or a carrier-transport layer in a light-emitting element. Owing to the high carrier-transport property of the carbazole compound, a light-emitting element having low driving voltage can be fabricated.

Further, the carbazole compound has a wide band gap, and therefore can be suitably used for a host material, into which an emission center substance that emits blue fluorescence and fluorescence at a longer wavelength than blue or an emission center substance that emits green phosphorescence and phosphorescence at a longer wavelength than green is dispersed. Since the carbazole compound has a wide band gap and thus high triplet excitation energy, the energy of carriers that are recombined in the host material can be effectively transferred to the emission center substance. Accordingly, a light-emitting element with high emission efficiency can be fabricated.

Also for a carrier-transport layer adjacent to a light-emitting layer containing an emission center substance that emits blue fluorescence or an emission center substance that emits green phosphorescence, the carbazole compound having a wide band gap can be suitably used without deactivating excitation energy of the emission center substance. Accordingly, a light-emitting element with high emission efficiency can be fabricated.

The above-described carbazole compound can also be represented by the general formula (G1) below.

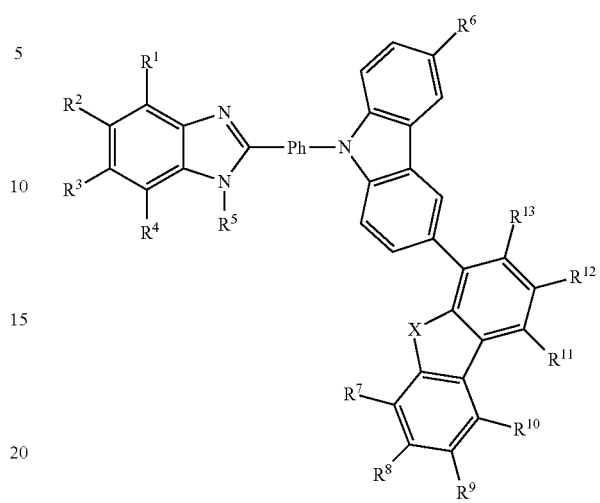

(G1)

In the formula, $R^1$ to $R^4$ separately represent any one of hydrogen, an alkyl group having 1 to 4 carbon atoms, a phenyl group, and a tolyl group, and $R^5$ represents an aryl group having 6 to 12 carbon atoms. X represents a sulfur atom or an oxygen atom.

Further, $R^6$ to $R^{13}$ separately represent any one of hydrogen, an alkyl group having 1 to 4 carbon atoms, and a substituted or unsubstituted aryl group having 6 to 12 carbon atoms. When the aryl group has a substituent, an alkyl group having 1 to 4 carbon atoms is a specific example of the substituent.

In addition, Ph represents a substituted or unsubstituted phenylene group; when the phenylene group has a substituent, the substituent can be an alkyl group having 1 to 4 carbon atoms.

Specific examples of the groups represented by $R^1$ to $R^4$ in the general formula (G1) are groups represented by the following structural formulae (R-1) to (R-13).

(R-1) H—

(R-2) CH₃—

(R-3) H₃C—CH₂—

(R-4) CH₃—H₂C—CH₂—

(R-5) H₃C—CH—CH₃—

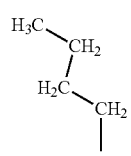 (R-6)
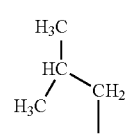 (R-7)
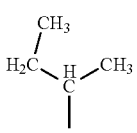 (R-8)
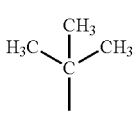 (R-9)
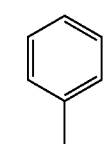 (R-10)
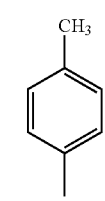 (R-11)
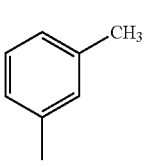 (R-12)
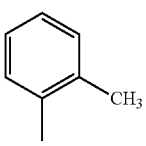 (R-13)
Specific examples of the group represented by $R^5$ in the general formula (G1) are groups represented by the following structural formulae ($R^5$-1) to ($R^5$-11).
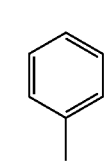 ($R^5$-1)
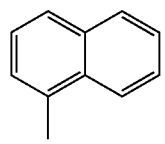 ($R^5$-2)
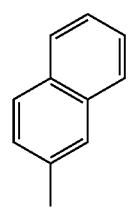 ($R^5$-3)
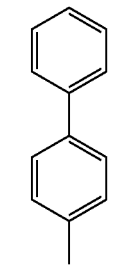 ($R^5$-4)
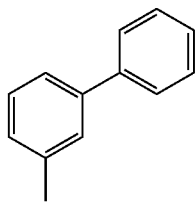 ($R^5$-5)
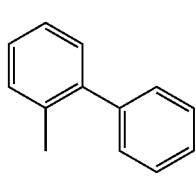 ($R^5$-6)
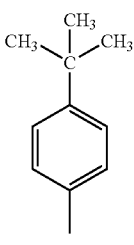 ($R^5$-7)
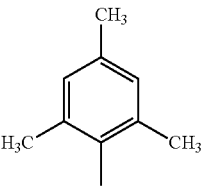 ($R^5$-8)

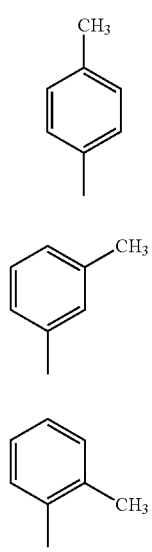
(R⁵-9)
(R⁵-10)
(R⁵-11)
Specific examples of the groups represented by $R^6$ to $R^{13}$ in the general formula (G1) are groups represented by the following structural formulae (R-1) to (R-20).
(R-1) H
(R-2) CH₃
(R-3) H₃C–CH₂
(R-4) CH₃–H₂C–CH₂
(R-5) H₃C–CH–CH₃
(R-6) H₃C–CH₂–H₂C–CH₂
(R-7) H₃C–HC(CH₃)–CH₂
(R-8) H₂C(CH₃)–CH–CH₃
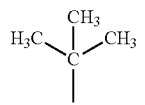
(R-9)
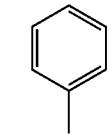
(R-10)
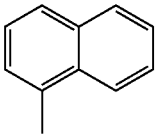
(R-11)
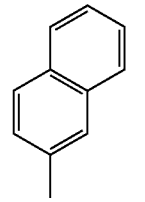
(R-12)
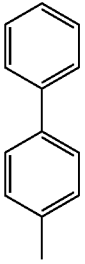
(R-13)
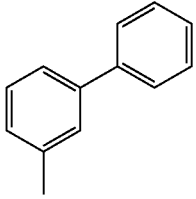
(R-14)
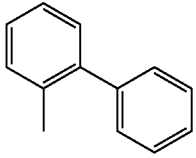
(R-15)
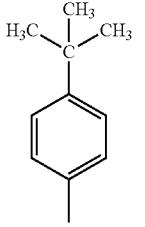
(R-16)

-continued (R-17)
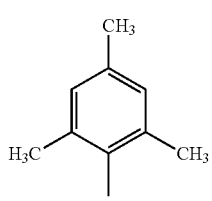

(R-18)
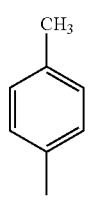

(R-19)
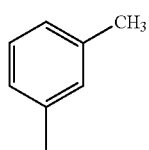

(R-20)
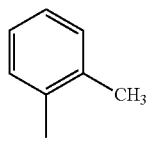

It is preferable in the above general formula (G1) that, when the dibenzothiophene skeleton or the dibenzofuran skeleton has a substituent, the substituent be positioned at one or more of $R^7$, $R^9$, and $R^{12}$. Such a substituent can be introduced easily through bromination or conversion into boronic acid because of the ease of synthesis. The structure in which $R^7$ to $R^{13}$ are each hydrogen is further preferable because this structure is advantageous in terms of high availability of a material and can be inexpensively synthesized. For the same reason, also $R^1$ to $R^4$ and $R^6$ are preferably each hydrogen.

As Ph, a para-substituted phenyl group is preferred because a high carrier-transport property can be obtained and an improvement in thermophysical property (for example, a glass-transition temperature: Tg) can also be expected.

Further, a meta-substituted phenylene group is preferred because the use thereof makes the structure of the carbazole compound represented by the general formula (G1) more three-dimensional than that with a para-substituted phenylene group so that an amorphous state can be easily kept when a film is formed. In addition, a wider band gap and a higher T1 level than with a para-substituted phenylene group can also be expected.

Specific examples of structures of the carbazole compound represented by the above general formula (G1) are substances represented by the following structural formulae (100) to (162) and (200) to (262), and the like.

(100)
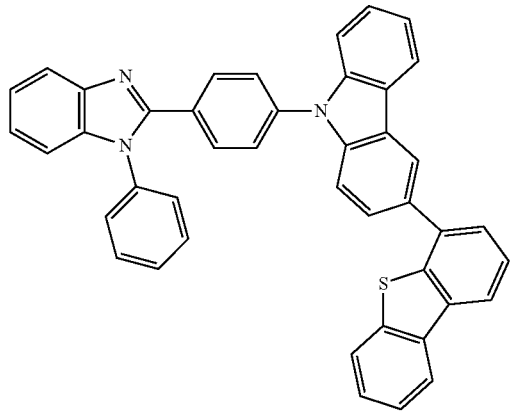

(101)
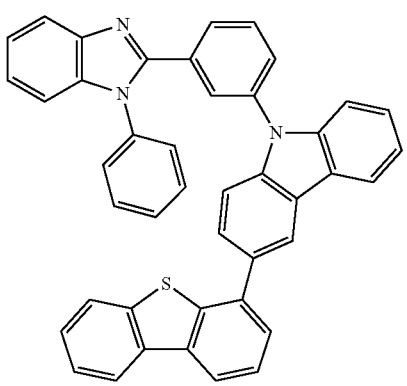

(102)
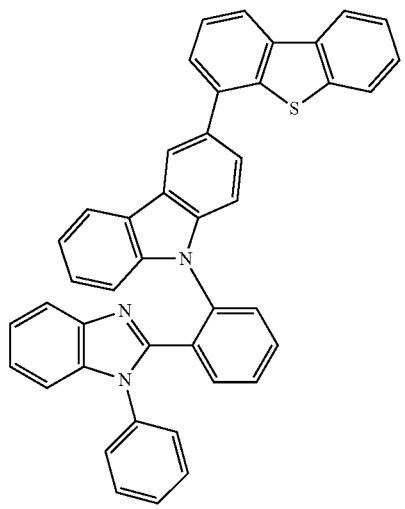

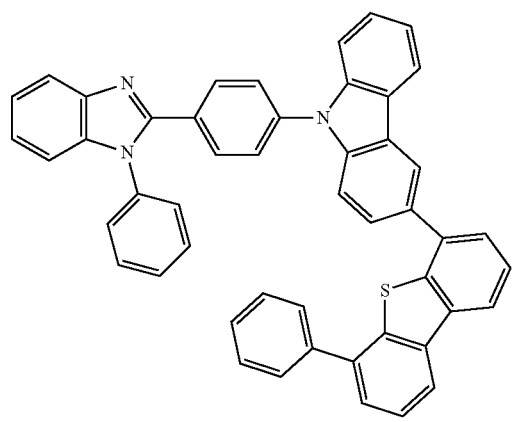
(103)
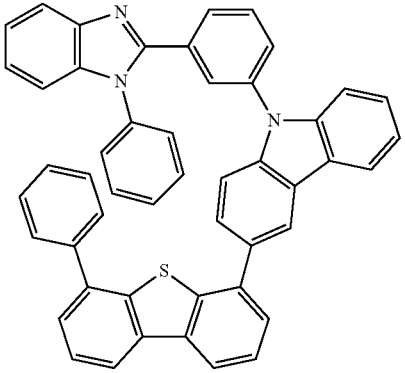
(106)
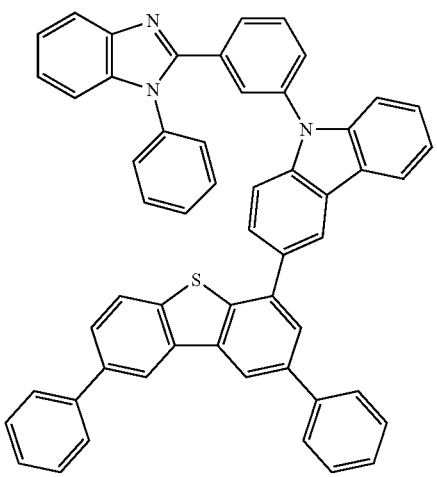
(104)
(107)
(105)
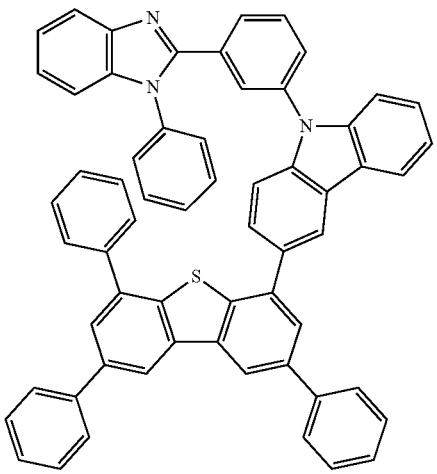
(108)

(109)
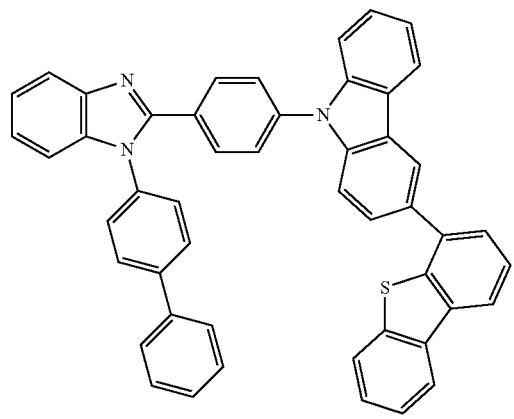
(110)
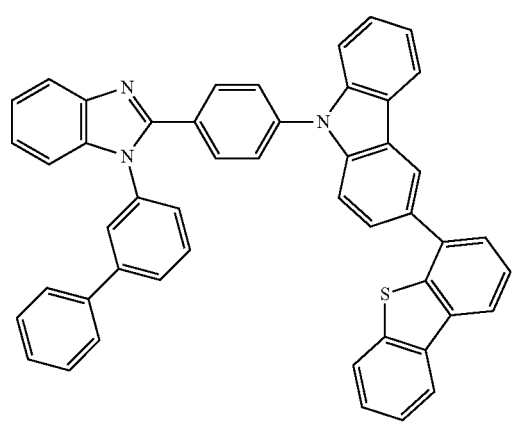
(111)
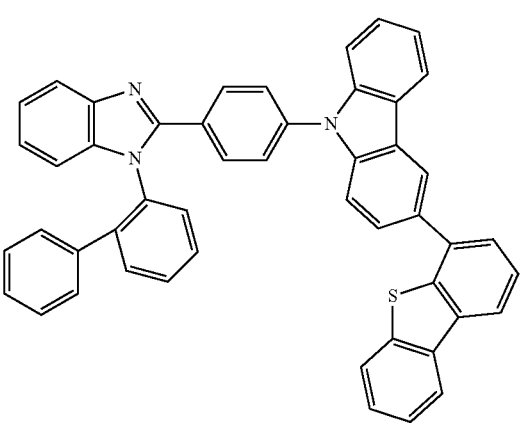
(112)
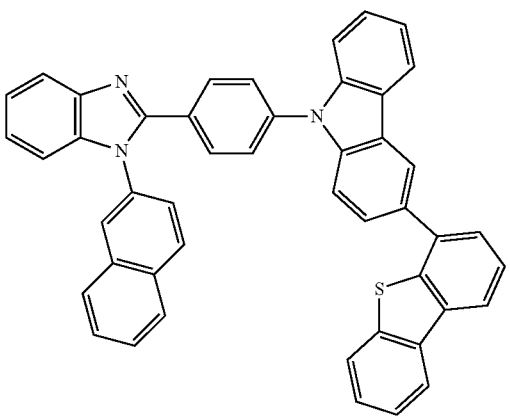
(113)
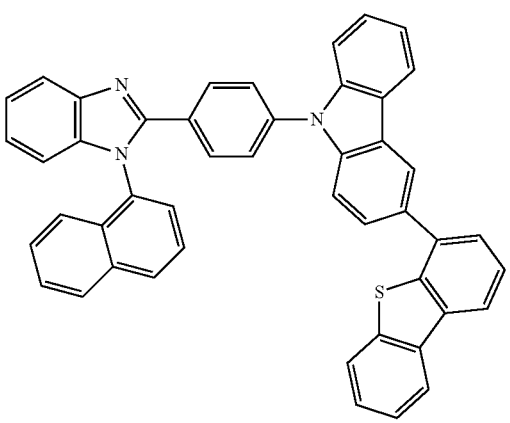
(114)
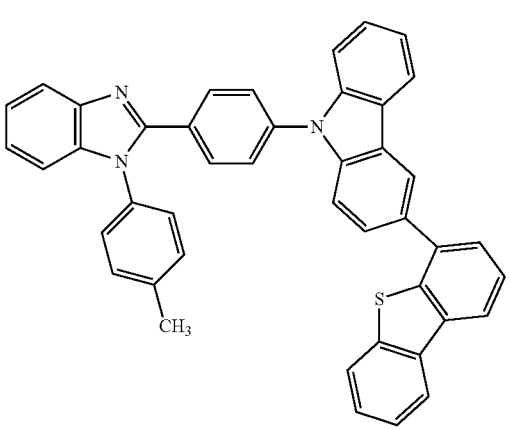

(115)
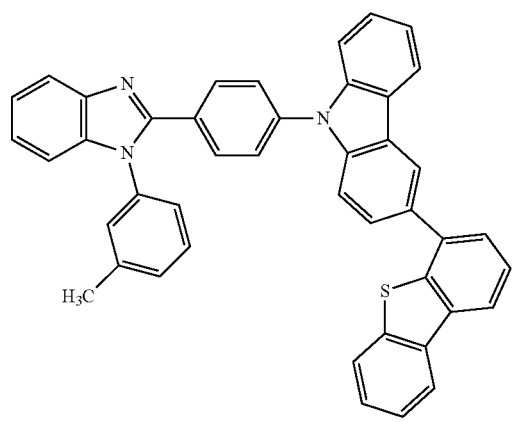
(118)
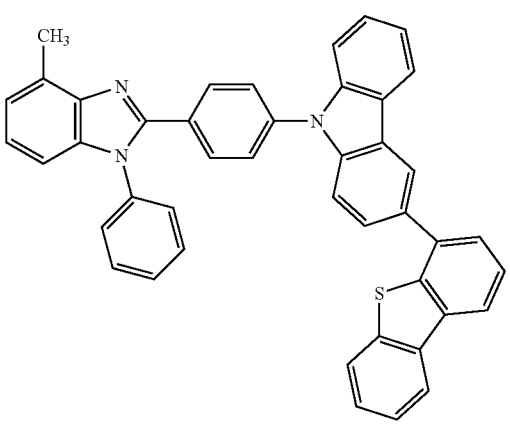
(116)
(119)
(117)
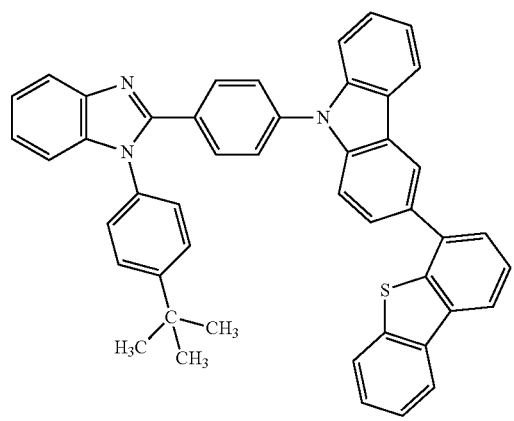
(120)
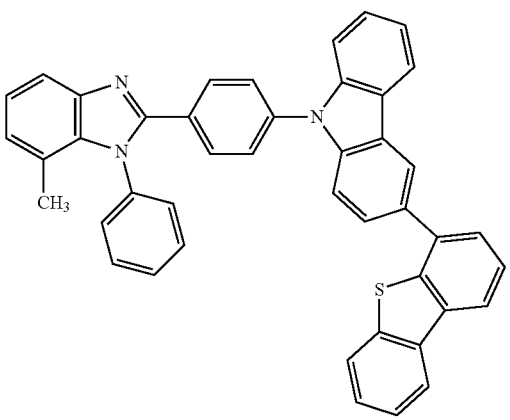

(121)
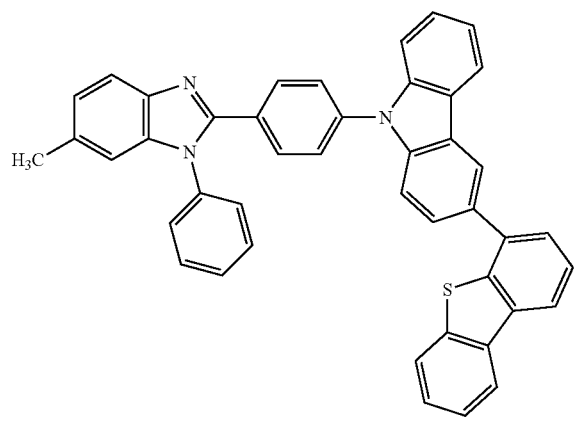
(122)
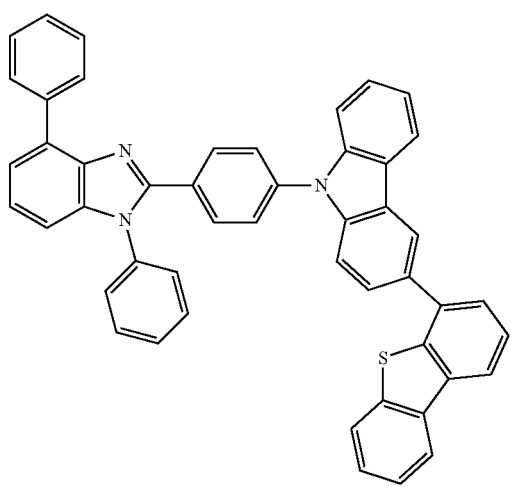
(123)
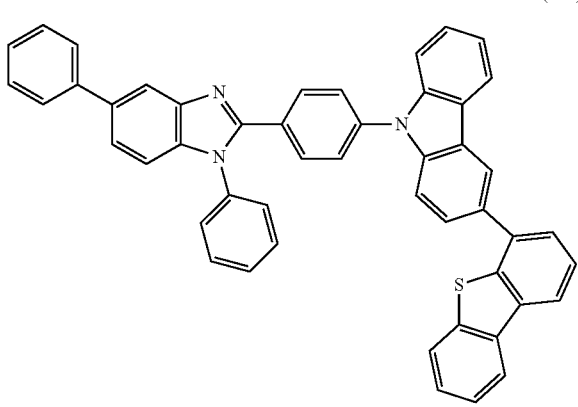
(124)
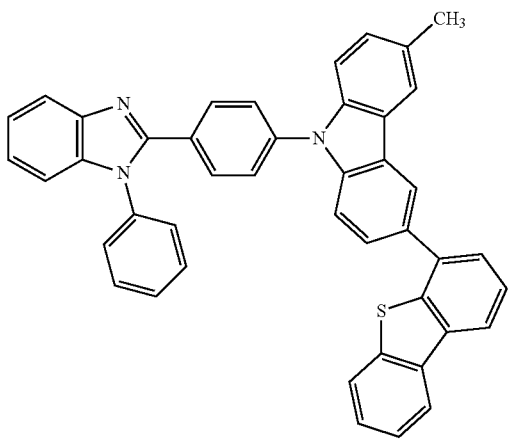
(125)
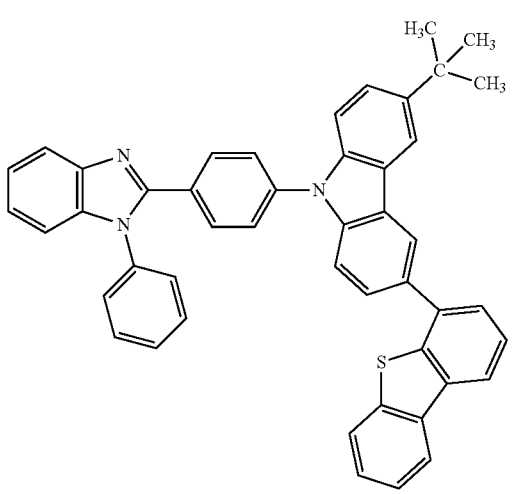
(126)
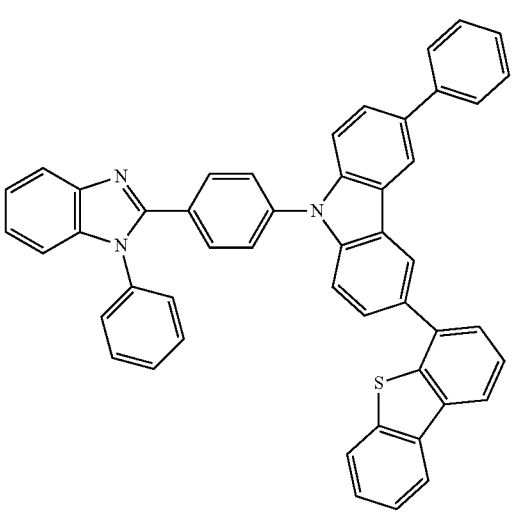

(127)
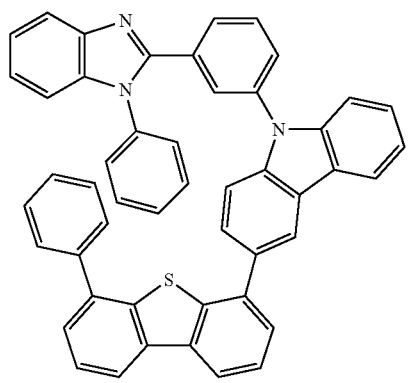
(128)
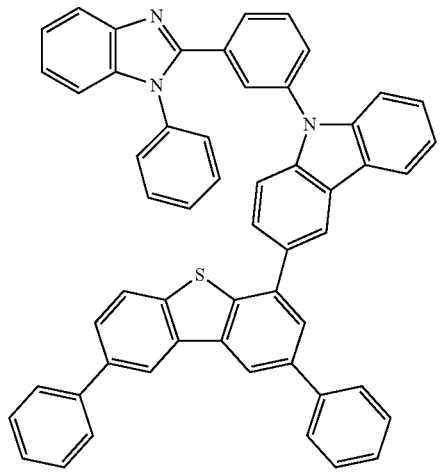
(129)
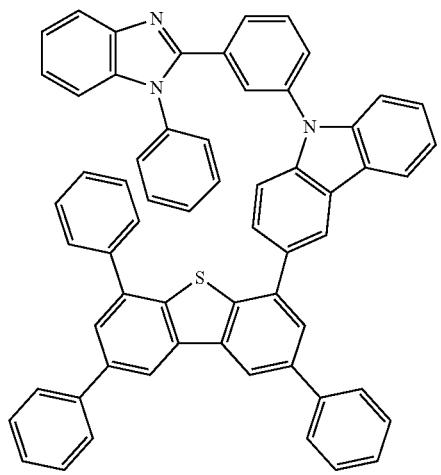
(130)
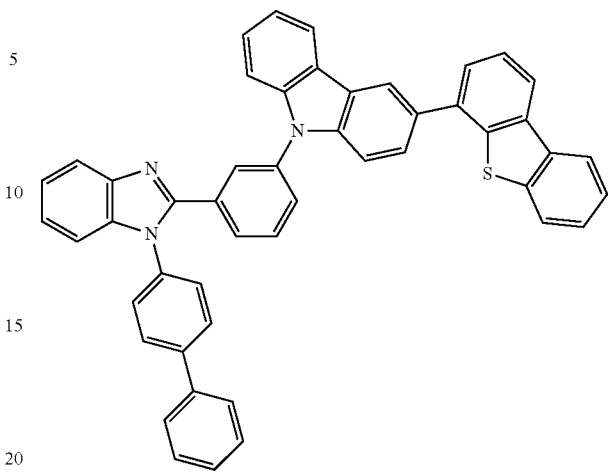
(131)
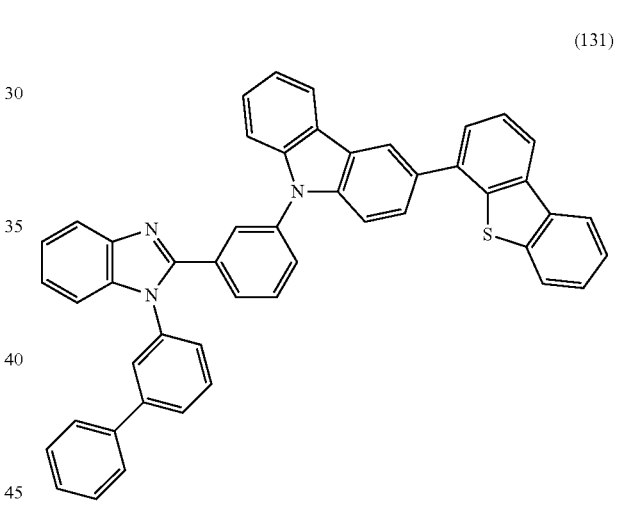
(132)
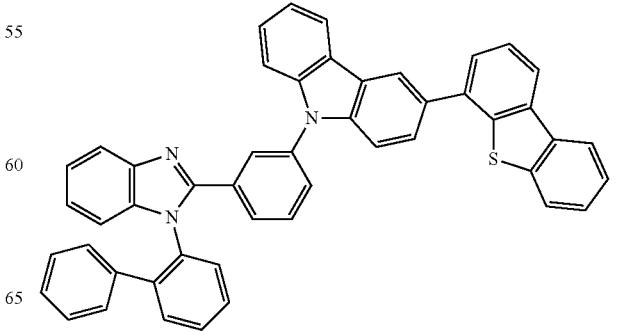

(133)
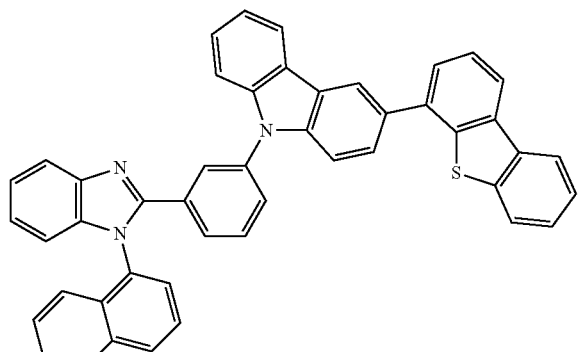
(134)
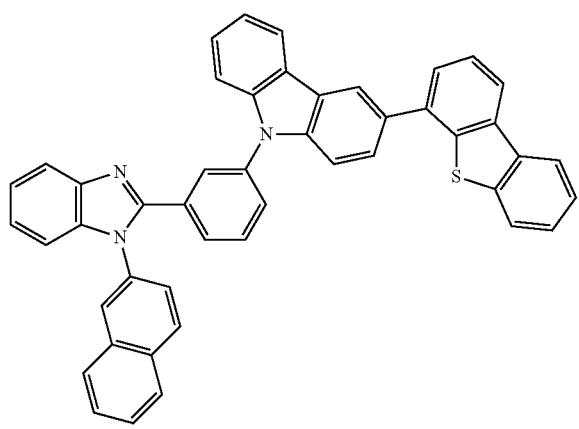
(135)
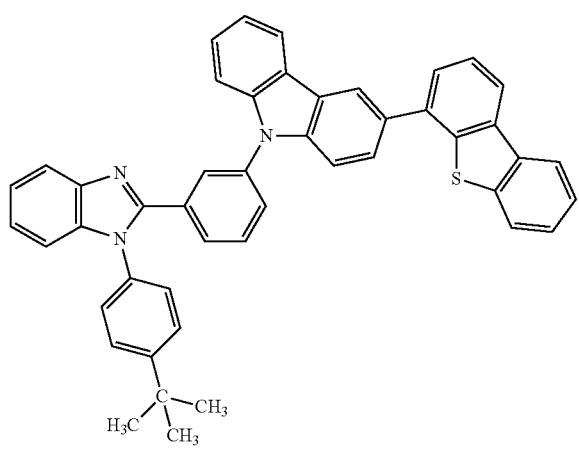
(136)
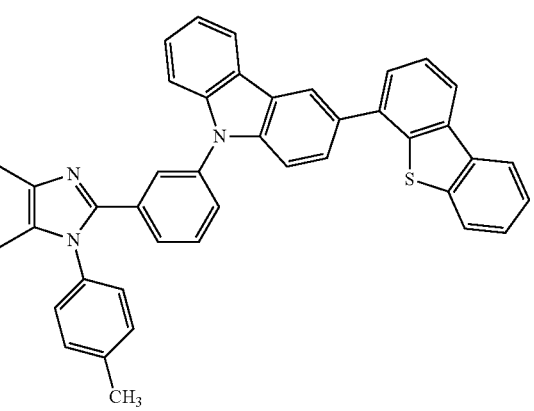
(137)
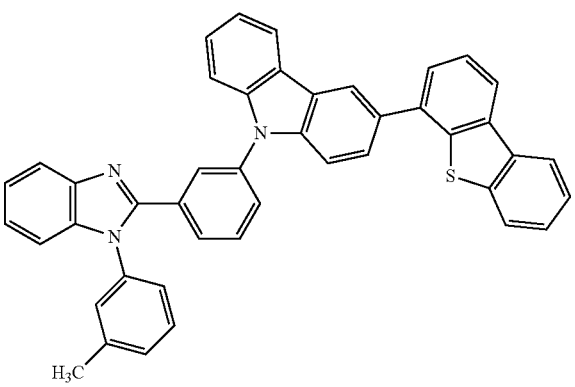
(138)
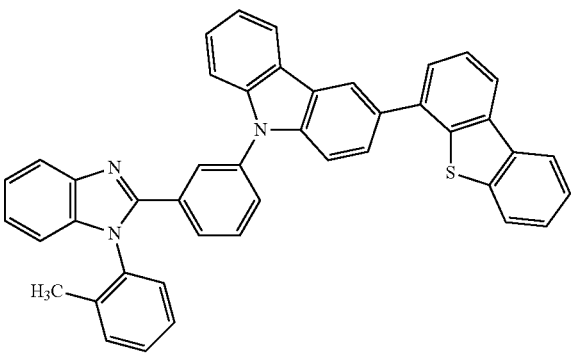

(139)
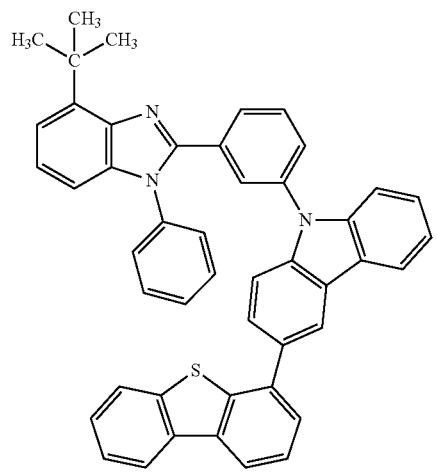
(140)
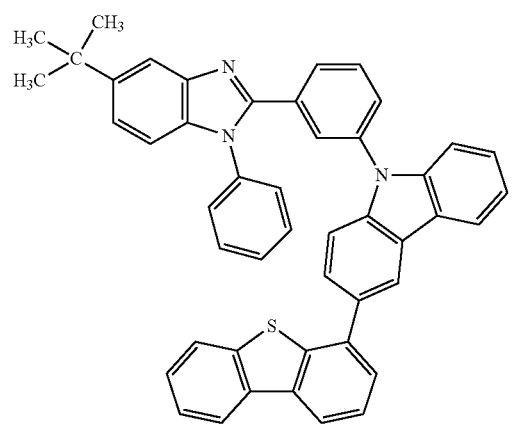
(141)
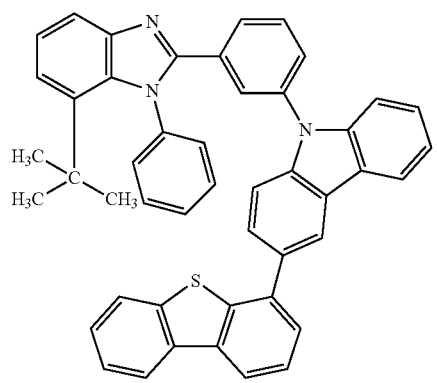
(142)
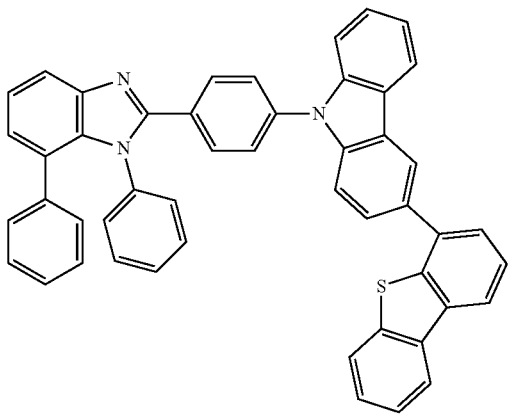
(143)
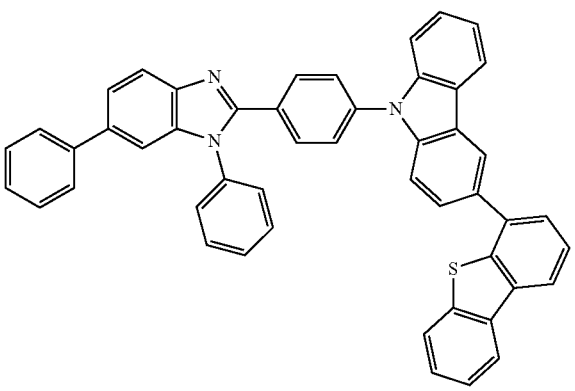
(144)
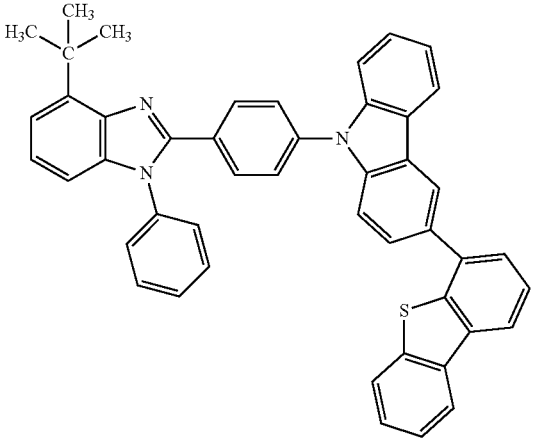

(145)
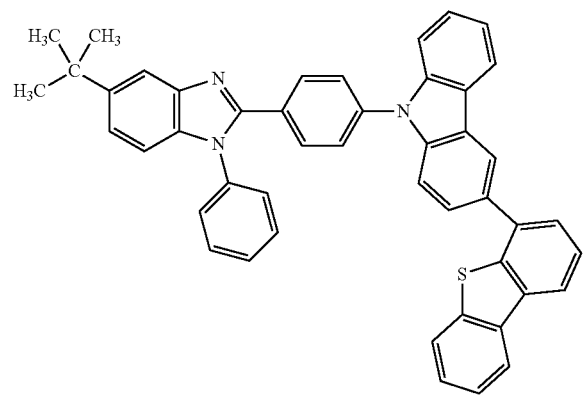
(146)
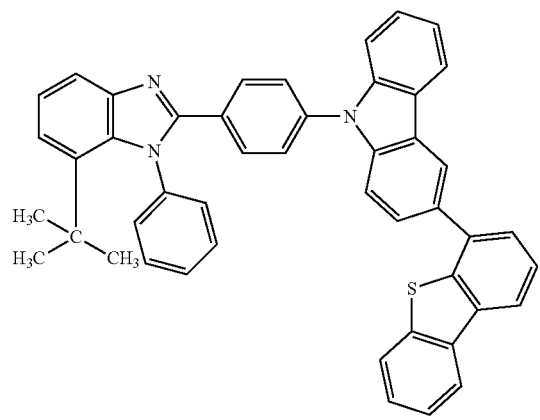
(147)
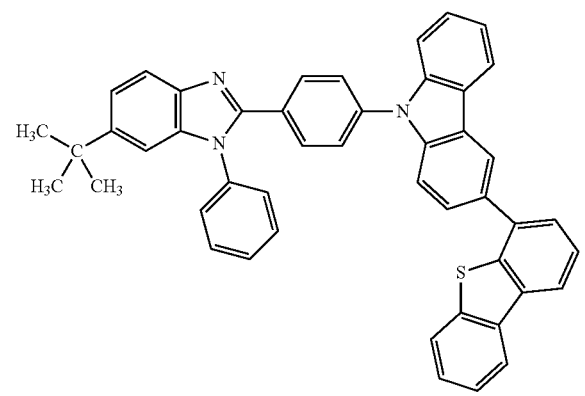
(148)
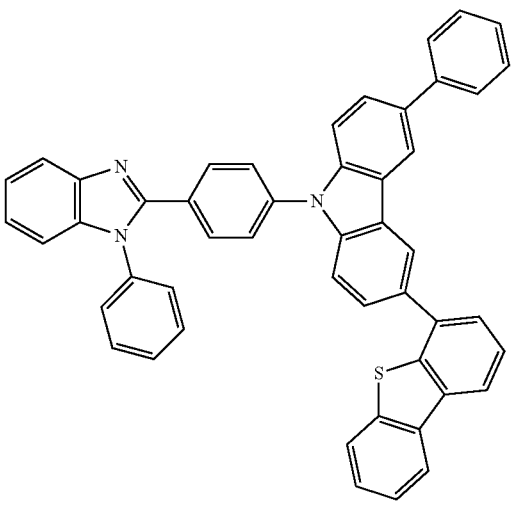
(149)
(150)
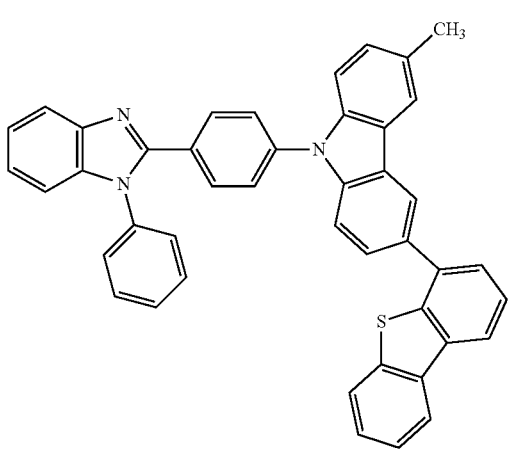

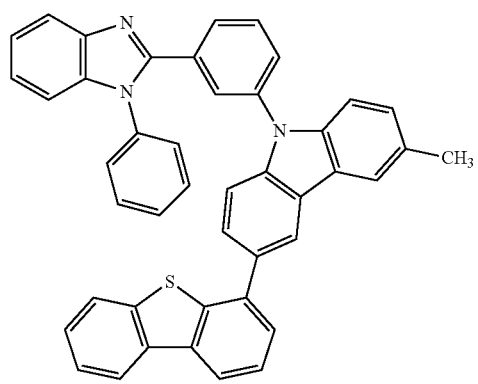
(151)
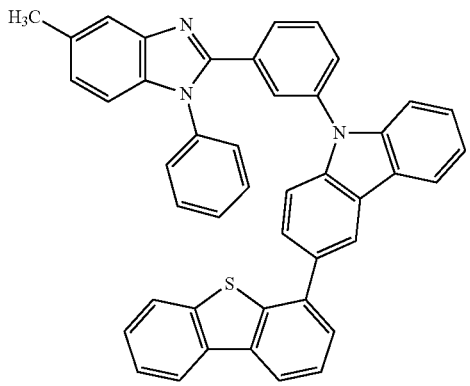
(154)
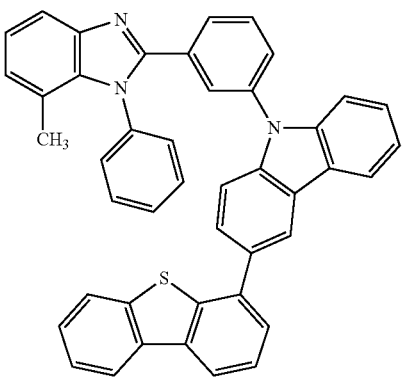
(152)
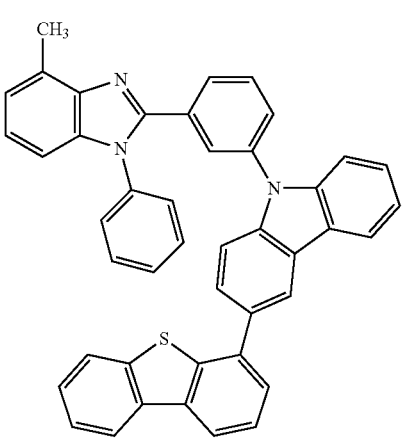
(155)
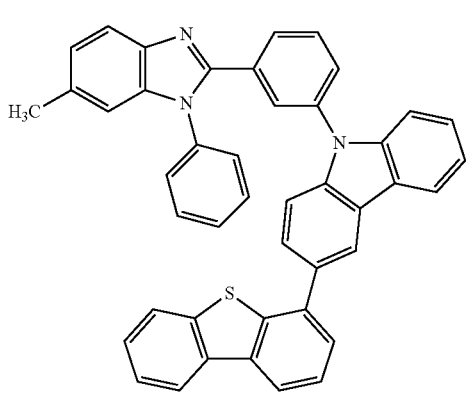
(153)
(156)
(157)

(158) 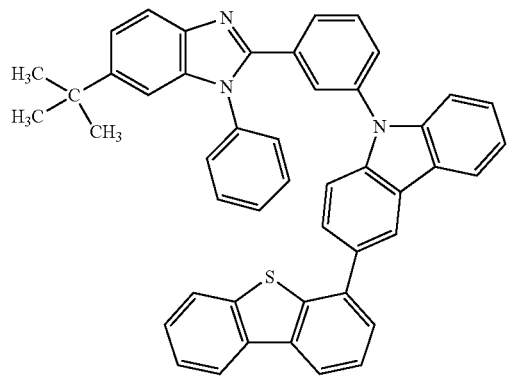
(159) 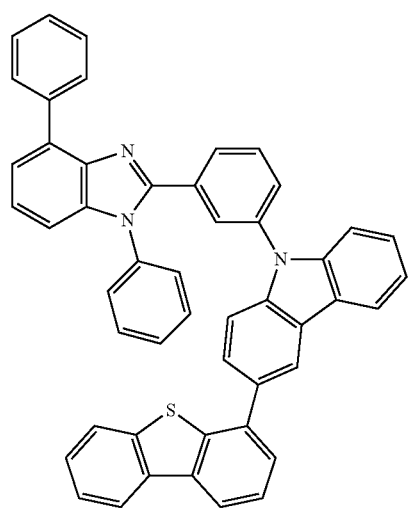
(160) 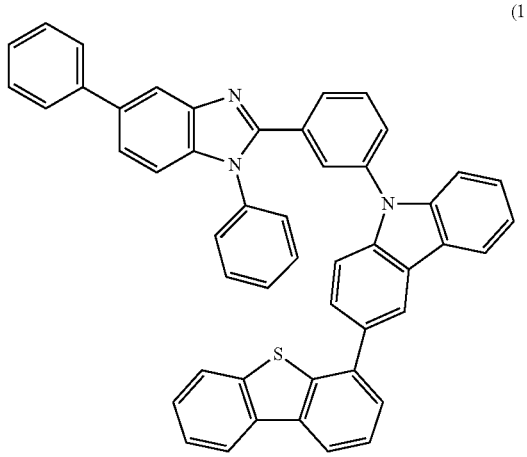
(161) 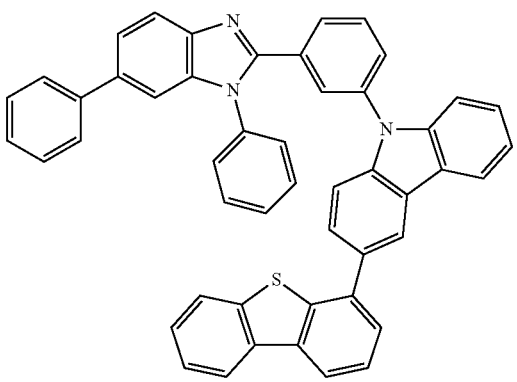
(162) 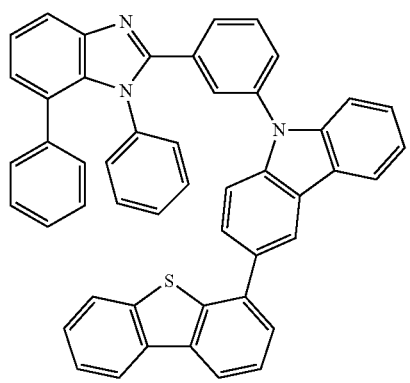
(200) 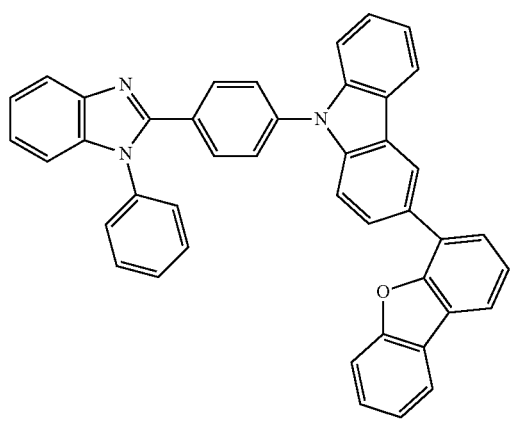
(201) 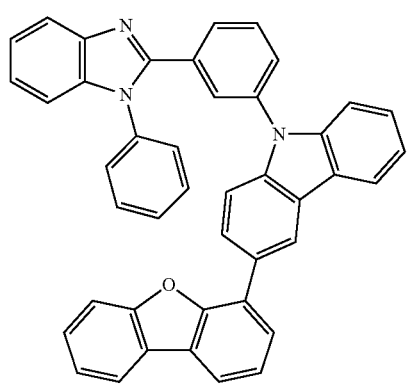

(202)
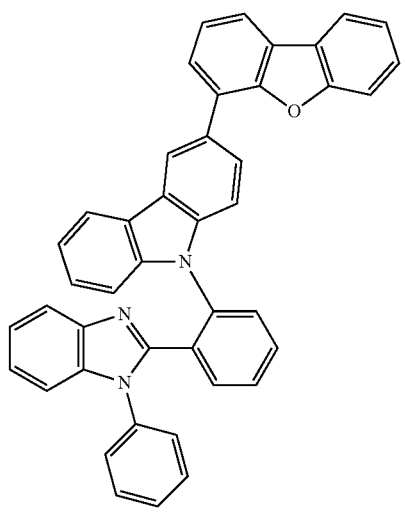
(203)
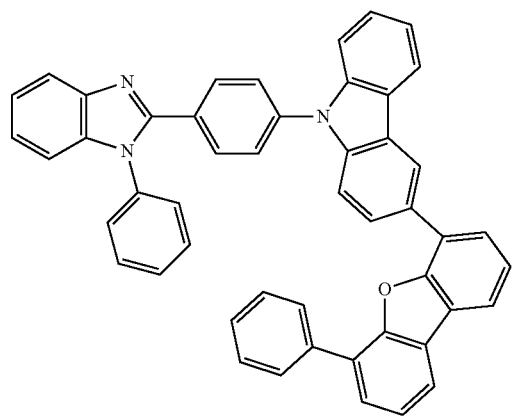
(204)
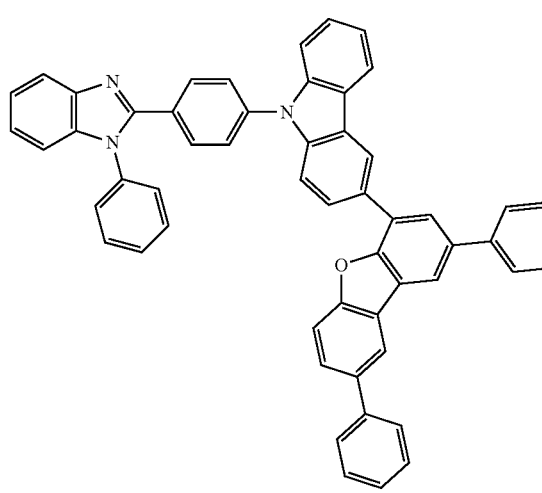
(205)
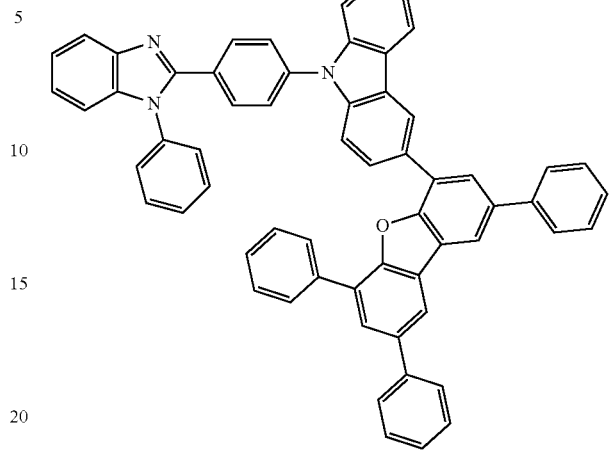
(206)
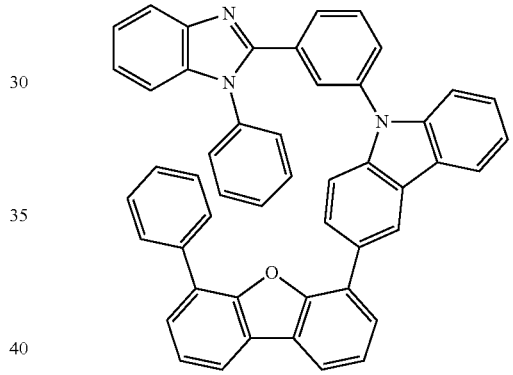
(207)
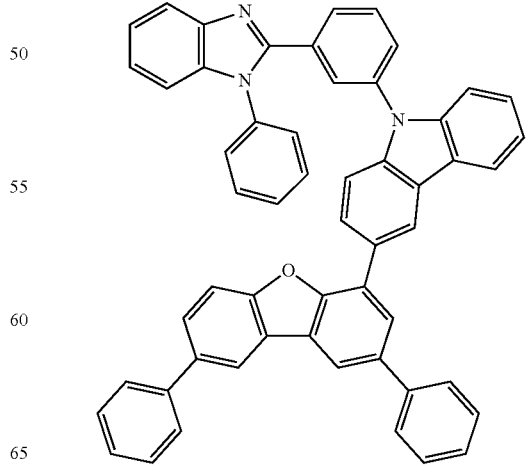

(208)
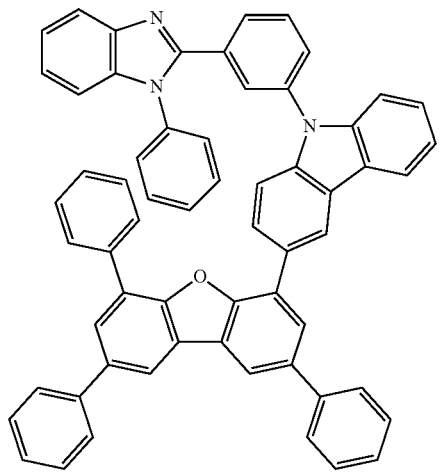
(209)
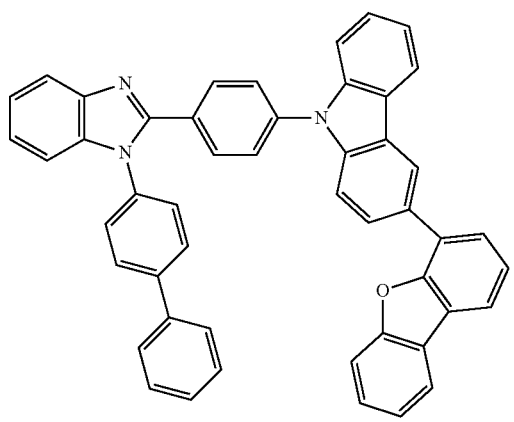
(210)
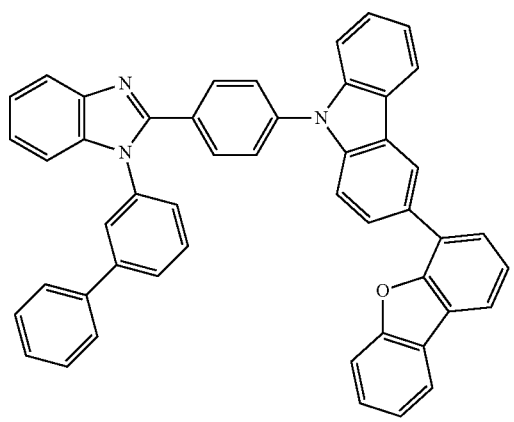
(211)
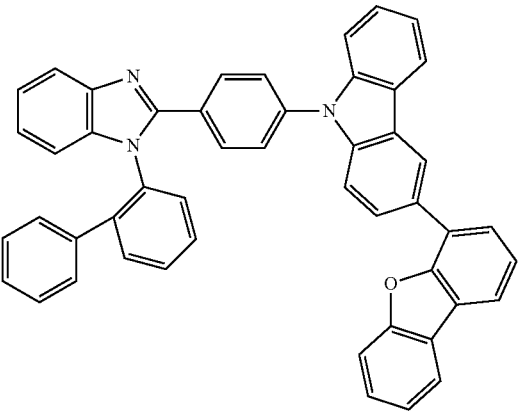
(212)
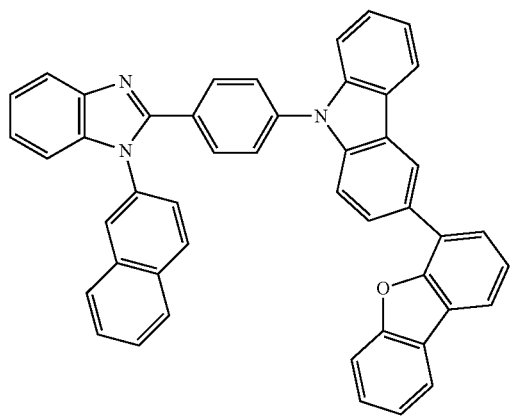
(213)
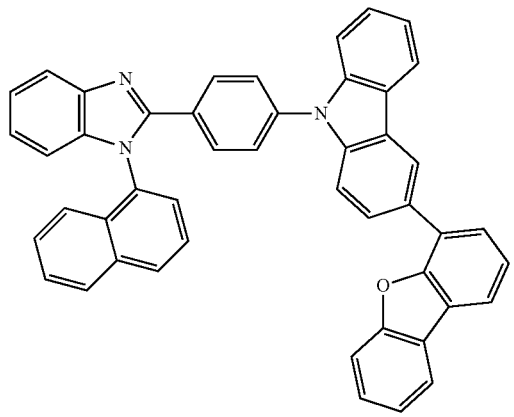

(214)
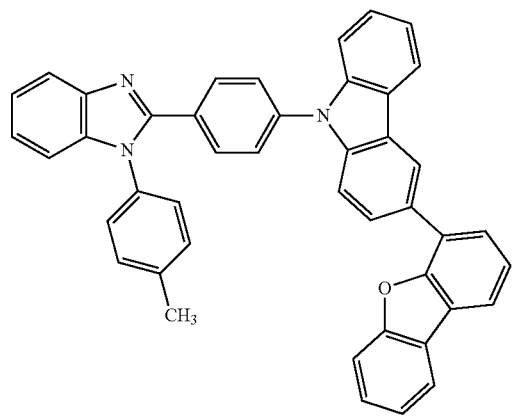
(215)
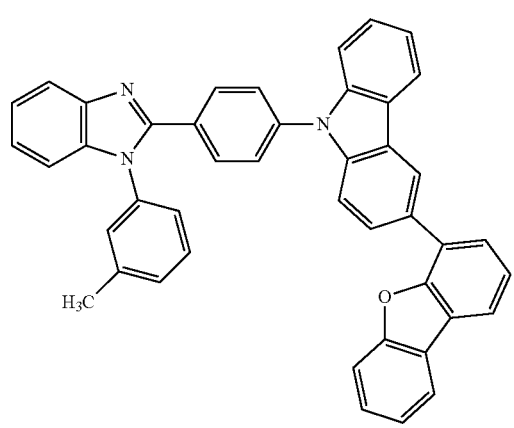
(216)
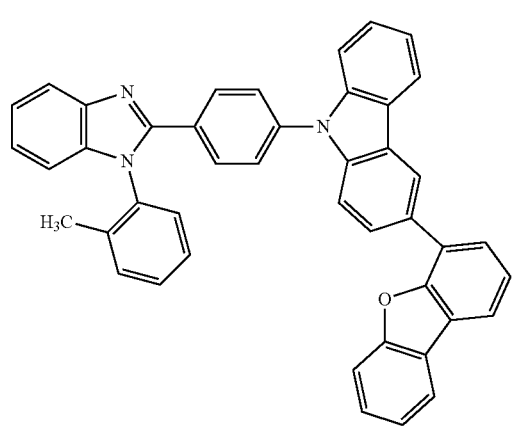
(217)
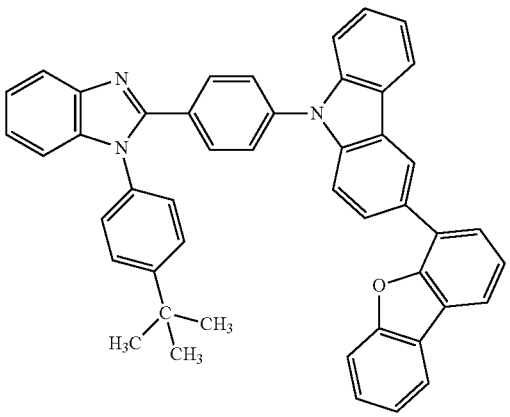
(218)
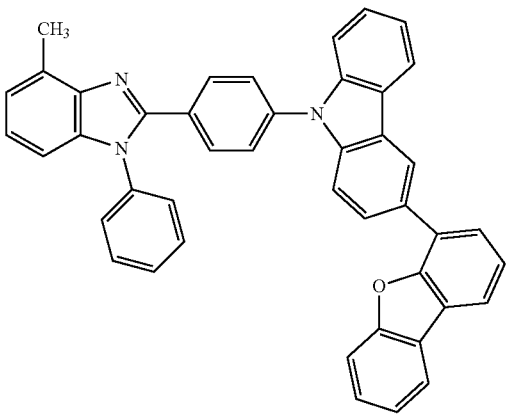
(219)
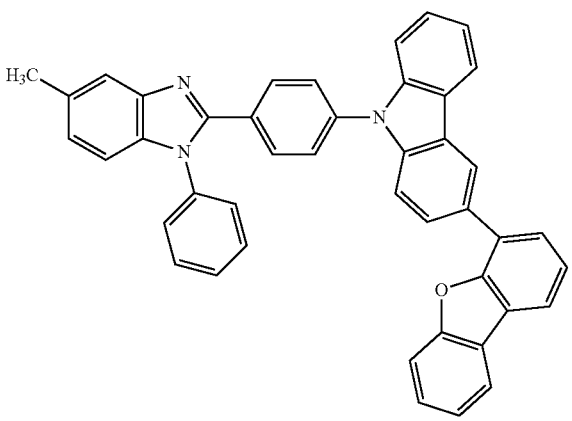

(220)
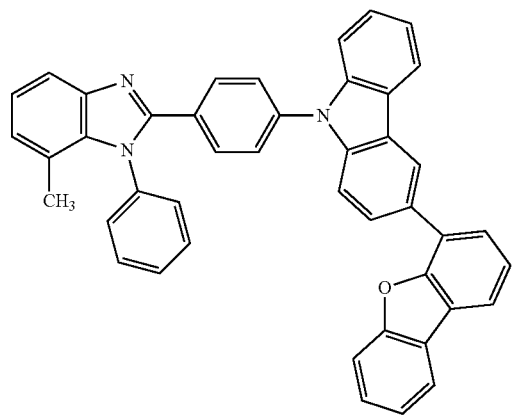
(223)
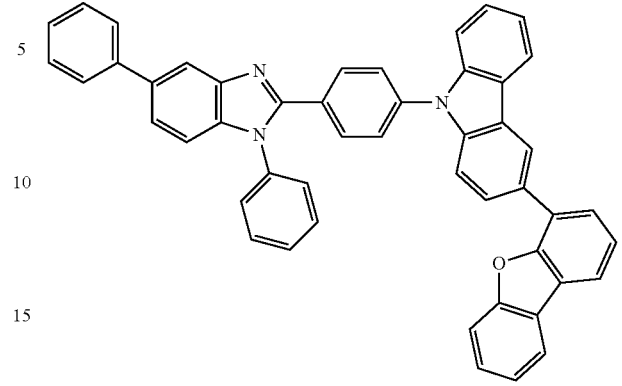
(221)
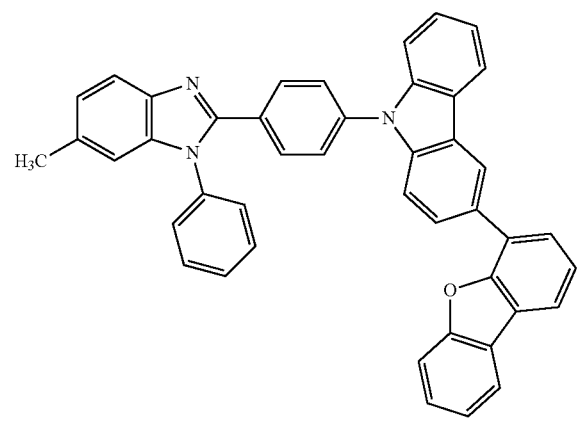
(224)
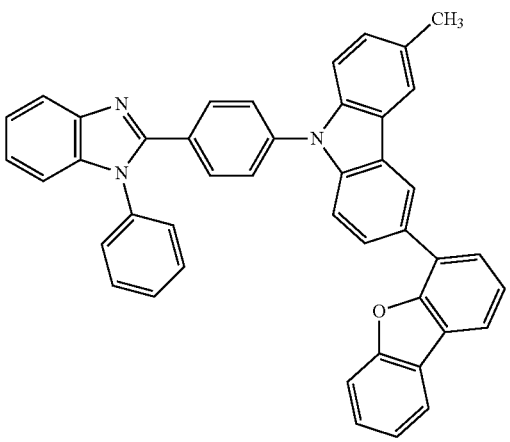
(222)
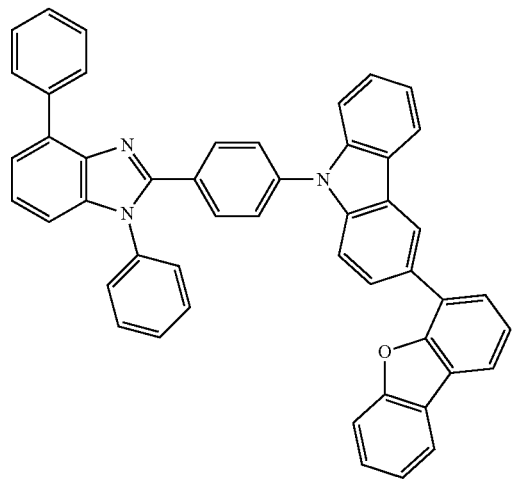
(225)
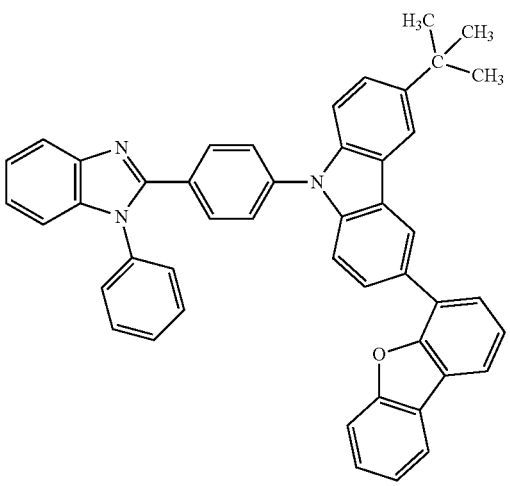

(226)
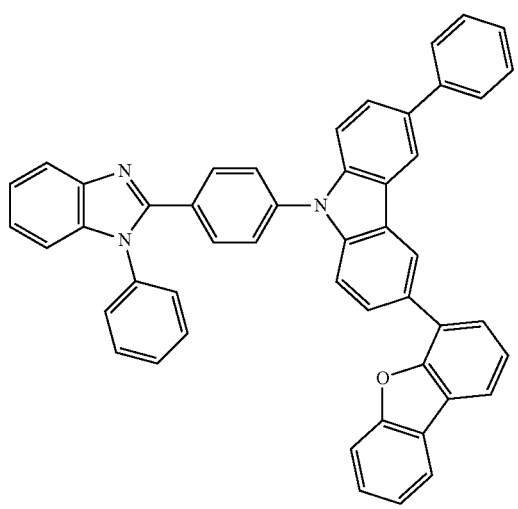
(229)
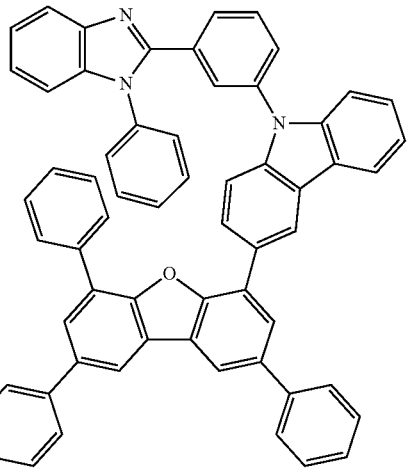
(227)
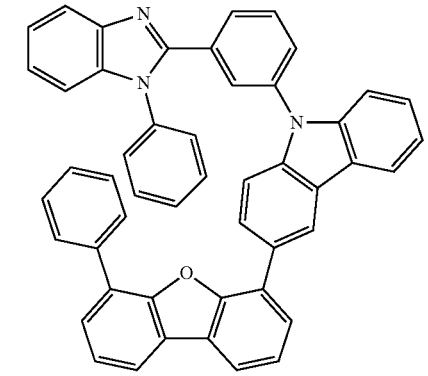
(230)
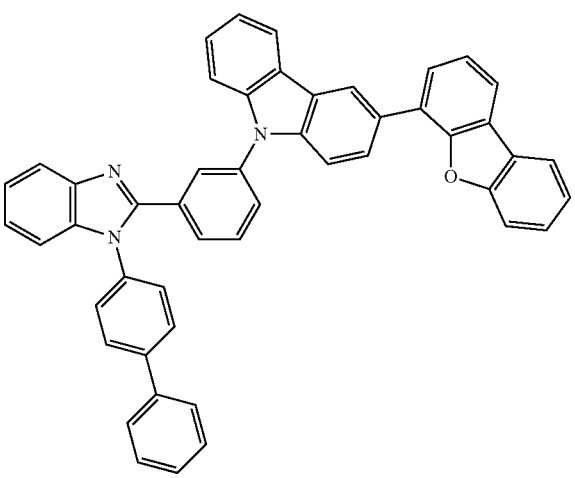
(228)
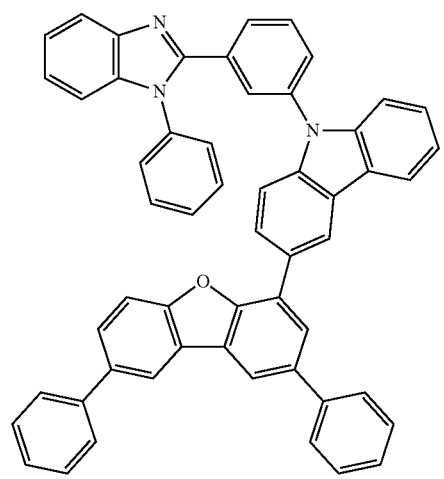
(231)
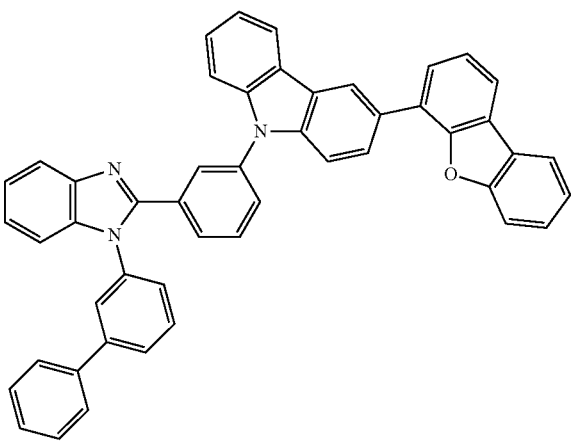

(232)
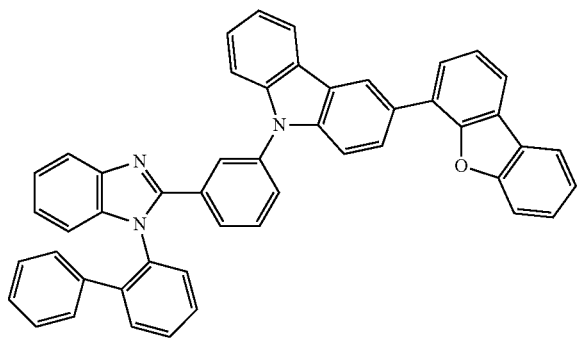
(233)
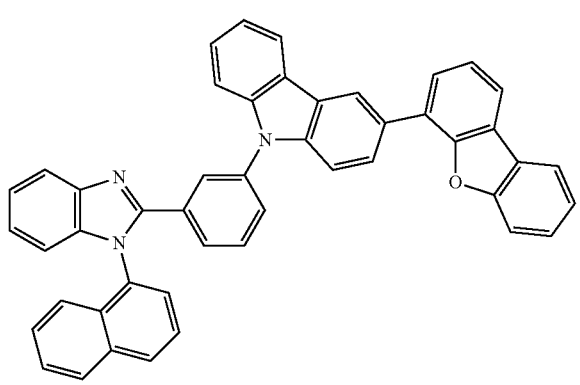
(234)
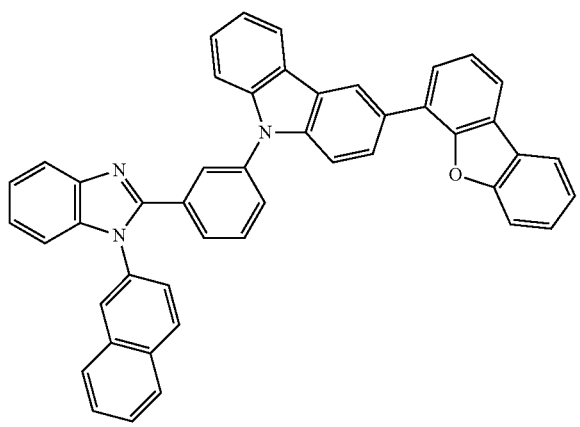
(235)
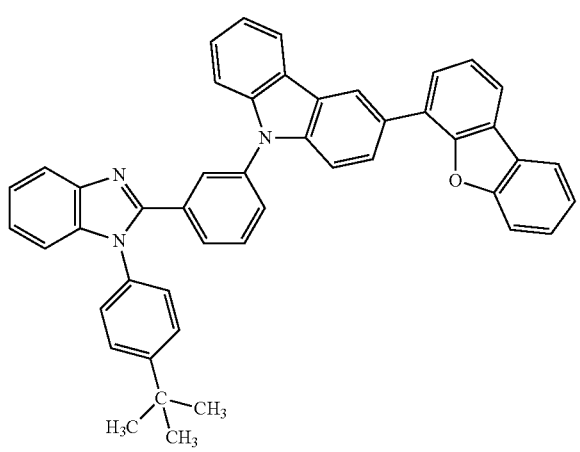
(236)
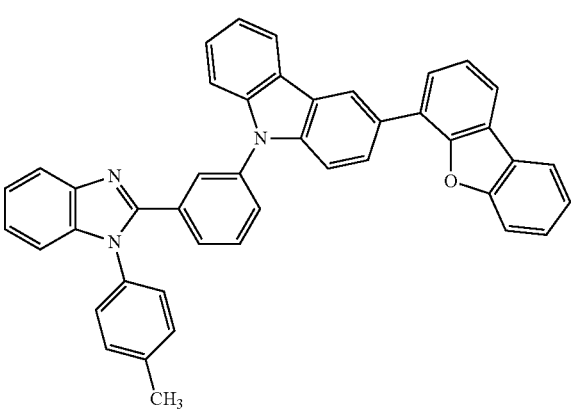
(237)
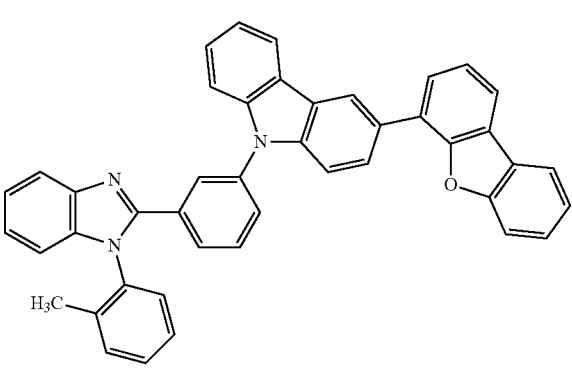
(238)

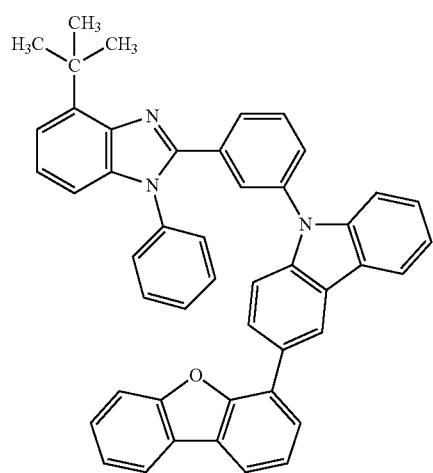
(239)
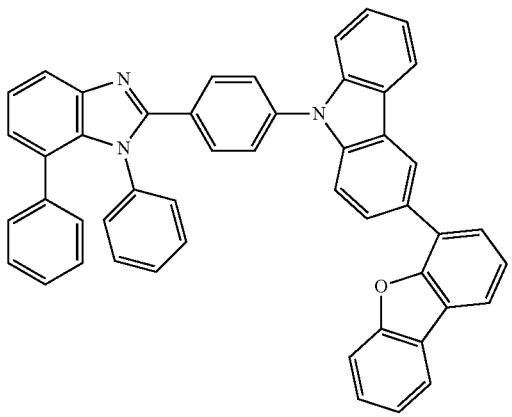
(242)
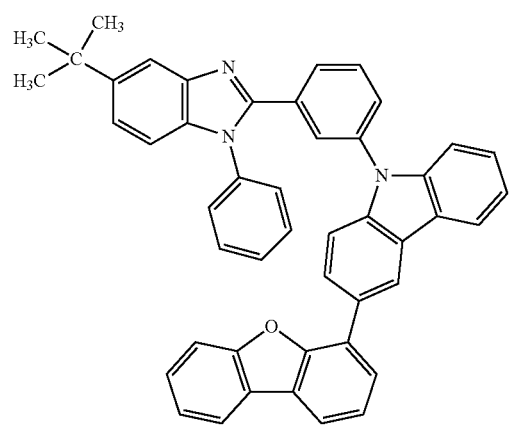
(240)
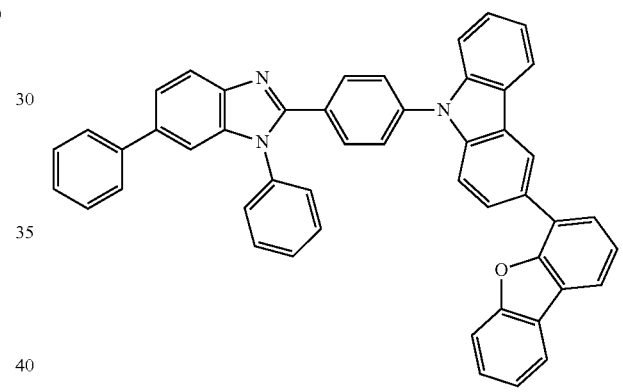
(243)
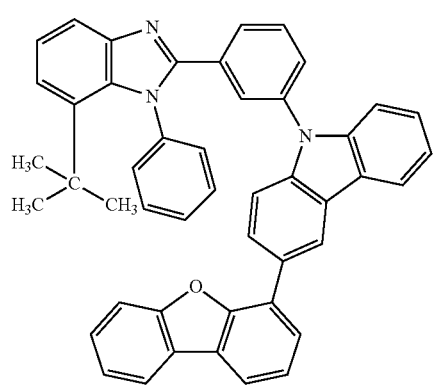
(241)
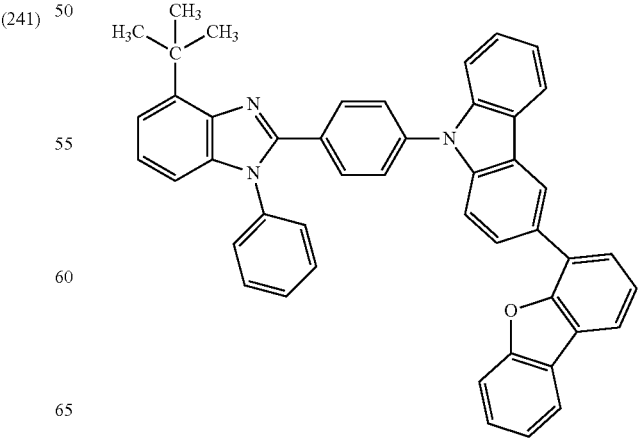
(244)

(245)
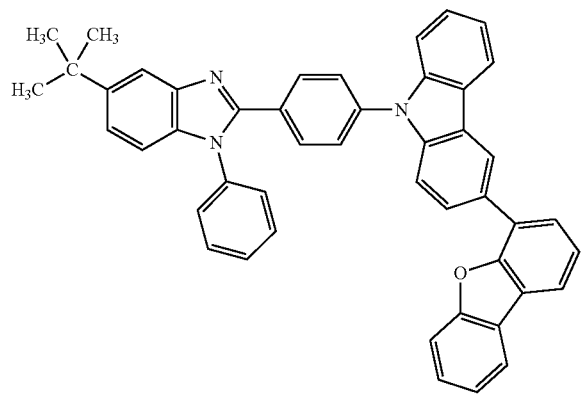
(246)
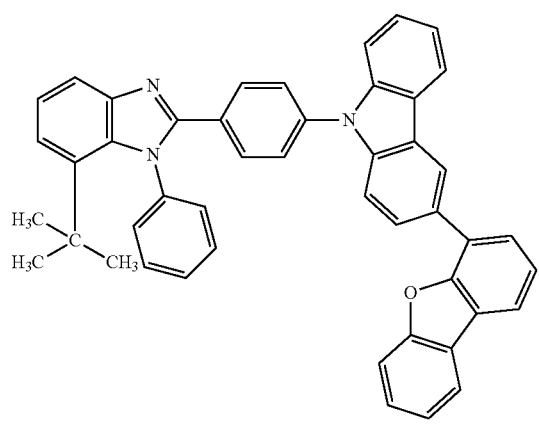
(247)
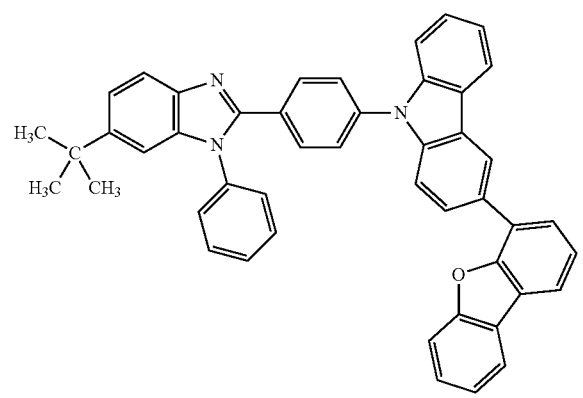
(248)
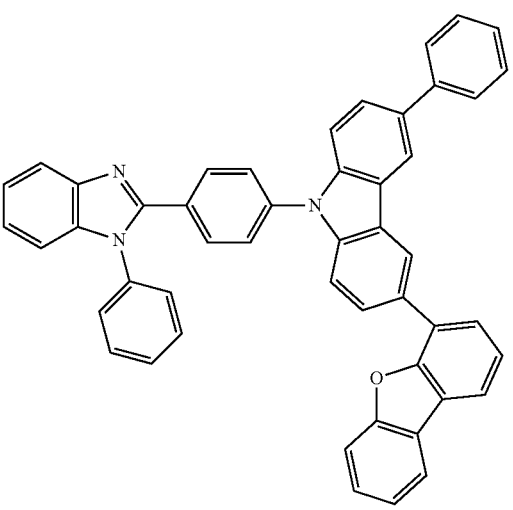
(249)
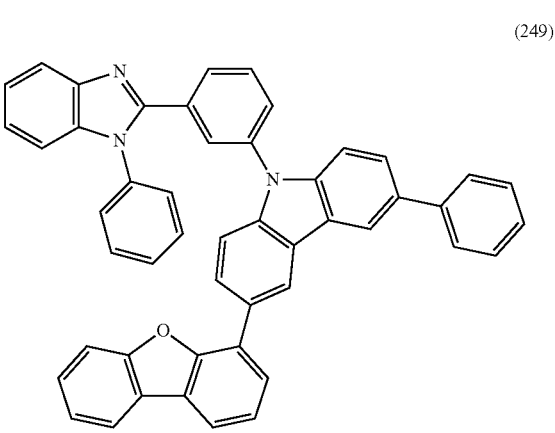
(250)
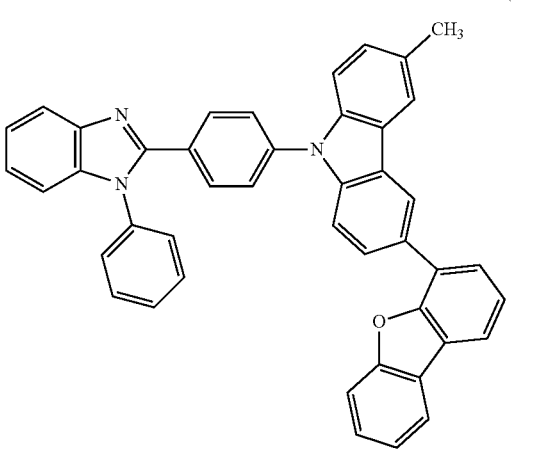

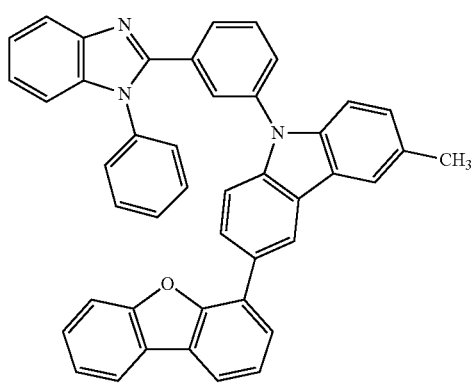
(251)
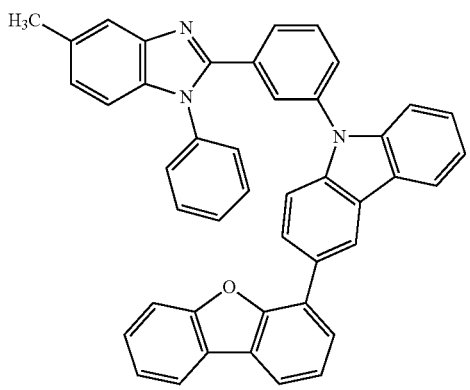
(254)
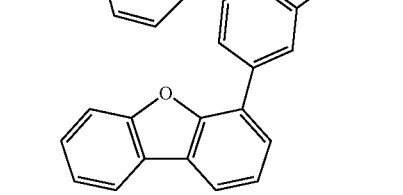
(255)
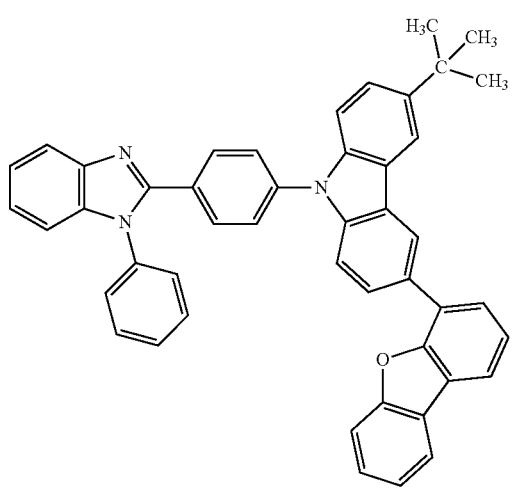
(252)
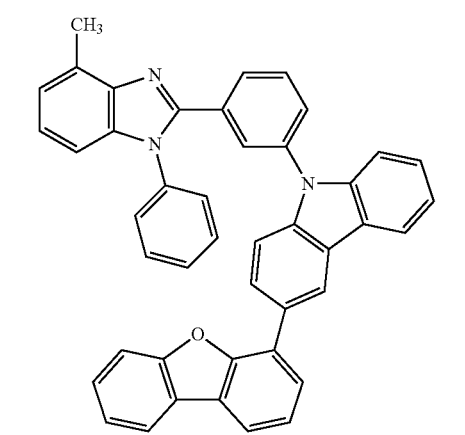
(256)
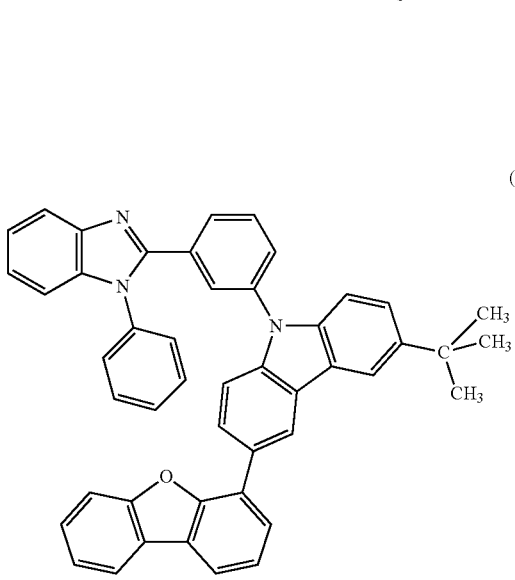
(253)
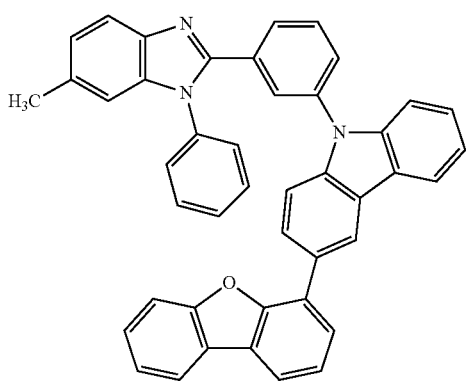
(257)

(258)
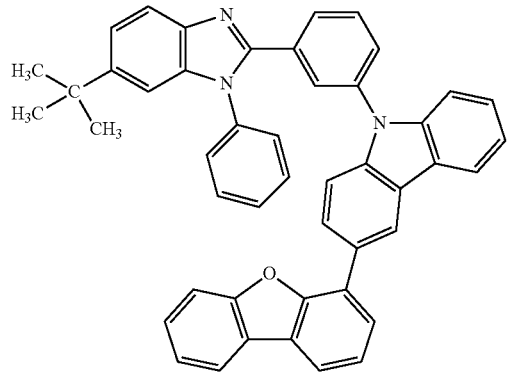

(259)
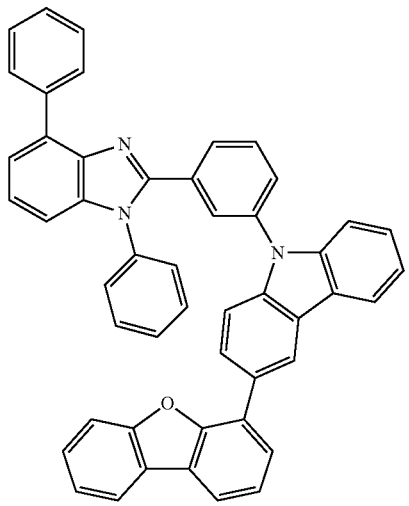

(260)
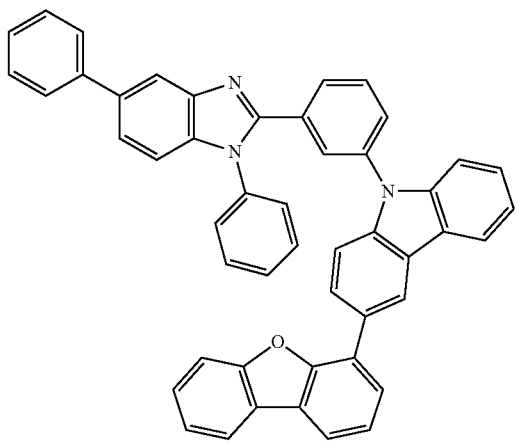

(261)
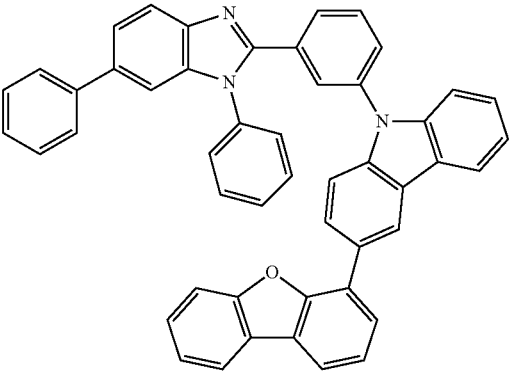

(262)
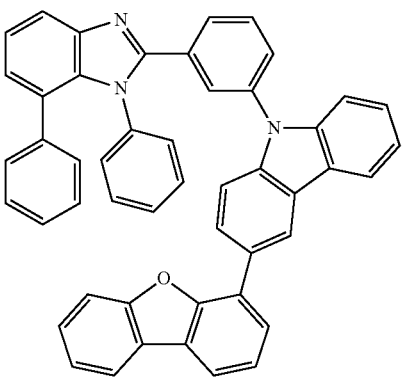

The above-described carbazole compounds have an excellent carrier-transport property and therefore are suitable for a carrier-transport material or a host material; accordingly, a light-emitting element having low driving voltage can also be provided. Further, the carbazole compounds have high triplet excitation energy (a large energy difference between a triplet excited state and a ground state), so that a phosphorescent light-emitting element having high emission efficiency can be obtained. In addition, since having high triplet excitation energy indicates also having a wide band gap, the carbazole compounds enable even a light-emitting element for emitting blue fluorescence to efficiently emit light. Furthermore, the carbazole compounds described in this embodiment have a bipolar transport property; accordingly, localization of a light-emitting region is suppressed and the influence of triplet-triplet annihilation or the like can be reduced, which contributes to improvement of emission efficiency. Furthermore, the carbazole compounds in this embodiment have a rigid group such as dibenzothiophene or dibenzofuran, and therefore have excellent morphology, give stable film quality; and also have an excellent thermophysical property. In addition, the carbazole compounds can be used for a light-emitting material that emits blue to ultraviolet light.

Embodiment 2

Next, in this embodiment, a method of synthesizing the carbazole compound represented by the general formula (G1) below is described. A variety of reactions can be applied to the method of synthesizing the carbazole compound. For example, synthesis reactions described below enable the synthesis of the carbazole compound represented by the general formula (G1).

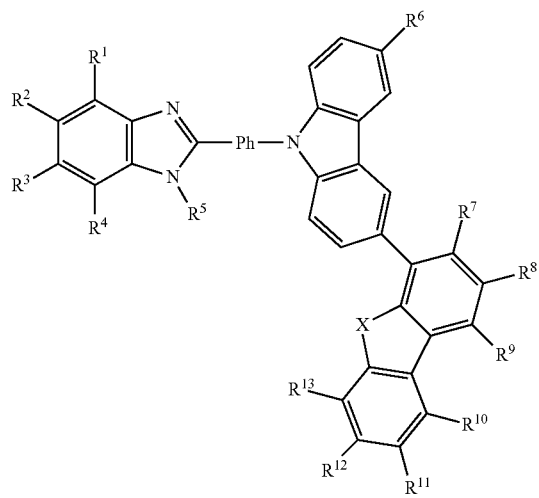

(G1)

First, a compound 1 having a halogen group or a triflate group at the 3-position of 9H-carbazole is coupled with a boronic acid compound (compound 2) of dibenzofuran (or dibenzothiophene), so that a 9H-carbazole derivative having a structure in which the 3-position of 9H-carbazole is bonded to the 4-position of dibenzofuran (or dibenzothiophene) (compound 3) can be obtained (reaction formula (A-1)).

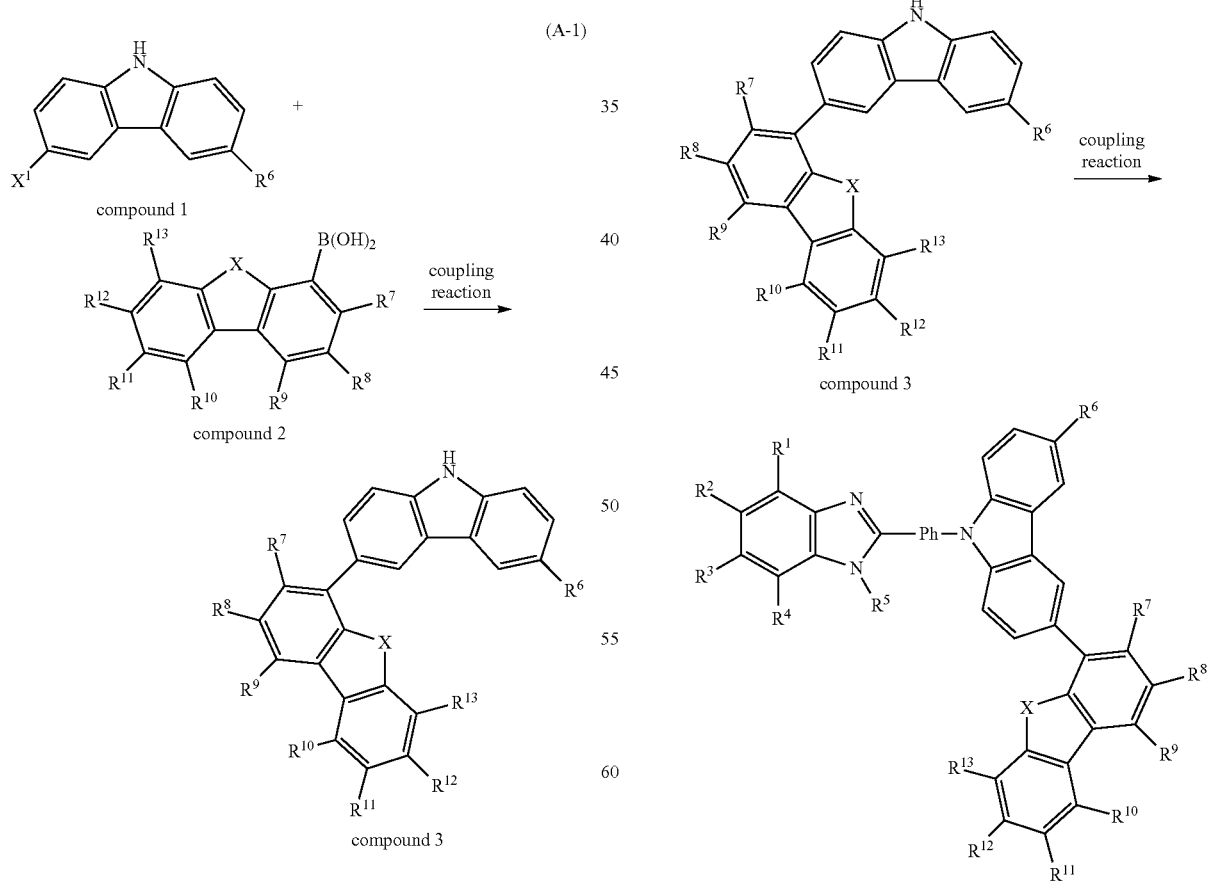

In the reaction formula (A-1), X represents oxygen or sulfur, $X^1$ represents a halogen group, a triflate group, or the like, and $R^6$ to $R^{13}$ separately represent hydrogen, an alkyl group having 1 to 4 carbon atoms, or an aryl group having 6 to 12 carbon atoms. The aryl group may have a substituent. Further, the compound 2 may be a boron compound in which boronic acid is protected with ethylene glycol or the like. As the coupling reaction in the reaction formula (A-1), a Suzuki-Miyaura coupling reaction using a palladium catalyst can be used.

Alternatively, for example, a Kumada coupling reaction using a Grignard reagent as substitute for the boronic acid compound in the compound 2, a Negishi coupling reaction using an organozinc compound as substitute for the boronic acid compound, or a Migita-Kosugi-Stille coupling using an organotin compound as substitute for the boronic acid compound may be performed.

Next, the obtained 9H-carbazole derivative (compound 3) is coupled with a halide of a benzimidazole derivative (compound 4), so that a compound (G1) which is the object of the synthesis can be obtained (reaction formula (A-2)).

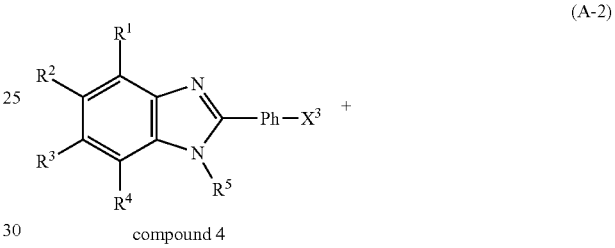

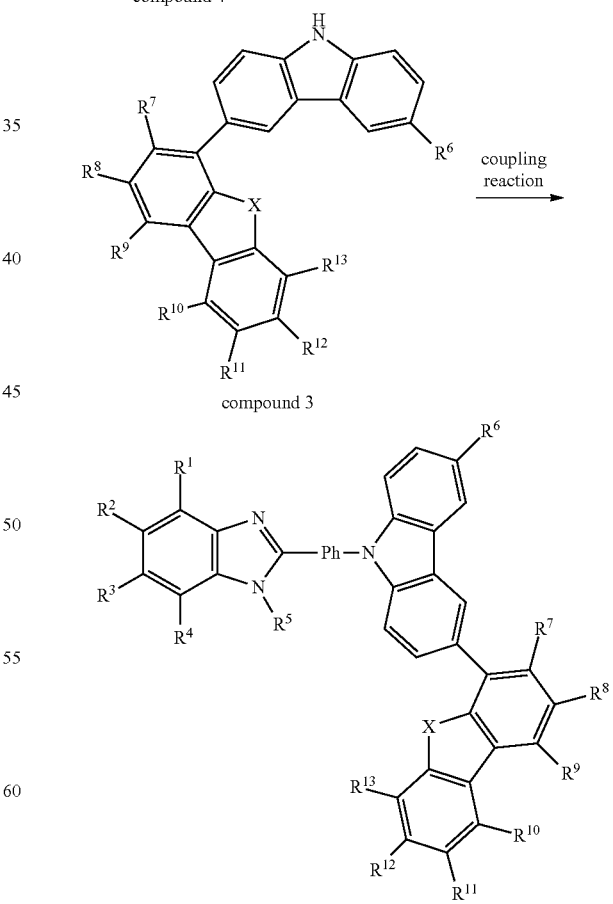

In the reaction formula (A-2), X represents oxygen or sulfur, $X^3$ represents a halogen group or the like, $R^1$ to $R^4$ separately represent hydrogen, an alkyl group having 1 to 4 carbon atoms, or a phenyl group, $R^5$ represents an aryl group having 6 to 12 carbon atoms, and $R^6$ to $R^{13}$ separately represent hydrogen, an alkyl group having 1 to 4 carbon atoms, or an aryl group having 6 to 12 carbon atoms. The aryl group may have a substituent. The coupling reaction in the reaction formula (A-2) can be performed by a Buchwald-Hartwig reaction using a palladium catalyst, an Ullmann reaction using copper or a copper compound, or the like.

As described above, the carbazole compounds described in Embodiment 1 can be synthesized.

Embodiment 3

In this embodiment, an example of the mode in which any of the carbazole compounds described in Embodiment 1 is used for an active layer of a vertical transistor (static induction transistor: SIT), which is a kind of an organic semiconductor element, will be described.

Figure 2:
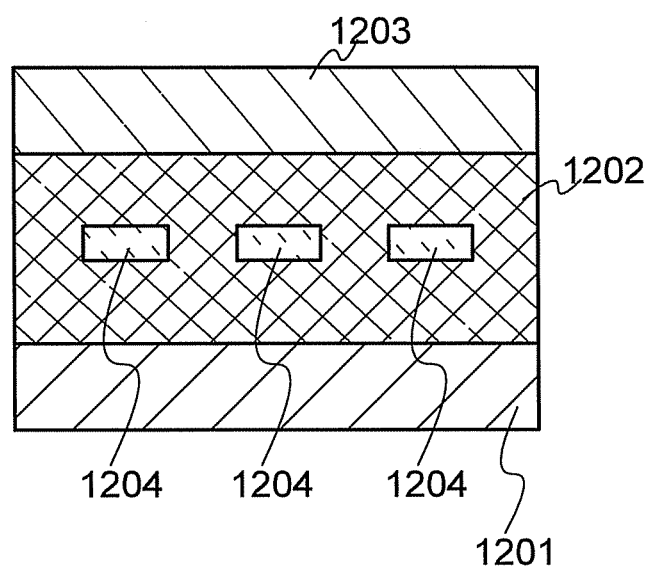
FIG. 2 is a conceptual diagram of an organic semiconductor element.

As illustrated in FIG. 2, the element has a structure in which a thin-film active layer 1202 containing any of the carbazole compounds described in Embodiment 1 is interposed between a source electrode 1201 and a drain electrode 1203, and a gate electrode 1204 is embedded in the active layer 1202. The gate electrode 1204 is electrically connected to a means for applying a gate voltage, and the source electrode 1201 and the drain electrode 1203 are electrically connected to a means for controlling a voltage between a source electrode and a drain electrode.

In such an element structure, when a voltage is applied between the source electrode and the drain electrode without applying a voltage to the gate electrode, a current flows (on state). Then, by application of a voltage to the gate electrode in that state, a depletion layer is formed in the periphery of the gate electrode 1204, and the current ceases flowing (off state). With such a mechanism, the element operates as a transistor.

Like a light-emitting element, a vertical transistor should contain a material that realizes both a high carrier-transport property and high quality film for an active layer; the carbazole compounds described in Embodiment 1 meet such a requirement and therefore can be suitably used.

Embodiment 4

In this embodiment, one mode of a light-emitting element using any of the carbazole compounds described in Embodiment 1 is described below with reference to FIG. 1A.

A light-emitting element of this embodiment includes a plurality of layers between a pair of electrodes. In this embodiment, the light-emitting element includes a first electrode 102, a second electrode 104, and a layer 103 containing an organic compound, which is provided between the first electrode 102 and the second electrode 104. Note that in this embodiment, the first electrode 102 functions as an anode and the second electrode 104 functions as a cathode. In other words, when a voltage is applied between the first electrode 102 and the second electrode 104 so that the voltage of the first electrode 102 is higher than that of the second electrode 104, light emission can be obtained.

The substrate 101 is used as a support of the light-emitting element. As the substrate 101, glass, plastic or the like can be used, for example. Note that a material other than glass or plastic can be used as far as it can function as a support of the light-emitting element.

For the first electrode 102, any of metals, alloys, electrically conductive compounds, and mixtures thereof which have a high work function (specifically, a work function of 4.0 eV or more) or the like is preferably used. Specifically, for example, indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like can be given. Films of these electrically conductive metal oxides are usually formed by sputtering but may be formed by application of a sol-gel method or the like. For example, indium oxide-zinc oxide (IZO) can be formed by a sputtering method using a target in which zinc oxide is added to indium oxide at 1 wt % to 20 wt %. Moreover, indium oxide containing tungsten oxide and zinc oxide (IWZO) can be formed by a sputtering method using a target in which tungsten oxide is added to indium oxide at 0.5 wt % to 5 wt % and zinc oxide is added to indium oxide at 0.1 wt % to 1 wt %. Besides, gold (Au), platinum (Pt), nickel (Ni), tungsten (W), chromium (Cr), molybdenum (Mo), iron (Fe), cobalt (Co), copper (Cu), palladium (Pd), graphene, nitrides of metal materials (e.g., titanium nitride), and the like can be given.

There is no particular limitation on a stacked structure of the layer 103 containing an organic compound. The layer 103 containing an organic compound can be formed by combining a layer that contains a substance having a high electron-transport property, a layer that contains a substance having a high hole-transport property, a layer that contains a substance having a high electron-injection property, a layer that contains a substance having a high hole-injection property, a layer that contains a bipolar substance (a substance having a high electron-transport and hole-transport property), and the like as appropriate. For example, the layer 103 containing an organic compound can be formed by combining a hole-injection layer, a hole-transport layer, a light-emitting layer, an electron-transport layer, an electron-injection layer, and the like as appropriate. In this embodiment, a structure in which the layer 103 containing an organic compound includes a hole-injection layer 111, a hole-transport layer 112, a light-emitting layer 113, and an electron-transport layer 114 stacked in this order over the first electrode 102 is described. Materials included in the layers are specifically given below.

The hole-injection layer 111 is a layer containing a substance having a high hole-injection property. Molybdenum oxide, vanadium oxide, ruthenium oxide, tungsten oxide, manganese oxide, or the like can be used. Alternatively, the hole-injection layer 111 can be foamed with a phthalocyanine-based compound such as phthalocyanine (abbreviation: $H_2Pc$) or copper phthalocyanine (abbreviation: CuPc), an aromatic amine compound such as 4,4'-bis[N-(4-diphenylaminophenyl)-N-phenylamino]biphenyl (abbreviation: DPAB) or N,N'-bis[4-[bis(3-methylphenyl)amino]phenyl]-N,N'-diphenyl-[1,1'-biphenyl]-4,4'-diamine (abbreviation: DNTPD), a high molecular compound such as poly(ethylenedioxythiophene)/poly(styrenesulfonic acid) (PEDOT/PSS), or the like.

Alternatively, a composite material in which a substance having a high hole-transport property contains a substance having an acceptor property can be used for the hole-injection layer 111. In this specification, the composite material refers to not a material in which two materials are simply mixed but a material in the state where charge transfer between the materials can be caused by a mixture of a plurality of materials. This charge transfer includes the charge transfer that is realized only when an electric field exists.

Note that the use of such a substance having a high hole-transport property which contains a substance having an acceptor property enables selection of a material used to form an electrode regardless of its work function. In other words, besides a material having a high work function, a material having a low work function can also be used for the first electrode 102. As the substance having an acceptor property, 7,7,8,8-tetracyano-2,3,5,6-tetrafluoroquinodimethane (abbreviation: $F_4$-TCNQ), chloranil, and the like can be given. In addition, transition metal oxides can be given. Oxides of the metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because their electron-accepting property is high. Among these, molybdenum oxide is especially preferable because it is stable in the air and its hygroscopic property is low and is easily treated.

As the substance having a high hole-transport property used for the composite material, any of a variety of compounds such as aromatic amine compounds, carbazole compounds, aromatic hydrocarbons, and high molecular compounds (e.g., oligomers, dendrimers, or polymers) can be used. Note that the organic compound used for the composite material is preferably an organic compound having a high hole-transport property. Specifically, a substance having a hole mobility of $10^{-6}$ cm$^2$/Vs or more is preferably used. Further, other than these substances, any substance that has a property of transporting more holes than electrons may be used. Organic compounds that can be used as the substance having a high hole-transport property in the composite material are specifically given below.

Examples of the aromatic amine compounds include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis[4-[bis(3-methylphenyl)amino]phenyl]-N,N'-diphenyl-[1,1'-biphenyl]-4,4'-diamine (abbreviation: DNTPD), 1,3,5-tris[N-(4-diphenylaminophenyl)-N-phenylamino]benzene (abbreviation: DPA3B), and the like.

Examples of the carbazole compounds that can be used for the composite material specifically include 3-[N-(9-phenyl-carbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Examples of the carbazole compounds that can be used for the composite material also include 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbons that can be used for the composite material include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides, pentacene, coronene, or the like can also be used. Thus, an aromatic hydrocarbon having 14 to 42 carbon atoms or more and having a hole mobility of $1\times10^{-6}$ cm$^2$/Vs is more preferably used.

Note that the aromatic hydrocarbons that can be used for the composite material may have a vinyl skeleton. Examples of the aromatic hydrocarbon having a vinyl group include 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Moreover, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), or poly[N,N'-bis(4-butylphenyl)-N,N'-bis(phenyl)benzidine] (abbreviation: poly-TPD) can also be used.

The carbazole compounds described in Embodiment 1 are also the aromatic hydrocarbon that can be used for the composite material.

The hole-transport layer 112 is a layer that contains a substance having a high hole-transport property. As the substance having a high hole-transport property, the substances given as the substances having a high hole-transport property which can be used for the above composite material can also be used. Note that a detailed explanation is omitted to avoid repetition. Refer to the explanation of the composite material.

Since the carbazole compound represented by the general formula (G1) described in Embodiment 1 has a bipolar transport property, the carbazole compound can be used also for the hole-transport layer 112. Also for a carrier-transport layer adjacent to a light-emitting layer containing an emission center substance that emits blue fluorescence or an emission center substance that emits green phosphorescence, the carbazole compound having a wide band gap can be suitably used without deactivating excitation energy of the emission center substance. Accordingly, a light-emitting element with high emission efficiency can be fabricated. It is needless to say that the carbazole compound can be used for a material included in a carrier-transport layer adjacent to a light-emitting layer containing an emission center substance that emits fluorescence at a longer wavelength than blue or phosphorescence at a longer wavelength than green or a material included in a carrier-transport layer adjacent to a light-emitting layer containing an emission center substance that emits fluorescence at a shorter wavelength than blue or phosphorescence at a shorter wavelength than green.

The light-emitting layer 113 is a layer containing a light-emitting substance. The light-emitting layer 113 may be formed with a film containing only a light-emitting substance or a film in which an emission center substance is dispersed into a host material.

There is no particular limitation on a material that can be used as the light-emitting substance or the emission center substance in the light-emitting layer 113, and light emitted from the material may be either fluorescence or phosphorescence. Examples of the above light-emitting substance or emission center substance include the following substances: fluorescent substances such as N,N'-bis[4-(9-phenyl-9H-fluoren-9-yl)phenyl]-N,N'-diphenyl-pyrene-1,6-diamine (abbreviation: 1,6-FLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl) triphenylamine (abbreviation: YGAPA), 4-(9H-carbazol-9- yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N'''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N''',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM); and phosphorescent substances such as bis[2-(3',5'-bistrifluoromethylphenyl)pyridinato-N,C$^{2'}$]iridium(III) picolinate (abbreviation: Ir(CF$_3$ppy)$_2$(pic)), bis[2-(4',6'-difluorophenyl)pyridinato-N,C$^{2'}$]iridium(III) acetylacetonate (abbreviation: FIracac), tris(2-phenylpyridinato)iridium(III) (abbreviation: Ir(ppy)$_3$), bis(2-phenylpyridinato)iridium(III) acetylacetonate (abbreviation: Ir(ppy)$_2$(acac)), tris(acetylacetonato)(monophenanthroline)terbium(III) (abbreviation: Tb(acac)$_3$(Phen)), bis(benzo[h]quinolinato)iridium(III) acetylacetonate (abbreviation: Ir(bzq)$_2$(acac)), bis(2,4-diphenyl-1,3-oxazolato-N,C$^{2'}$)iridium(III) acetylacetonate (abbreviation: Ir(dpo)$_2$(acac)), bis[2-(4'-perfluorophenylphenyl)pyridinato]iridium(III) acetylacetonate (abbreviation: Ir(p-PF-ph)$_2$(acac)), bis(2-phenylbenzothiazolato-N,C$^{2'}$)iridium(III) acetylacetonate (abbreviation: Ir(bt)$_2$(acac)), bis[2-(2'-benzo[4,5-α]thienyl)pyridinato-N,C$^{3'}$]iridium(III) (acetylacetonate) (abbreviation: Ir(btp)$_2$(acac)), bis(1-phenylisoquinolinato-N,C$^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(2,3,5-triphenylpyrazinato)iridium(III) (abbreviation: Ir(tppr)$_2$(acac)), 2,3,7,8,12,13,17,18-octaethyl-21H,23H-porphine platinum(II) (abbreviation: PtOEP), tris(1,3-diphenyl-1,3-propanedionato)(monophenanthroline)europium(III) (abbreviation: Eu(DBM)$_3$(Phen)), and tris[1-(2-thenyl)-3,3,3-trifluoroacetonato](monophenanthroline)europium(III) (abbreviation: Eu(TTA)$_3$(Phen)). Note that the carbazole compounds according to the present invention, typical examples of which include the carbazole compound represented by the general formula (G1) described in Embodiment 1, emit light in the blue to ultraviolet region, and therefore can also be used as an emission center substance.

The carbazole compound represented by the general formula (G1) described in Embodiment 1 has a wide band gap and has high triplet excitation energy (a large energy difference between a triplet excited state and a ground state), the carbazole compound can be suitably used for a host material, into which an emission center substance that emits blue fluorescence or an emission center substance that emits green phosphorescence is dispersed. It is needless to say that the carbazole compound can be used for a host material, into which an emission center substance that emits fluorescence at a longer wavelength than blue or phosphorescence at a longer wavelength than green or an emission center substance that emits fluorescence at a shorter wavelength than blue or phosphorescence at a shorter wavelength than green is dispersed. Since the carbazole compound has a wide band gap and thus high triplet excitation energy, the energy of carriers that are recombined in the host material can be effectively transferred to the emission center substance. Accordingly, a light-emitting element with high emission efficiency can be fabricated. Note that in the case where the carbazole derivative represented by the general formula (G1) described in Embodiment 1 is used for a host, an emission center substance is preferably selected from, but not limited to, substances having a narrower band gap or lower triplet excitation energy than the carbazole compound.

When the carbazole compound represented by the general formula (G1) is not used as the above host material, any of the following substances can be used for the host material: metal complex such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: BPhen), bathocuproine (abbreviation: BCP), and 9-[4-(5-phenyl-1,3,4-oxadiazol-2-yl)phenyl]-9H-carbazole (abbreviation: CO11); and aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4,4'-bis[N-(spino-9,9'-bifluoren-2-yl)-N-phenylamino]biphenyl (abbreviation: BSPB). In addition, condensed polycyclic aromatic compounds such as anthracene derivatives, phenanthrene derivatives, pyrene derivatives, chrysene derivatives, and dibenzo[g,p]chrysene derivatives can be given, and specific examples are 9,10- diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenylchrysene, N,N,N',N',N'',N'',N''',N'''-octaphenyldibenzo[g,p]chrysene-2,7,10,15-tetramine (abbreviation: DBC1), 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3''-(benzene-1,3,5-triyl)tripyrene (abbreviation: TPB3), and the like. Other than these, known materials can be given.

Note that the light-emitting layer 113 can also be a stack of two or more layers. For example, in the case where the light-emitting layer 113 is formed by stacking a first light-emitting layer and a second light-emitting layer in that order over the hole-transport layer, for example, a substance having a hole-transport property is used for the host material of the first light-emitting layer and a substance having an electron-transport property is used for the host material of the second light-emitting layer.

In the case where the light-emitting layer having the above-described structure includes a plurality of materials, co-evaporation by a vacuum evaporation method can be used, or alternatively an inkjet method, a spin coating method, a dip coating method, or the like with a solution of the materials can be used.

The electron-transport layer 114 is a layer containing a substance having a high electron-transport property: for example, a layer containing a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq). Alternatively, a metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), or the like can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances mentioned here mainly have an electron mobility of $10^{-6}$ cm$^2$/Vs or more. Note that other than these substances, any substance that has a property of transporting more electrons than holes may be used.

Since the carbazole derivative represented by the general formula (G1) described in Embodiment 1 has a bipolar transport property, the carbazole compound can be used also for the electron-transport layer 114. Also for a carrier-transport layer adjacent to a light-emitting layer containing an emission center substance that emits blue fluorescence or an emission center substance that emits green phosphorescence, the carbazole compound having a wide band gap can be suitably used without deactivating excitation energy of the emission center substance. Accordingly, a light-emitting element with high emission efficiency can be fabricated. It is needless to say that the carbazole compound can be used for a material included in a carrier-transport layer adjacent to a light-emitting layer containing an emission center substance that emits fluorescence at a longer wavelength than blue or phosphorescence at a longer wavelength than green or a material included in a carrier-transport layer adjacent to a light-emitting layer containing an emission center substance that emits fluorescence at a shorter wavelength than blue or phosphorescence at a shorter wavelength than green.

Furthermore, the electron-transport layer is not limited to a single layer and may be a stack of two or more layers containing any of the above substances.

Between the electron-transport layer and the light-emitting layer, a layer that controls transport of electron carriers may be provided. This is a layer formed by addition of a small amount of a substance having a high electron-trapping property to a material having a high electron-transport property as described above, and capable of adjusting carrier balance by suppressing transport of electron carriers. Such a structure is very effective in preventing a problem (such as a reduction in element lifetime) caused when electrons pass through the light-emitting layer.

In addition, an electron-injection layer may be provided in contact with the second electrode 104 between the electron-transport layer and the second electrode 104. For the electron-injection layer, an alkali metal, an alkaline earth metal, or a compound thereof such as lithium fluoride (LiF), cesium fluoride (CsF), or calcium fluoride (CaF$_2$) can be used. For example, a layer that is formed with a substance having an electron-transport property and contains an alkali metal, an alkaline earth metal, or a compound thereof, such as an Alq layer containing magnesium (Mg), can be used. Note that electron injection from the second electrode 104 is efficiently performed with the use of a layer that is formed with a substance having an electron-transport property and contains an alkali metal or an alkaline earth metal as the electron-injection layer, which is preferable.

For the second electrode 104, any of metals, alloys, electrically conductive compounds, and mixtures thereof which have a low work function (specifically, a work function of 3.8 eV or less) or the like can be used. Specific examples of such a cathode material include elements that belong to Groups 1 and 2 in the periodic table, i.e., alkali metals such as lithium (Li) and cesium (Cs), and alkaline earth metals such as magnesium (Mg), calcium (Ca), and strontium (Sr), alloys thereof (e.g., MgAg or AlLi), rare earth metals such as europium (Eu) and ytterbium (Yb), alloys thereof, and the like. However, when the electron-injection layer is provided between the second electrode 104 and the electron-transport layer, for the second electrode 104, any of a variety of conductive materials such as Al, Ag, ITO, or indium oxide-tin oxide containing silicon or silicon oxide can be used regardless of the work function. Films of these electrically conductive materials can be found by a sputtering method, an inkjet method, a spin coating method, or the like.

Further, any of a variety of methods can be used to form the layer 103 containing an organic compound regardless whether it is a dry process or a wet process. For example, a vacuum evaporation method, an inkjet method, a spin coating method or the like may be used. Different formation methods may be used for the electrodes or the layers.

In addition, the electrode may be formed by a wet method using a sol-gel method, or by a wet method using paste of a metal material. Alternatively, the electrode may be formed by a dry method such as a sputtering method or a vacuum evaporation method.

In the light-emitting element having the above-described structure, a current flows due to a potential difference between the first electrode 102 and the second electrode 104, and a hole and an electron recombine in the light-emitting layer 113 which contains a substance having a high light-emitting property, so that light is emitted. That is, a light-emitting region is formed in the light-emitting layer 113.

Light emission is extracted out through one or both of the first electrode 102 and the second electrode 104. Therefore, one or both of the first electrode 102 and the second electrode 104 are light-transmitting electrodes. In the case where only the first electrode 102 is a light-transmitting electrode, light emission is extracted from the substrate side through the first electrode 102. In the case where only the second electrode 104 is a light-transmitting electrode, light emission is extracted from the side opposite to the substrate side through the second electrode 104. In the case where each of the first electrode 102 and the second electrode 104 is a light-transmitting electrode, light emission is extracted from both the substrate side and the side opposite to the substrate through the first electrode 102 and the second electrode 104.

The structure of the layers provided between the first electrode 102 and the second electrode 104 is not limited to the above-described structure. Preferably, a light-emitting region where holes and electrons recombine is positioned away from the first electrode 102 and the second electrode 104 so that quenching due to the proximity of the light-emitting region and a metal used for electrodes and carrier-injection layers can be prevented. The order of stacking the layers is not limited to the above structure and may be the following order obtained by reversing the order shown in FIG. 1A: the second electrode, the electron-injection layer, the electron-transport layer, the light-emitting layer, the hole-transport layer, the hole-injection layer, and the first electrode from the substrate side.

Further, in order that transfer of energy from an exciton generated in the light-emitting layer can be suppressed, preferably, the hole-transport layer and the electron-transport layer which are in direct contact with the light-emitting layer, particularly a carrier-transport layer in contact with a side closer to the light-emitting region in the light-emitting layer 113 is formed with a substance having a larger band gap than the light-emitting substance of the light-emitting layer or the emission center substance included in the light-emitting layer.

In the light-emitting element of this embodiment, since any of the carbazole compounds described in Embodiment 1 having a large band gap is used for the host material and/or for the electron-transport layer, efficient light emission is possible even with the emission center substance that has a large band gap and emits blue fluorescence; thus, a light-emitting element with high emission efficiency can be provided. Accordingly, a light-emitting element having lower power consumption can be provided. In addition, the host material or a material included in the carrier-transport layer does not easily emit light; accordingly, a light-emitting element capable of light emission with high color purity can be provided. Further, the carbazole compounds described in Embodiment 1 have an excellent carrier-transport property; accordingly, a light-emitting element having low driving voltage can be provided.

In this embodiment, the light-emitting element is formed over a substrate formed of glass, plastic, or the like. With a plurality of such light-emitting elements over one substrate, a passive matrix light-emitting device can be fabricated. In addition, for example, a light-emitting element may be formed over an electrode electrically connected to a thin film transistor (TFT) which is formed over a substrate formed of glass, plastic, or the like; thus, an active matrix light-emitting device in which the TFT controls the drive of the light-emitting element can be fabricated. Note that there is no particular limitation on the structure of the TFT, which may be a staggered TFT or an inverted staggered TFT. In addition, crystallinity of a semiconductor used for the TFT is not particularly limited either; an amorphous semiconductor or a crystalline semiconductor may be used. In addition, a driver circuit formed in a TFT substrate may be formed with an n-type TFT and a p-type TFT, or with either an n-type TFT or a p-type TFT.

Embodiment 5

In this embodiment, one mode of a light-emitting element (hereinafter, also referred to as a stacked-type element) having a structure in which a plurality of light-emitting units is stacked is described with reference to FIG. 1B. This light-emitting element is a light-emitting element including a plurality of light-emitting units between a first electrode and a second electrode. Each light-emitting unit can have the same structure as the layer 103 containing an organic compound which is described in Embodiment 4. In other words, it can be said that the light-emitting element described in Embodiment 4 is a light-emitting element having one light-emitting unit and the light-emitting element in this embodiment is a light-emitting element having a plurality of light-emitting units.

Figure 1B:
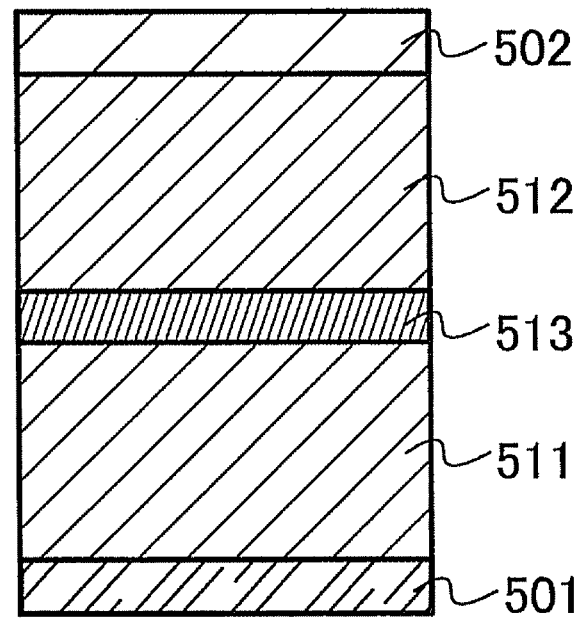

In FIG. 1B, a first light-emitting unit 511 and a second light-emitting unit 512 are stacked between a first electrode 501 and a second electrode 502, and a charge generation layer 513 is provided between the first light-emitting unit 511 and the second light-emitting unit 512. The first electrode 501 and the second electrode 502 correspond, respectively, to the first electrode 102 and the second electrode 104 according to Embodiment 4, and materials described in Embodiment 4 can be used. Further, the structures of the first light-emitting unit 511 and the second light-emitting unit 512 may be the same or different.

The charge generation layer 513 contains a composite material of an organic compound and a metal oxide. This composite material of an organic compound and a metal oxide is the composite material described in Embodiment 4, and contains an organic compound and a metal oxide such as vanadium oxide, molybdenum oxide, or tungsten oxide. As the organic compound, any of a variety of compounds such as aromatic amine compounds, carbazole compounds, aromatic hydrocarbons, and high molecular compounds (oligomers, dendrimers, polymers, or the like) can be used. Note that as the organic compound, the one having a hole mobility of $10^{-6}$ cm$^2$/Vs or more as an organic compound having a hole-transport property is preferably used. Further, other than these substances, any substance that has a property of transporting more holes than electrons may be used. Since a composite of an organic compound and a metal oxide is excellent in carrier-injection property and carrier-transport property, low voltage driving and low current driving can be realized.

The charge generation layer 513 may be formed in such a way that a layer containing the composite material of an organic compound and a metal oxide is combined with a layer containing another material, for example, with a layer that contains a compound selected from substances having an electron-donating property and a compound having a high electron-transport property. The charge generation layer 513 may be formed in such a way that a layer containing the composite material of an organic compound and a metal oxide is combined with a transparent conductive film.

The charge generation layer 513 interposed between the first light-emitting unit 511 and the second light-emitting unit 512 may have any structure as far as electrons can be injected to a light-emitting unit on one side and holes can be injected to a light-emitting unit on the other side when a voltage is applied between the first electrode 501 and the second electrode 502. For example, in FIG. 1B, any layer can be used as the charge generation layer 513 as far as the layer injects electrons into the first light-emitting unit 511 and holes into the second light-emitting unit 512 when a voltage is applied such that the voltage of the first electrode is higher than that of the second electrode.

Although the light-emitting element having two light-emitting units is described in this embodiment, the present invention can be similarly applied to a light-emitting element in which three or more light-emitting units are stacked. By arrangement of a plurality of light-emitting units, which are partitioned by the charge-generation layer between a pair of electrodes, as in the light-emitting element of this embodiment, light emission in a high luminance region can be realized with current density kept low, thus light-emitting having a long lifetime can be realized. Further, in application to lighting devices, since a voltage drop due to resistance of an electrode material can be reduced, light emission in a large area is possible. Moreover, a light-emitting device having low driving voltage and having lower power consumption can be realized.

By making emission colors of the light-emitting units different from each other, light emission with a desired color can be obtained from the light-emitting element as a whole. For example, in a light-emitting element including two light-emitting units, the emission colors of the first light-emitting unit and the second light-emitting unit are made complementary, so that the light-emitting element which emits white light as the whole element can be obtained. Note that the term "complementary" means color relationship in which an achromatic color is obtained when colors are mixed. That is, a mixture of light emissions with complementary colors gives white light emission. The same can be applied to a light-emitting element including three light-emitting units. For example, the light-emitting element as a whole can emit white light when the emission color of the first light-emitting unit is red, the emission color of the second light-emitting unit is green, and the emission color of the third light-emitting unit is blue.

Since the light-emitting element of this embodiment includes any of the carbazole compounds described in Embodiment 1, the light-emitting element can be a light-emitting element that has high emission efficiency and low driving voltage. In addition, since light emission with high color purity which originates from the emission center substance can be obtained from the light-emitting unit including the carbazole compound, color adjustment of the light-emitting element as a whole is easy.

Note that this embodiment can be combined with any of the other embodiments as appropriate.

Embodiment 6

In this embodiment, a light-emitting device including a light-emitting element including any of the carbazole compounds described in Embodiment 1 is described.

Figure 3A:
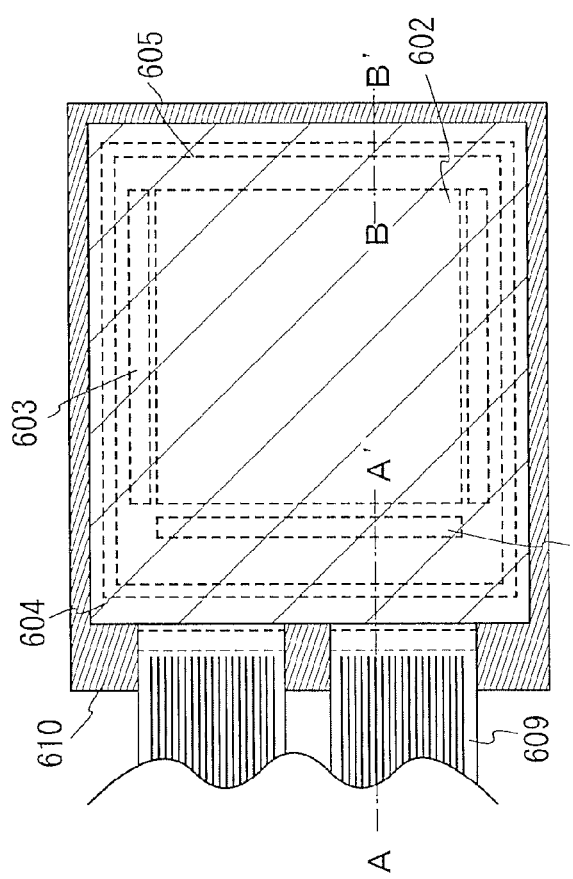
FIGS. 3A and 3B are conceptual diagrams of an active matrix light-emitting device.
Figure 3B:
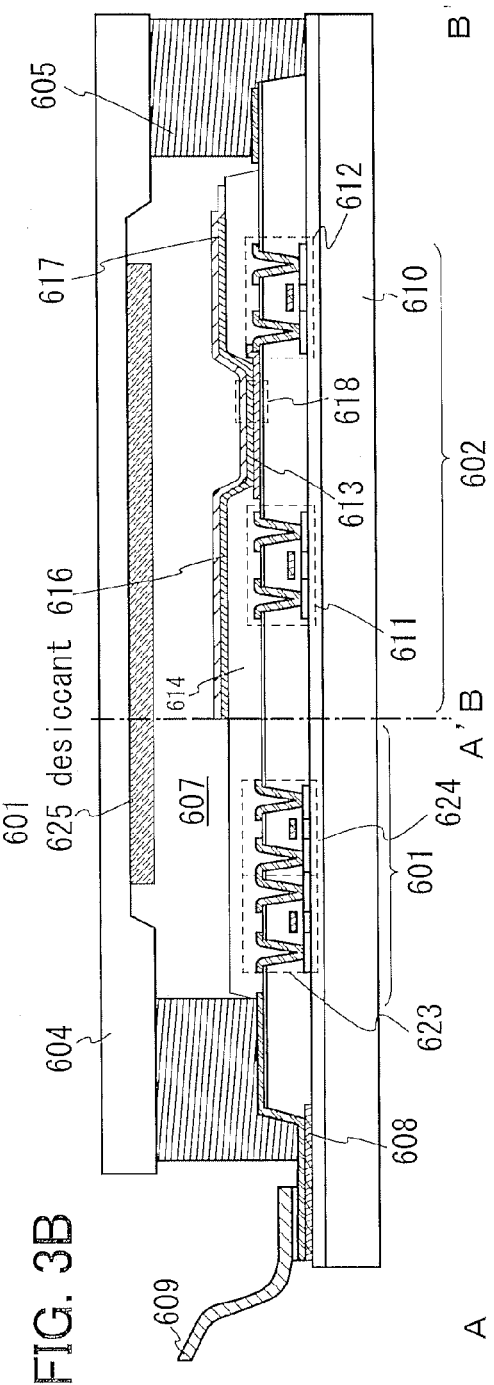

In this embodiment, an example of the light-emitting device fabricated using a light-emitting element including any of the carbazole compounds described in Embodiment 1 is described with reference to FIGS. 3A and 3B. Note that FIG. 3A is a top view illustrating the light-emitting device and FIG. 3B is a cross-sectional view of FIG. 3A taken along lines A-A' and B-B'. This light-emitting device includes a driver circuit portion (source driver circuit) 601, a pixel portion 602, and a driver circuit portion (gate driver circuit) 603, which are to control light emission of the light-emitting element and illustrated with dotted lines. Moreover, a reference numeral 604 denotes a sealing substrate; 605, a sealing material; and 607, a space surrounded by the sealing material 605.

Reference numeral 608 denotes a wiring for transmitting signals to be inputted into the source driver circuit 601 and the gate driver circuit 603 and receiving signals such as a video signal, a clock signal, a start signal, and a reset signal from an FPC (flexible printed circuit) 609 serving as an external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure is described with reference to FIG. 3B. The driver circuit portion and the pixel portion are formed over an element substrate 610; the source driver circuit 601, which is a driver circuit portion, and one of the pixels in the pixel portion 602 are illustrated here As the source driver circuit 601, a CMOS circuit in which an n-channel TFT 623 and a p-channel TFT 624 are combined is formed. In addition, the driver circuit may be formed with any of a variety of circuits such as a CMOS circuit, a PMOS circuit, or an NMOS circuit. Although a driver integrated type in which the driver circuit is formed over the substrate is illustrated in this embodiment, the driver circuit may not necessarily be formed over the substrate, and the driver circuit can be formed outside, not over the substrate.

The pixel portion 602 includes a plurality of pixels including a switching TFT 611, a current controlling TFT 612, and a first electrode 613 electrically connected to a drain of the current controlling TFT. Note that to cover an end portion of the first electrode 613, an insulator 614 is formed, for which a positive type photosensitive acrylic resin film is used here.

In order to improve coverage, the insulator 614 is formed to have a curved surface with curvature at its upper or lower end portion. For example, in the case where positive photosensitive acrylic is used for a material of the insulator 614, only the upper end portion of the insulator 614 preferably has a curved surface with a curvature radius (0.2 μm to 3 μm). As the insulator 614, either a negative type that becomes insoluble in an etchant by irradiation with light or a positive type that becomes soluble in an etchant by irradiation with light can be used.

A layer 616 containing an organic compound and a second electrode 617 are formed over the first electrode 613. Here, as a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack of a titanium nitride film and a film containing aluminum as its main component, a stack of three layers of a titanium nitride film, a film containing aluminum as its main component, and a titanium nitride film, or the like can be used. Note that when the stacked structure is used, the first electrode 613 has low resistance as a wiring, forms a favorable ohmic contact, and can function as an anode.

In addition, the layer 616 containing an organic compound is formed by any of a variety of methods such as an evaporation method using a shadow mask, an inkjet method, and a spin coating method. The layer 616 containing an organic compound contains any of the carbazole compounds described in Embodiment 1. Further, another material included in the layer 616 containing an organic compound may be a low molecular compound or a high molecular compound (which may be an oligomer and a dendrimer).

As a material used for the second electrode 617, which is formed over the layer 616 containing an organic compound and functions as a cathode, a material having a low work function (e.g., Al, Mg, Li, Ca, or an alloy or compound thereof, such as MgAg, MgIn, or AlLi) is preferably used. In the case where light generated in the layer 616 containing an organic compound passes through the second electrode 617, a stack of a thin metal film and a transparent conductive film (e.g., ITO, indium oxide containing zinc oxide at 2 wt % to 20 wt %, indium tin oxide containing silicon, or zinc oxide (ZnO)) is preferably used for the second electrode 617.

Note that the light-emitting element is formed with the first electrode 613, the layer 616 containing an organic compound, and the second electrode 617. The light-emitting element has any of the structures described in Embodiments 4 and 5. In the light-emitting device of this embodiment, the pixel portion, which includes a plurality of light-emitting elements, may include both the light-emitting element with any of the structures described in Embodiments 4 and 5 and a light-emitting element with a structure other than those.

Further, the sealing substrate 604 is attached to the element substrate 610 with the sealing material 605, so that a light-emitting element 618 is provided in the space 607 surrounded by the element substrate 610, the sealing substrate 604, and the sealing material 605. The space 607 may be filled with filler, and may be filled with an inert gas (such as nitrogen or argon), or the sealing material 605.

Note that an epoxy based resin is preferably used for the sealing material 605. It is desirable that such a material do not transmit moisture or oxygen as much as possible. As a material for the sealing substrate 604, a plastic substrate formed of FRP (fiberglass-reinforced plastics), PVF (polyvinyl fluoride), polyester, acrylic, or the like can be used besides a glass substrate or a quartz substrate.

As described above, the light-emitting device fabricated using the light-emitting element containing any of the carbazole compounds described in Embodiment 1 can be obtained.

The light-emitting element containing any of the carbazole compounds described in Embodiment 1 is used in the light-emitting device in this embodiment, and thus a light-emitting device having favorable characteristics can be obtained. Specifically, the carbazole compounds described in Embodiment 1 have a large band gap and high triplet excitation energy and can suppress energy transfer from a light-emitting substance; accordingly, a light-emitting element having high emission efficiency can be provided, so that a light-emitting device having reduced power consumption can be provided. In addition, a light-emitting element having low driving voltage can be provided, so that a light-emitting device having low driving voltage can be provided.

Figure 4A:
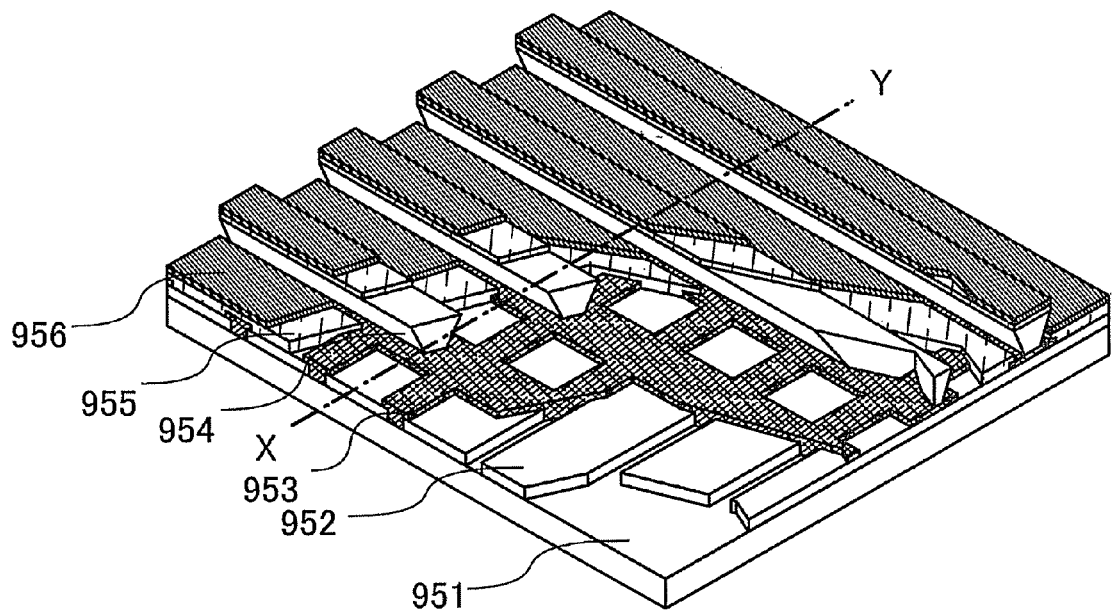
FIGS. 4A and 4B are conceptual diagrams of a passive matrix light-emitting device.
Figure 4B:
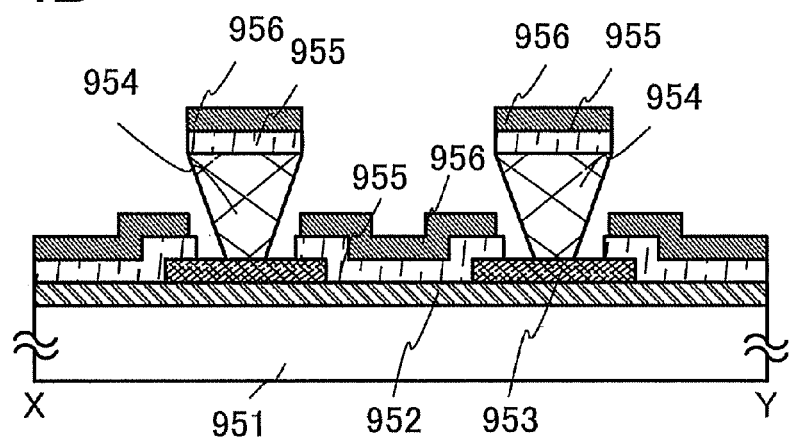

Although an active matrix light-emitting device is thus described above, a passive matrix light-emitting device is described below. FIGS. 4A and 4B illustrate a passive matrix light-emitting device fabricated according to the present invention. FIG. 4A is a perspective view of the light-emitting device, and FIG. 4B is a cross-sectional view taken along line X-Y in FIG. 4A. In FIGS. 4A and 4B, over a substrate 951, a layer 955 containing an organic compound is provided between an electrode 952 and an electrode 956. An end portion of the electrode 952 is covered with an insulating layer 953. In addition, a partition layer 954 is provided over the insulating layer 953. The sidewalls of the partition layer 954 are aslope such that the distance between both sidewalls is gradually narrowed toward the surface of the substrate. In other words, a cross section taken along the direction of the short side of the partition wall layer 954 is trapezoidal, and the lower side (a side which is in the same direction as a plane direction of the insulating layer 953 and in contact with the insulating layer 953) is shorter than the upper side (a side which is in the same direction as the plane direction of the insulating layer 953 and not in contact with the insulating layer 953). The partition layer 954 thus provided can prevent a defect in the light-emitting element due to static charge or the like. The passive matrix light-emitting device can also be driven with low power consumption by including the light-emitting element according to Embodiment 4 or 5 which contains any of the carbazole compounds described in Embodiment 1 and is capable of operating at low voltage. In addition, the light-emitting device can be driven with low power consumption by including the light-emitting element according to Embodiment 4 or 5 which contains any of the carbazole compounds described in Embodiment 1 and therefore has high emission efficiency.

Since many minute light-emitting elements arranged in a matrix in the light-emitting device described above can each be controlled, the light-emitting device can be suitably used as a display device for displaying images.

Embodiment 7

In this embodiment, electronic devices each including the light-emitting element described in Embodiment 4 or 5 are described. The light-emitting element described in Embodiment 4 or 5 has reduced power consumption since it includes any of the carbazole compounds described in Embodiment 1; accordingly, the electronic devices described in this embodiment can be electronic devices each including a display portion having reduced power consumption. In addition, they can be electronic devices having low driving voltage since the light-emitting element described in Embodiment 4 or 5 is a light-emitting element having low driving voltage.

Examples of the electronic devices to which the above light-emitting element is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices are described below.

Figure 5A:
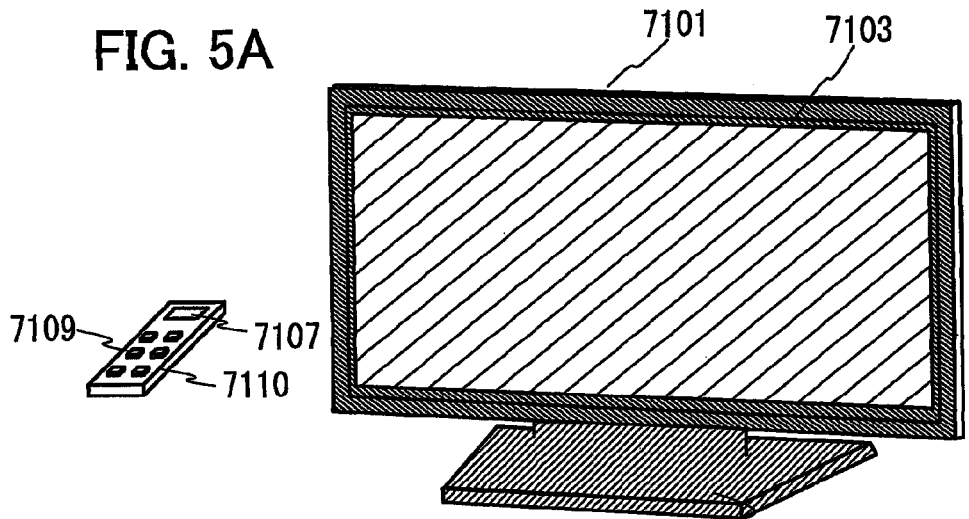
FIGS. 5A to 5D each illustrate an electronic device.

FIG. 5A illustrates an example of a television device. In the television device, a display portion 7103 is incorporated in a housing 7101. In addition, here, the housing 7101 is supported by a stand 7105. The display portion 7103 enables display of images and includes light-emitting elements which are the same as that described in Embodiment 4 or 5 and arranged in a matrix. Since each light-emitting element includes any of the carbazole compounds described in Embodiment 1, the light-emitting elements can be light-emitting elements having high emission efficiency, or can be light-emitting elements having low driving voltage. Accordingly, the television device that has the display portion 7103 including the light-emitting elements can be a television device having reduced power consumption or can be a television device having low driving voltage.

The television device can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the receiver, general television broadcasting can be received. Furthermore, when the television device is connected to a communication network by wired or wireless connection via the modem, one-way (from a transmitter to a receiver) or two-way (between a transmitter and a receiver, between receivers, or the like) data communication can be performed.

Figure 5B:
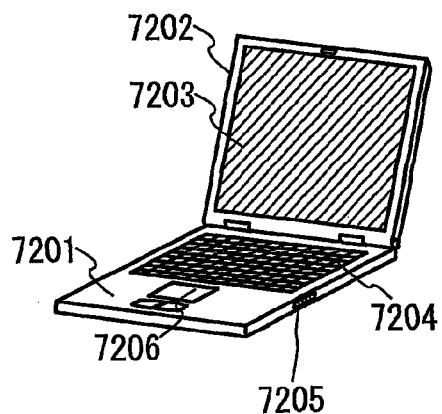

FIG. 5B illustrates a computer having a main body 7201, a housing 7202, a display portion 7203, a keyboard 7204, an external connecting port 7205, a pointing device 7206, and the like. Note that this computer is manufactured by using light-emitting elements arranged in a matrix in the display portion 7203, which are the same as that described in Embodiment 4 or 5. Since each light-emitting element includes any of the carbazole compounds described in Embodiment 1, the light-emitting elements can be light-emitting elements having high emission efficiency, or can be light-emitting elements having low driving voltage. Accordingly, the computer that has the display portion 7203 including the light-emitting elements can be a computer having reduced power consumption or can be a computer having low driving voltage.

Figure 5C:
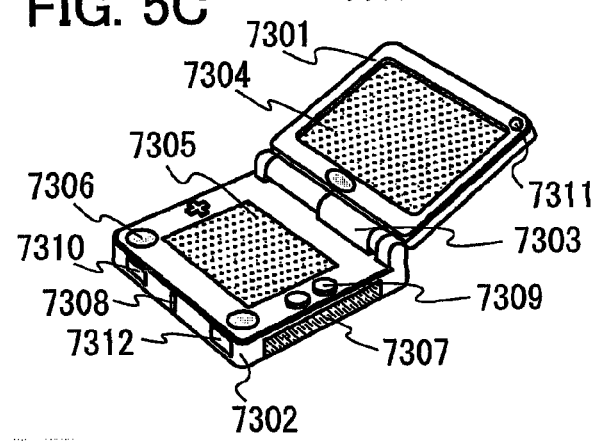

FIG. 5C illustrates a portable game machine having two housings, a housing 7301 and a housing 7302, which are connected with a joint portion 7303 so that the portable game machine can be opened or folded. A display portion 7304 including light-emitting elements which are the same as that described in Embodiment 4 or 5 and arranged in a matrix is incorporated in the housing 7301, and a display portion 7305 is incorporated in the housing 7302. In addition, the portable game machine illustrated in FIG. 5C includes a speaker portion 7306, a recording medium insertion portion 7307, an LED lamp 7308, an input unit (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable games machine is not limited to the above as far as the display portion including light-emitting elements which are the same as that described in Embodiment 4 or 5 and arranged in a matrix is used as at least either the display portion 7304 or the display portion 7305, or both, and the structure can include other accessories as appropriate. The portable game machine illustrated in FIG. 5C has a function of reading out a program or data stored in a storage medium to display it on the display portion, and a function of sharing information with another portable game machine by wireless communication. The portable game machine illustrated in FIG. 5C can have a variety of functions without limitation to the above. The portable game machine including the above-described display portion 7304 can be a portable game machine having reduced power consumption because the light-emitting elements used in the display portion 7304 have high emission efficiency by including any of the carbazole compounds described in Embodiment 1. The portable game machine can also be a portable game machine having low driving voltage because the light-emitting elements used in the display portion 7304 has low driving voltage by including any of the carbazole compounds described in Embodiment 1.

Figure 5D:
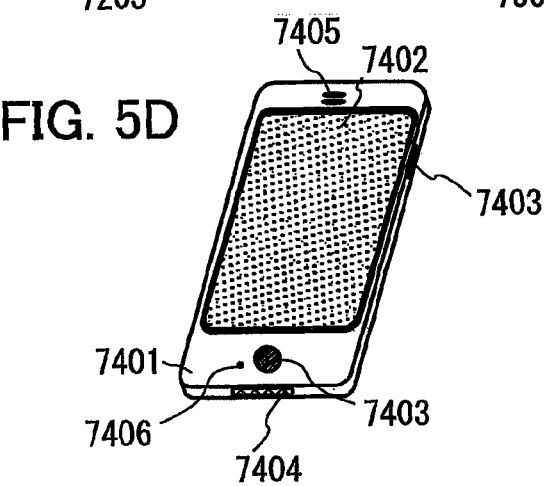

FIG. 5D illustrates an example of a cellular phone. The cellular phone 7400 is provided with operation buttons 7403, an external connection port 7404, a speaker 7405, a microphone 7406, and the like, in addition to a display portion 7402 incorporated in a housing 7401. Note that the cellular phone 7400 has the display portion 7402 including light-emitting elements which are the same as that described in Embodiment 4 or 5 and arranged in a matrix. Since each light-emitting element includes any of the carbazole compounds described in Embodiment 1, the light-emitting elements can be light-emitting elements having high emission efficiency, or can be light-emitting elements having low driving voltage. Accordingly, the cellular phone that has the display portion 7402 including the light-emitting elements can be a cellular phone having reduced power consumption or can be a cellular phone having low driving voltage.

When the display portion 7402 of the cellular phone illustrated in FIG. 5D is touched with a finger or the like, data can be input into the cellular phone. In this case, operations such as making a call and creating e-mail can be performed by touch on the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are mixed.

For example, in the case of making a call or creating e-mail, a text input mode mainly for inputting text is selected for the display portion 7402 so that text displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone, display on the screen of the display portion 7402 can be automatically changed by determining the orientation of the cellular phone (whether the cellular phone is placed horizontally or vertically for a landscape mode or a portrait mode).

The screen modes are switched by touch on the display portion 7402 or operation with the operation buttons 7403 of the housing 7401. Alternatively, the screen modes can be switched depending on the kinds of images displayed on the display portion 7402. For example, when a signal for an image displayed on the display portion is data of moving images, the screen mode is switched to the display mode. When the signal is text data, the screen mode is switched to the input mode.

Moreover, in the input mode, if a signal detected by an optical sensor in the display portion 7402 is detected and the input by touch on the display portion 7402 is not performed during a certain period, the screen mode may be controlled so as to be switched from the input mode to the display mode.

The display portion 7402 can function as an image sensor. For example, an image of a palm print, a fingerprint, or the like is taken by touch on the display portion 7402 with the palm or the finger, so that personal authentication can be performed. Furthermore, by use of a backlight or a sensing light source that emits a near-infrared light for the display portion, an image of a finger vein, a palm vein, or the like can also be taken.

Note that the structure described in this embodiment can be combined with any of the structures described in Embodiments 1 to 3 as appropriate.

As described above, the application range of the light-emitting device having the light-emitting element according to Embodiment 4 or 5 which includes any of the carbazole compounds described in Embodiment 1 is wide so that this light-emitting device can be applied to electronic devices in a variety of fields. By use of any of the carbazole compounds described in Embodiment 1, an electronic device having reduced power consumption or an electronic device having low driving voltage can be obtained.

The light-emitting element described in Embodiment 4 or 5 can also be used for a lighting device. One mode of application of the light-emitting element described in Embodiment 4 or 5 to a lighting device is described with reference to FIG. 6. Note that the lighting device includes the light-emitting element described in Embodiment 4 or 5 as a light irradiation unit and at least includes an input-output terminal portion that supplies a current to the light-emitting element. Further, the light-emitting element is preferably shielded from the outside atmosphere by sealing.

Figure 6:
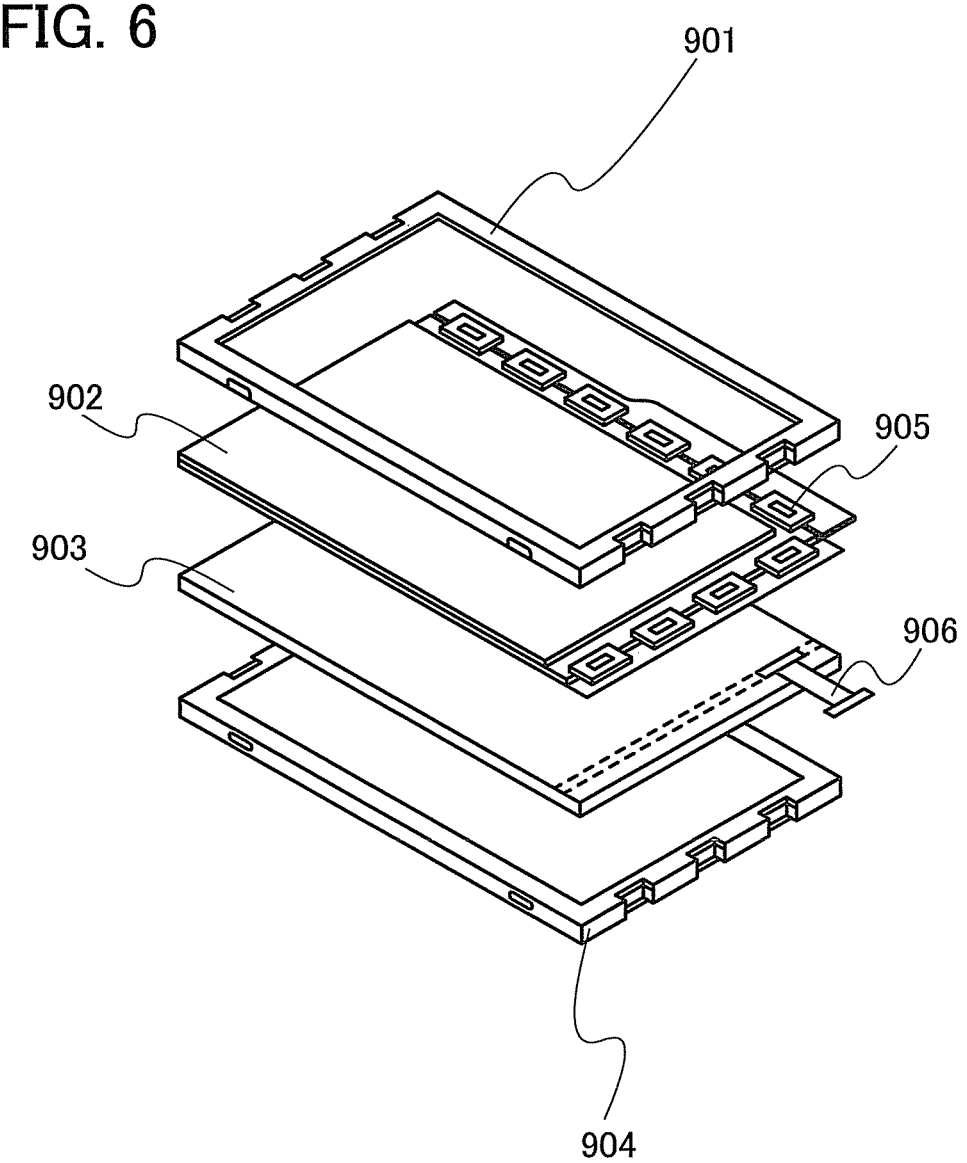
FIG. 6 illustrates an electronic device.

FIG. 6 illustrates an example of a liquid crystal display device using the light-emitting element described in Embodiment 4 or 5 for a backlight. The liquid crystal display device illustrated in FIG. 6 includes a housing 901, a liquid crystal layer 902, a backlight 903, and a housing 904. The liquid crystal layer 902 is connected to a driver IC 905. The light-emitting element described in Embodiment 4 or 5 is used in the backlight 903, to which a current is supplied through a terminal 906.

The light-emitting element described in Embodiment 4 or 5 is used for the backlight of the liquid crystal display device, and thus a backlight having reduced power consumption can be obtained. In addition, use of the light-emitting element described in Embodiment 4 or 5 enables manufacture of a planar-emission lighting device and further a larger-area planar-emission lighting device; therefore, the backlight can be a larger-area backlight, and the liquid crystal display device can also be a larger-area device. Furthermore, the backlight using the light-emitting element described in Embodiment 4 or 5 can be thinner than a conventional one; accordingly, the display device can also be thinner.

Figure 7:
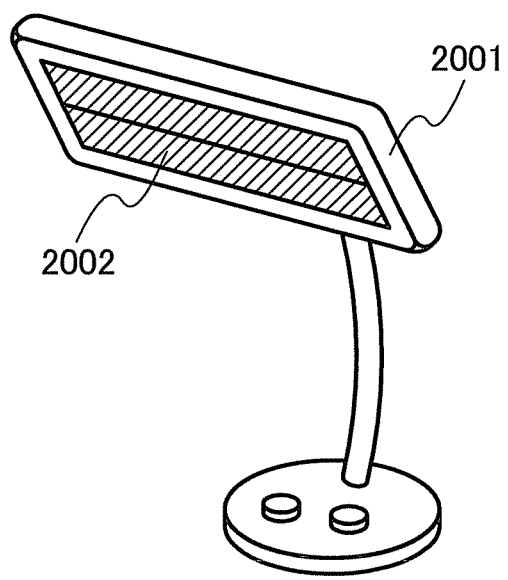
FIG. 7 illustrates a lighting device.

FIG. 7 illustrates an example in which the light-emitting element described in Embodiment 4 or 5 is used for a table lamp which is a lighting device. The table lamp illustrated in FIG. 7 includes a housing 2001 and a light source 2002, and the light-emitting element described in Embodiment 4 or 5 is used for the light source 2002.

Figure 8:
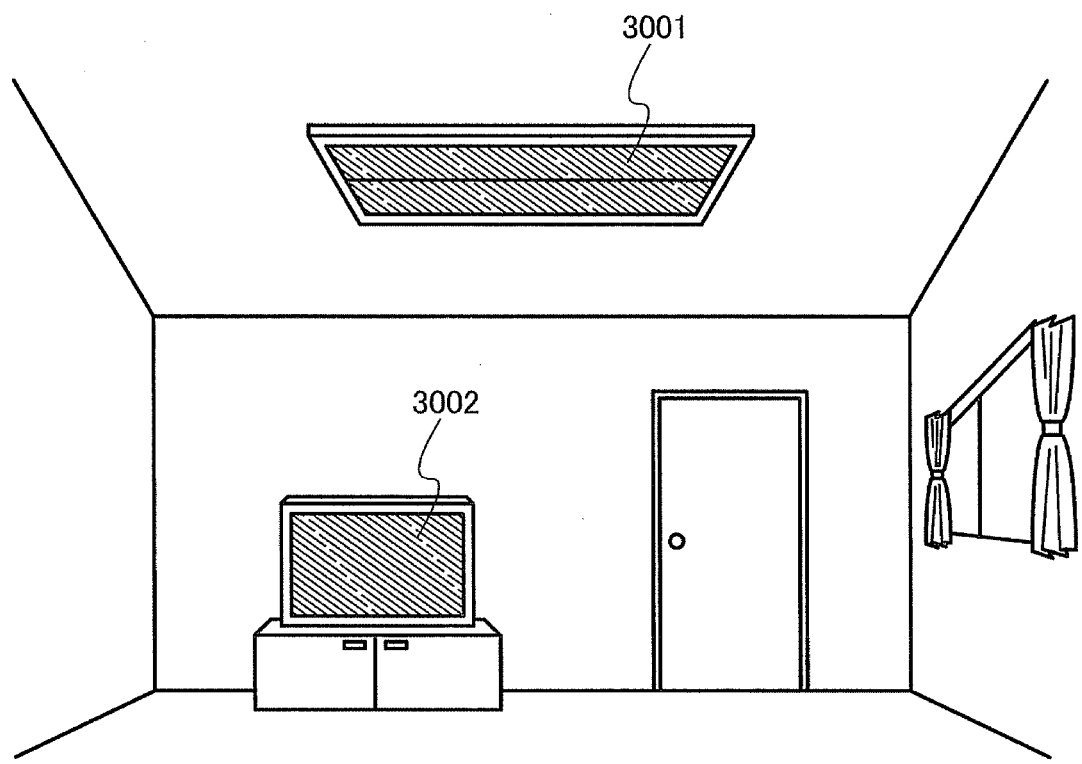
FIG. 8 illustrates a lighting device.

FIG. 8 illustrates an example in which the light-emitting element described in Embodiment 4 or 5 is used for indoor lighting devices 3001 and 3002. Since the light-emitting element described in Embodiment 4 or 5 has reduced power consumption, a lighting device that has reduced power consumption can be obtained. Further, since the light-emitting element described in Embodiment 4 or 5 can have a large area, the light-emitting element can be used for a large-area lighting device. Furthermore, since the light-emitting element described in Embodiment 4 or 5 is thin, a lighting device having a reduced thickness can be fabricated.

Figure 9:
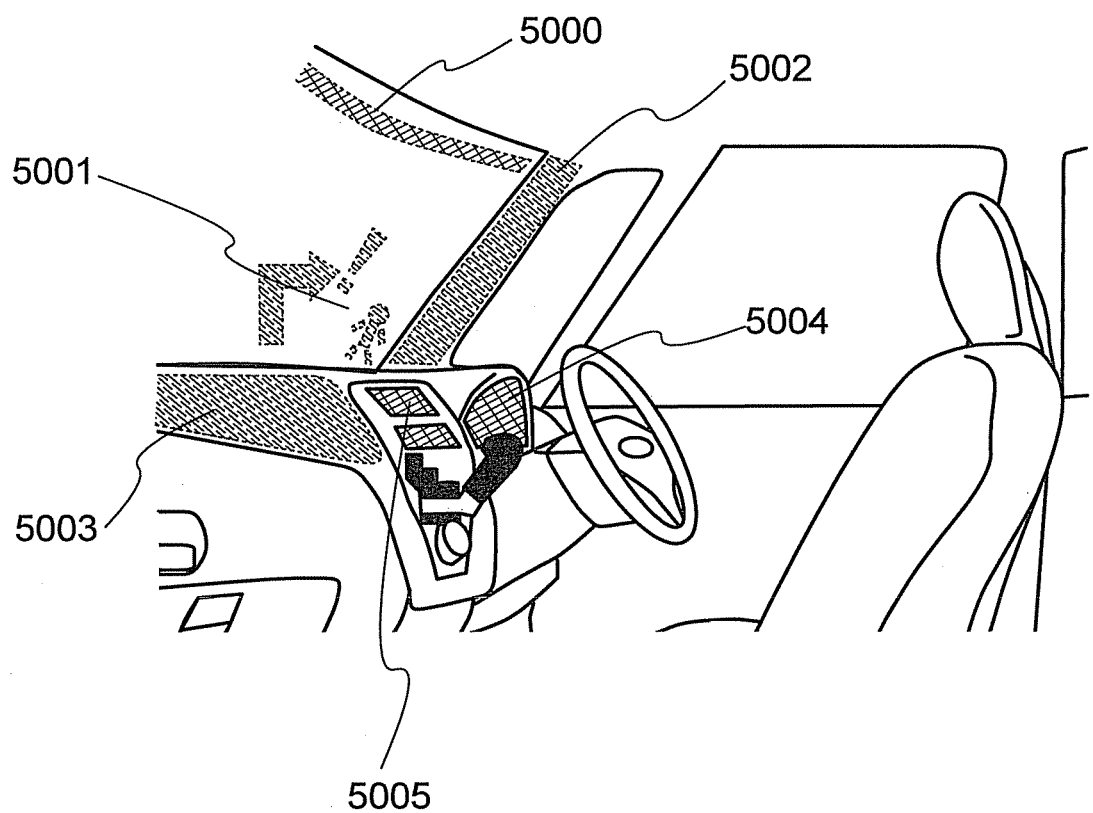
FIG. 9 illustrates in-vehicle display devices and lighting devices.

The light-emitting element described in Embodiment 4 or 5 can also be used for an automobile windshield or dashboard. One mode in which the light-emitting elements described in Embodiment 4 or 5 are used for an automobile windshield and an automobile dashboard is illustrated in FIG. 9. Displays 5000 to 5005 each include the light-emitting element described in Embodiment 4 or 5.

The display 5000 and the display 5001 are display devices which are provided in the automobile windshield and in which the light-emitting elements described in Embodiment 4 or 5 are incorporated. The light-emitting elements described in Embodiment 4 or 5 can be formed into so-called see-through display devices, through which the opposite side can be seen, by including a first electrode and a second electrode formed with electrodes having a light-transmitting property. Such see-through display devices can be provided even in the automobile windshield, without hindering the vision. Note in the case where a transistor for driving the light-emitting element is provided, a transistor having a light-transmitting property, such as an organic transistor using an organic semiconductor material or a transistor using an oxide semiconductor, is preferably used.

The display 5002 is a display device which is provided in a pillar portion and in which the light-emitting element described in Embodiment 4 or 5 is incorporated. The display 5002 can compensate for the view hindered by the pillar portion by showing an image taken by an imaging element provided in the automobile body. Similarly, the display 5003 provided in the dashboard can compensate for the view hindered by the automobile body by showing an image taken by an imaging element provided in the outside of the automobile body, which leads to elimination of blind areas and enhancement of safety. Showing an image so as to compensate for the area which a driver cannot see, makes it possible for the driver to confirm safety easily and comfortably.

The display 5004 and the display 5005 can provide a variety of kinds of information such as information of navigation, speedometer, tachometer, mileage (travel distance), fuel meter, gearshift indicator, and air condition. The content or layout of the display can be changed freely by a user as appropriate. Further, such information can also be shown in the displays 5000 to 5003. Note that the displays 5000 to 5005 can also be used as lighting devices.

By including any of the carbazole compounds described in Embodiment 1, the light-emitting element described in Embodiment 4 or 5 has low driving voltage and lower power consumption. When a number of large screens are provided, load on a battery can be reduced, which provides comfortable use. The light-emitting device and the lighting device each using the light-emitting element described in Embodiment 4 or 5 can be suitably used as an in-vehicle light-emitting device or lighting device.

Example 1

Synthesis Example 1

In this example, a method of synthesizing 2-[4-{3-(dibenzothiophen-4-yl)-9H-carbazol-9-yl}phenyl]-1-phenylbenzimidazole (abbreviation: DBTCzBIm-II), which is the carbazole derivative represented by the general formula (G1), is described. A structure of DBTCzBIm-II is illustrated in the following structural formula (100).

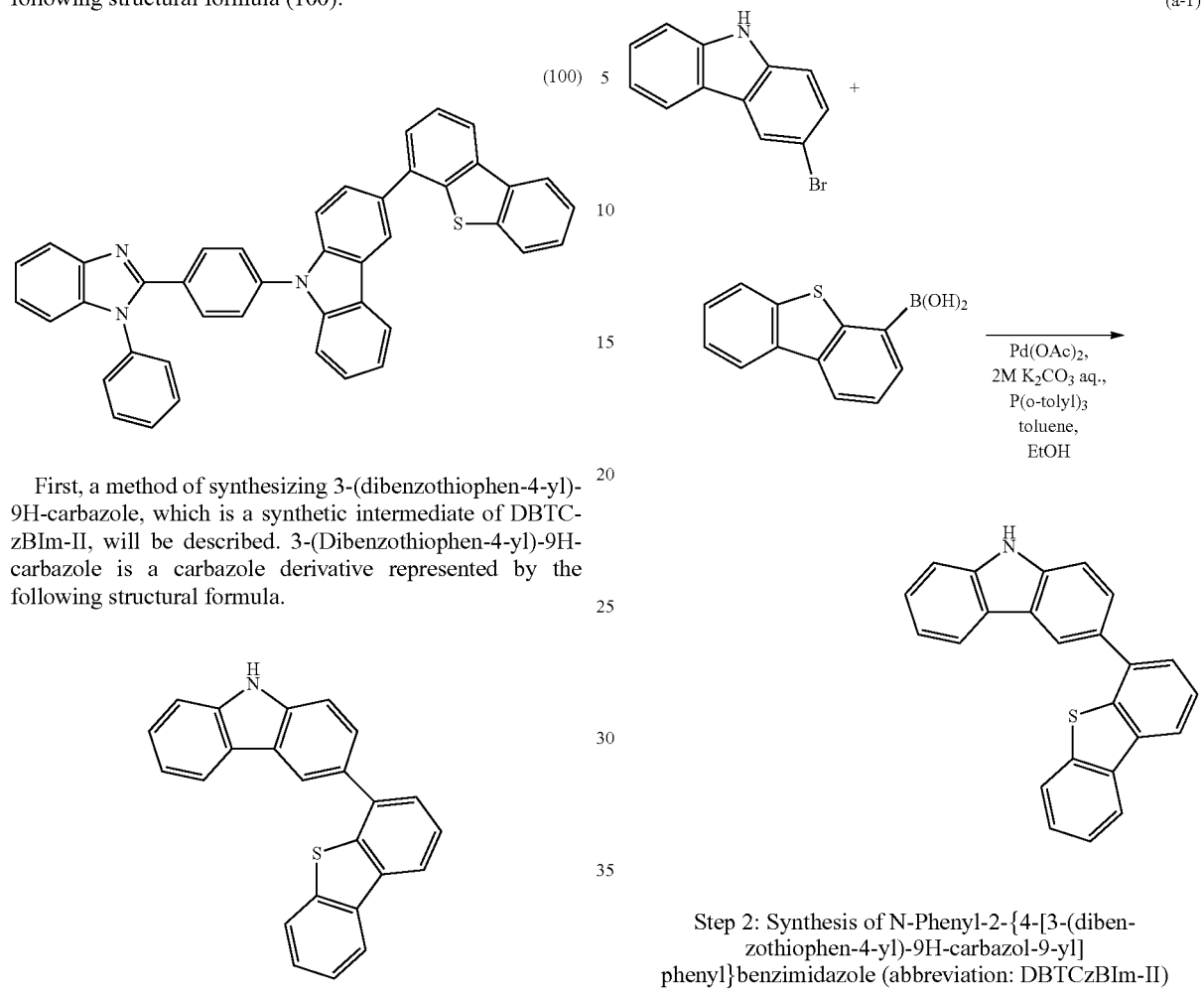

First, a method of synthesizing 3-(dibenzothiophen-4-yl)-9H-carbazole, which is a synthetic intermediate of DBTCzBIm-II, will be described. 3-(Dibenzothiophen-4-yl)-9H-carbazole is a carbazole derivative represented by the following structural formula.

Step 1: Synthesis of 3-(Dibenzothiophen-4-yl)-9H-carbazole

Into a 200 mL three-neck flask were placed 3.0 g (12 mmol) of 3-bromocarbazole, 2.8 g (12 mmol) of dibenzothiophene-4-boronic acid, and 150 mg (0.5 mol) of tri(ortho-tolyl)phosphine, and the air in the flask was replaced with nitrogen. To this mixture were added 40 mL of toluene, 40 mL of ethanol, and 15 mL (2.0 mol/L) of an aqueous solution of potassium carbonate. In the flask, the mixture was degassed by being stirred under reduced pressure. After the degassing, replacement with nitrogen was performed, and 23 mg (0.10 mmol) of palladium(II) acetate was added to this mixture, and then the mixture was refluxed at 110° C. for 3 hours. After the reflux, the mixture was cooled to room temperature, and then the obtained solid was collected by suction filtration. The collected solid was dissolved in 100 mL of toluene, and this solution was filtered through Celite (produced by Wako Pure Chemical Industries, Ltd., Catalog No. 531-16855), Florisil (produced by Wako Pure Chemical Industries, Ltd., Catalog No. 540-00135), and alumina. The solid obtained by concentration of the obtained filtrate was recrystallized from toluene/hexane, so that 1.4 g of a white solid was obtained in 32% yield. The synthesis scheme of Step 1 is illustrated in the formula (a-1).

Step 2: Synthesis of N-Phenyl-2-{4-[3-(dibenzothiophen-4-yl)-9H-carbazol-9-yl]phenyl}benzimidazole (abbreviation: DBTCzBIm-II)

Into a 100 mL three-neck flask were placed 0.36 g (1.0 mmol) of N-phenyl-2-(4-bromophenyl)benzimidazole and 0.36 g (1.0 mmol) of 3-(dibenzothiophen-4-yl)-9H-carbazole, and the air in the flask was replaced with nitrogen. To this mixture were added 10 mL of toluene, 0.10 mL of tri(tert-butyl)phosphine (a 10 wt % hexane solution), and 0.15 g (4.3 mmol) of sodium tert-butoxide. This mixture was degassed while being stirred under reduced pressure. After this mixture was heated to 80° C., 5.0 mg (0.025 mmol) of bis(dibenzylideneacetone)palladium(0) was added thereto, and then the mixture was stirred at 80° C. for 3 hours. After the stirring, 14 mg (0.025 mmol) of bis(dibenzylideneacetone)palladium(0) was added to this mixture, and then it was further stirred at 110° C. for 7.5 hours. After the stirring, about 30 mL of toluene was added to the mixture, and then it was stirred at 80° C. This mixture was subjected to hot filtration with ethyl acetate through Celite (produced by Wako Pure Chemical Industries, Ltd., Catalog No. 531-16855), Florisil (produced by Wako Pure Chemical Industries, Ltd., Catalog No. 540-00135), and alumina. The obtained filtrate was concentrated to give a white solid. The obtained solid was dissolved in toluene. The mixture was purified by silica gel column chromatography (a developing solvent in which the ratio of hexane to ethyl acetate was 4:1), and further recrystallized from toluene/hexane, so that 0.41 g of a white solid was obtained in 65% yield. The synthesis scheme of Step 2 is illustrated in the formula (b-1).

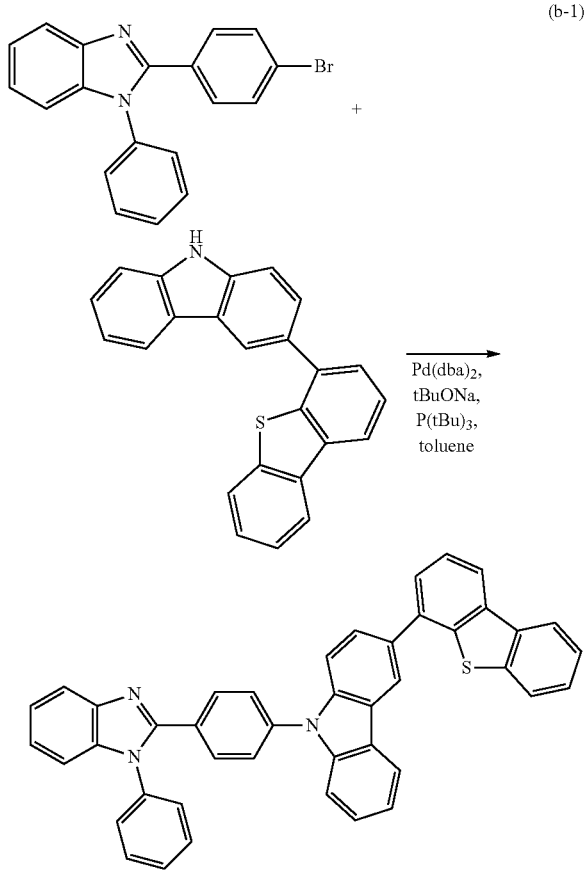

Then, 0.40 g of the obtained white solid was purified by sublimation. A train sublimation method was used, and the obtained white solid was heated at 290° C. under a pressure of 2.3 Pa with a flow rate of argon gas of 5.0 of mL/min. After purification by sublimation, 0.32 g of a colorless transparent solid was recovered in 78% yield.

Figure 10A:
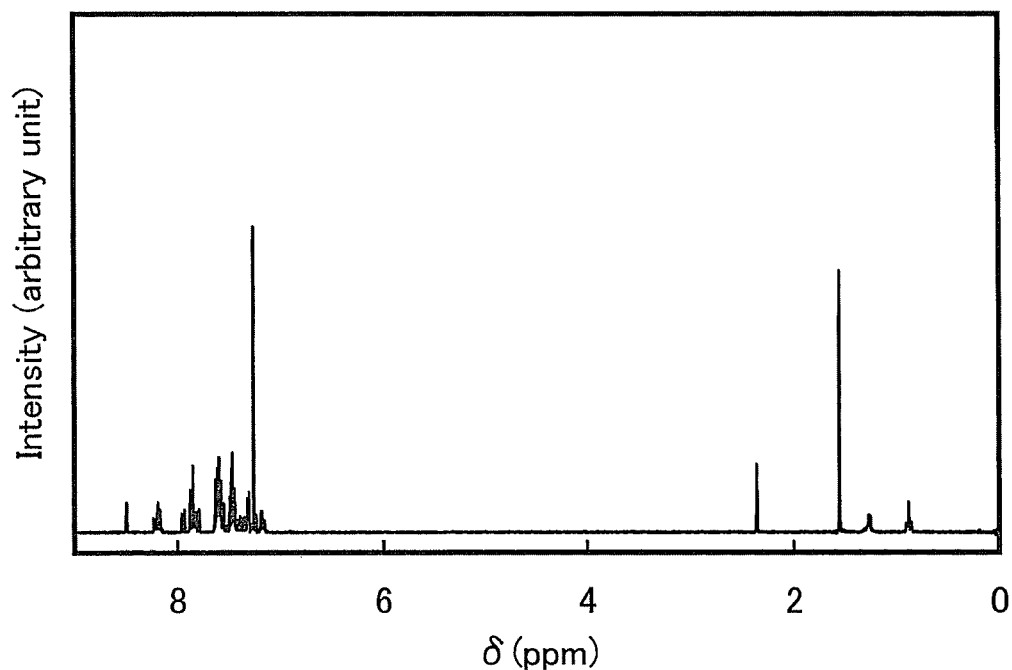
FIGS. 10A and 10B are $^1$H NMR charts of DBTCzBIm-II.
Figure 10B:
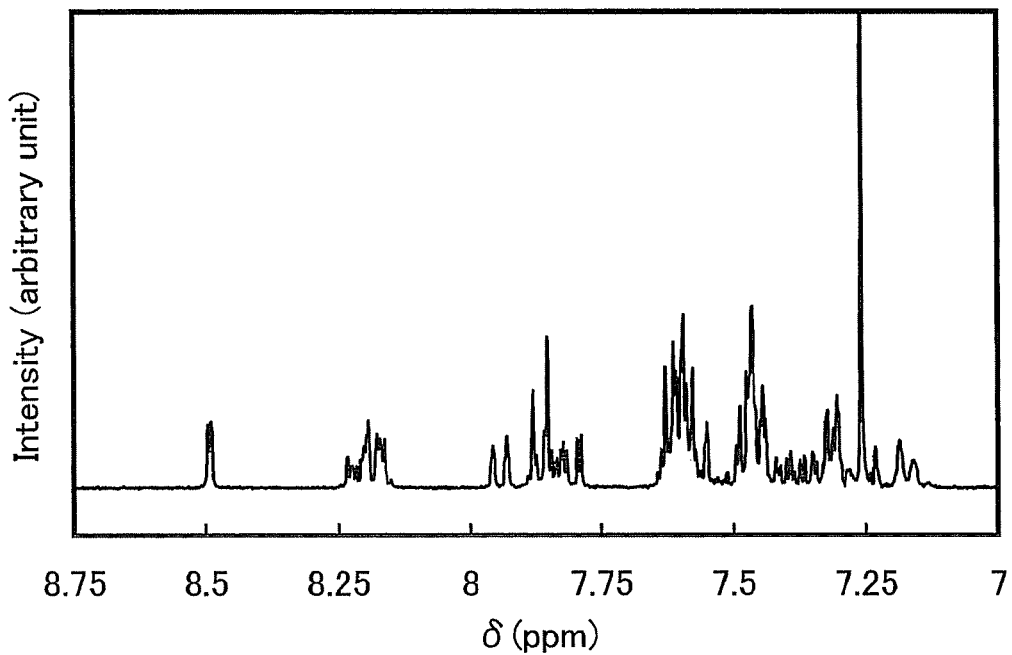

The colorless transparent solid after purification by sublimation was subjected to nuclear magnetic resonance ($^1$H NMR) spectroscopy. The measurement data are shown below. In addition, $^1$H NMR charts are shown in FIGS. 10A and 10B. Note that FIG. 10B is a chart where the range of from 7.00 ppm to 8.75 ppm in FIG. 10A is enlarged.

$^1$H NMR (CDCl$_3$, 300 MHz): δ=7.31-7.42 (m, 4H), 7.44-7.49 (m, 6H), 7.51-7.64 (m, 8H), 7.79-7.89 (m, 4H), 7.94 (d, J=7.8 Hz, 1H), 8.45-8.23 (m, 3H), 8.49 (d, J=2.1 Hz, 1H)

The measurement results showed that DBTCzBIm-II, which is the carbazole derivative represented by the above structural formula (100), was obtained.

Figure 11A:
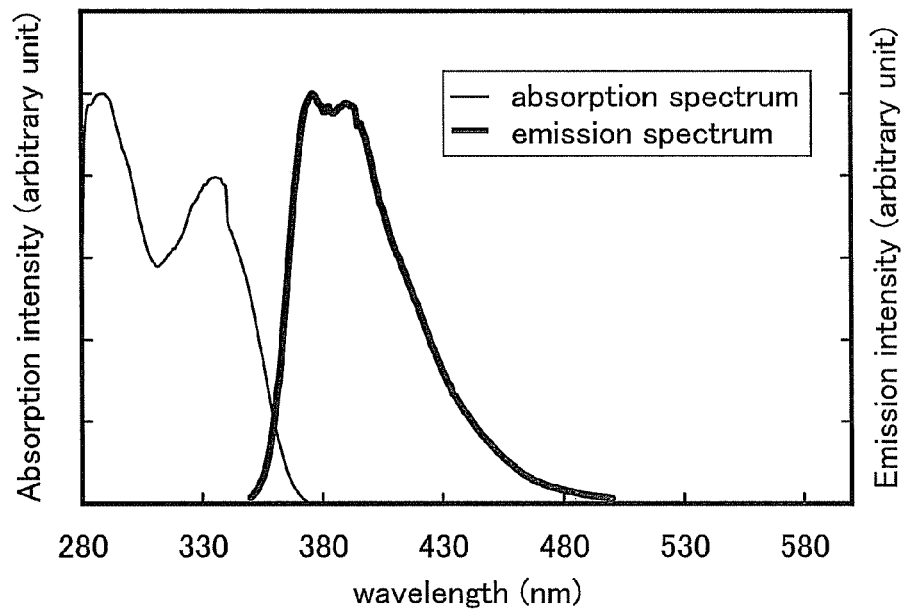
FIGS. 11A and 11B each show an absorption and emission spectra of DBTCzBIm-II.
Figure 11B:
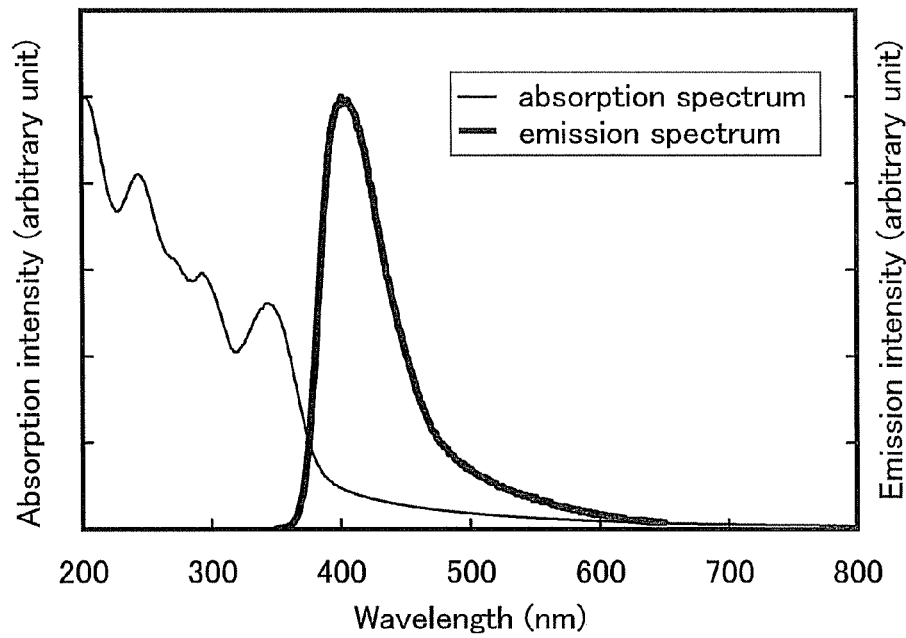

Further, an absorption and emission spectra of DBTCzBIm-II in a toluene solution of DBTCzBIm-II are shown in FIG. 11A, and an absorption and emission spectra of a thin film of DBTCzBIm-II are shown in FIG. 11B. An ultraviolet-visible spectrophotometer (V-550, produced by JASCO Corporation) was used for the measurements of the spectra. The spectra of the toluene solution were measured with a toluene solution of DBTCzBIm-II put in a quartz cell. The spectra of the thin film were measured with a sample prepared by evaporation of DBTCzBIm-II on a quartz substrate. Note that in the case of the absorption spectrum of the toluene solution, the absorption spectrum obtained by subtraction of the absorption spectra of quartz and toluene from the measured spectra is shown in the drawing, and in the case of the absorption spectrum of the thin film, the absorption spectrum obtained by subtraction of that of the quartz substrate from the measured spectra is shown in the drawing.

FIG. 11A shows that the greatest emission wavelength of DBTCzBIm-II in the toluene solution of DBTCzBIm-II is around 377 nm (at an excitation wavelength of 340 nm), and FIG. 11B shows that the greatest emission wavelength of the thin film of DBTCzBIm-II is around 402 nm (at an excitation wavelength of 339 nm).

Further, the ionization potential of DBTCzBIm-II in a thin film state was measured by a photoelectron spectrometer (AC-2, produced by Riken Keiki, Co., Ltd.) in the air. The obtained value of the ionization potential was converted to a negative value, so that the HOMO level of DBTCzBIm-II was −5.68 eV. From the data of the absorption spectra of the thin film in FIG. 11B, the absorption edge of DBTCzBIm-II, which was obtained from a Tauc plot with an assumption of direct transition, was 3.31 eV. Therefore, the optical band gap of DBTCzBIm-II in the solid state was estimated at 3.31 eV; from the values of the HOMO level obtained above and this band gap, the LUMO level of DBTCzBIm-II was able to be estimated at −2.37 eV. It was thus found that DBTCzBIm-II had a wide band gap of 3.31 eV in the solid state.

Further, the oxidation and reduction characteristics of DBTCzBIm-II were measured. These were examined by cyclic voltammetry (CV) measurement. Note that an electrochemical analyzer (ALS model 600A or 600C, produced by BAS Inc.) was used for the measurements.

For a solution for the CV measurements, dehydrated N,N-dimethylformamide (DMF, produced by Sigma-Aldrich Inc., 99.8%, catalog No. 22705-6) was used as a solvent, and tetra-n-butylammonium perchlorate (n-Bu$_4$NClO$_4$, produced by Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, produced by BAS Inc.) was used as a working electrode; a platinum electrode (a VC-3 Pt counter electrode (5 cm), produced by BAS Inc.) was used as an auxiliary electrode; and an Ag/Ag$^+$ electrode (an RE5 nonaqueous solvent reference electrode, produced by BAS Inc.) was used as a reference electrode. Note that the measurements were conducted at room temperature (20° C. to 25° C.). The scan rates for the CV measurements were uniformly set to 0.1 V/s.

Figure 19A:
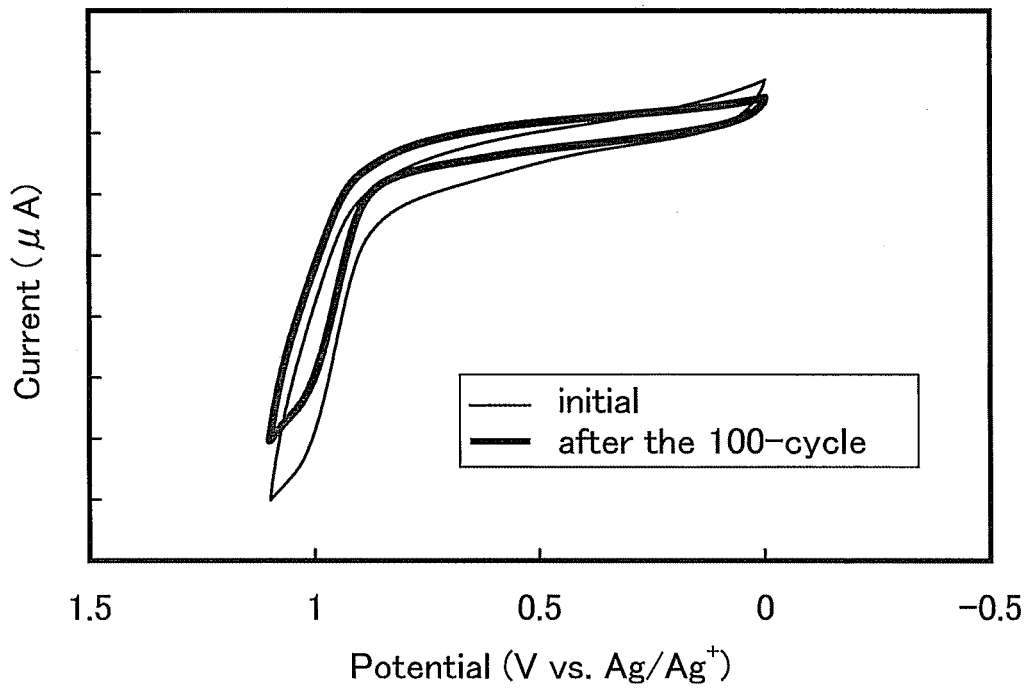
FIGS. 19A and 19B are CV charts of DBTCzBIm-II in a DMF solution of DBTCzBIm-II.
Figure 19B:
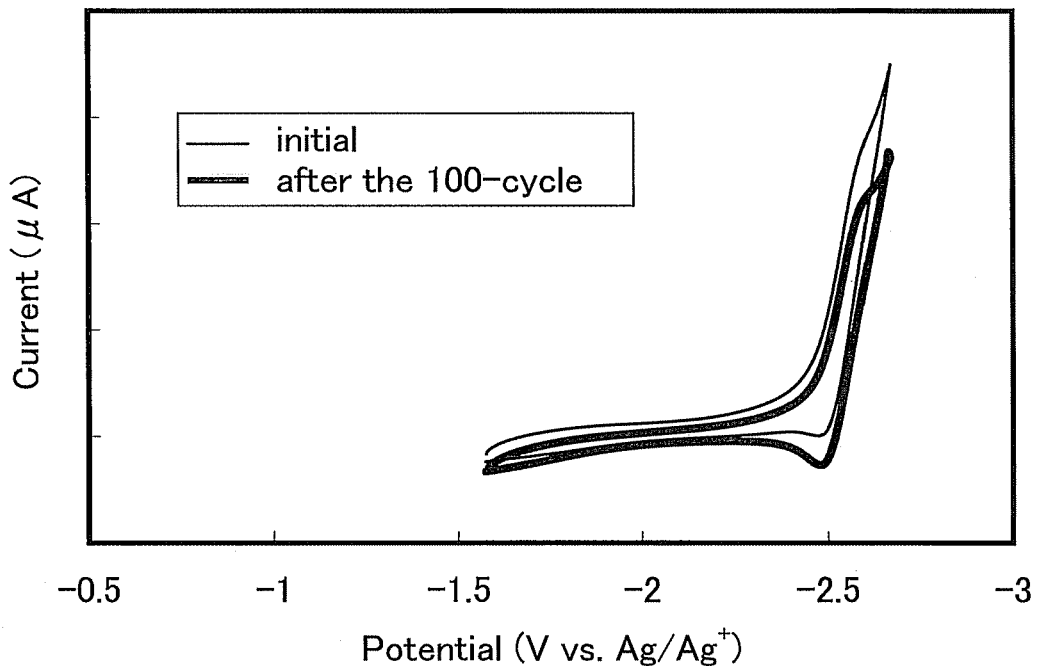

In the measurements of the oxidation characteristics, scanning in which the potential of the working electrode with respect to the reference electrode was changed from 0.00 V to 1.10 V and then changed from 1.10 V to 0.00 V was one cycle, and 100-cycle measurements were performed. In the measurements of the reduction characteristics, scanning in which the potential of the working electrode with respect to the reference electrode was changed from −1.57 V to −2.67 V and then changed from −2.67 V to −1.57 V was one cycle, and 100-cycle measurements were performed. The measurement results are shown in FIGS. 19A and 19B. Note that FIG. 19A shows a CV chart of the oxidation characteristics, and FIG. 19B shows a CV chart of the reduction characteristics.

The measurement results revealed that DBTCzBIm-II showed a property effective against repetition of redox reactions between an oxidized state and a neutral state and repetition of redox reactions between a reduced state and a neutral state, without large variations in the oxidation and reduction peaks of the oxidation and reduction characteristics even after the 100-cycle measurements.

Further, the HOMO and LUMO levels of DBTCzBIm-II were calculated also from the CV measurement results.

First, the potential energy of the reference electrode (Ag/Ag⁺ electrode) with respect to the vacuum level, which was used, is −4.94 eV.

According to FIG. 19A showing the oxidation characteristics, the oxidation peak potential $E_{pa}$ of DBTCzBIm-II was 1.03 V. In addition, the reduction peak potential $E_{pc}$ thereof was 0.90 V. Therefore, the half-wave potential (intermediate potential between $E_{pa}$ and $E_{pc}$) can be calculated at 0.97 V. This means that DBTCzBIm-II is oxidized by an electric energy of 0.97 [V vs. Ag/Ag⁺], and this energy corresponds to the HOMO level. Here, since the potential energy of the reference electrode, which was used in this example, with respect to the vacuum level is −4.94 [eV] as described above, the HOMO level of DBTCzBIm-II was found to be as follows: −4.94−0.97=−5.91 [eV].

Similarly, according to FIG. 19B showing the reduction characteristics, the oxidation peak potential $E_{pa}$ of DBFCzBIm-II was −2.47 V, and the reduction peak potential $E_{pc}$ thereof was −2.61V. Therefore, the half-wave potential (intermediate potential between $E_{pa}$ and $E_{pc}$) can be calculated at −2.54 V. This means that DBFCzBIm-II is reduced by an electric energy of −2.54 [V vs. Ag/Ag⁺], and this energy corresponds to the LUMO level. Here, since the potential energy of the reference electrode, which was used in this example, with respect to the vacuum level is −4.94 [eV] as described above, the LUMO level of DBFCzBIm-II was found to be as follows: −4.94−(−2.54)=−2.40 [eV].

Note that the potential energy of the reference electrode (Ag/Ag⁺ electrode) with respect to the vacuum level corresponds to the Fermi level of the Ag/Ag⁺ electrode, and should be calculated from a value obtained by measuring a substance whose potential energy with respect to the vacuum level is known, with the use of the reference electrode (Ag/Ag⁺ electrode).

How the potential energy (eV) of the reference electrode (Ag/Ag⁺ electrode), which was used in this example, with respect to the vacuum level is calculated will be specifically described. It is known that the oxidation-reduction potential of ferrocene in methanol is +0.610 V [vs. SHE] with respect to the standard hydrogen electrode (reference: Christian R. Goldsmith et al., *J. Am. Chem. Soc.*, Vol. 124, No. 1, pp. 83-96, 2002). In contrast, using the reference electrode used in this example, the oxidation-reduction potential of ferrocene in methanol was calculated at +0.11V [vs. Ag/Ag⁺]. Thus, it was found that the potential energy of this reference electrode was lower than that of the standard hydrogen electrode by 0.50 [eV].

Here, it is known that the potential energy of the standard hydrogen electrode with respect to the vacuum level is −4.44 eV (reference: Toshihiro Ohnishi and Tamami Koyama, *High molecular EL material*, Kyoritsu shuppan, pp. 64-67). Therefore, the potential energy of the reference electrode used in this example with respect to the vacuum level can be calculated as follows: −4.44−0.50=−4.94 [eV].

Example 2

Synthesis Example 2

In this example, a method of synthesizing 2-[4-{3-(dibenzofuran-4-yl)-9H-carbazol-9-yl}phenyl]-1-phenylbenzimidazole (abbreviation: DBFCzBIm-II), which is one of the carbazole derivatives described in Embodiment 1, is described. A structure of DBFCzBIm-II is illustrated in the following structural formula (200).

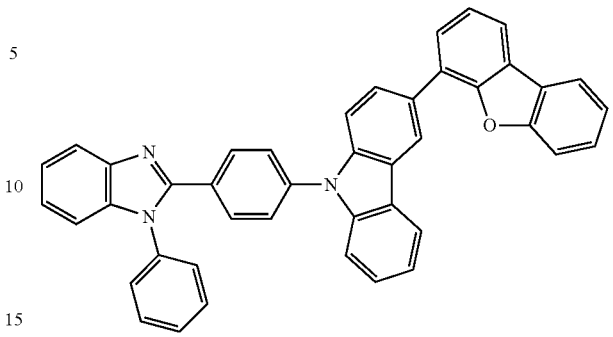

(200)

First, a method of synthesizing 4-(9H-carbazol-3-yl)dibenzofuran, which is a synthetic intermediate of DBFCzBIm-II, will be described. 4-(9H-Carbazol-3-yl)dibenzofuran is a carbazole derivative represented by the following structural formula.

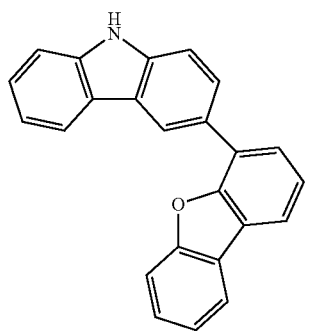 [SMILES: c1ccc2c(c1)[nH]c1ccc(-c3cccc4c3oc3ccccc34)cc12]

Step 1: Synthesis of
4-(9H-Carbazol-3-yl)dibenzofuran

Into a 200 mL three-neck flask were placed 2.0 g (8.1 mmol) of 3-bromocarbazole, 1.7 g (8.1 mmol) of dibenzofuran-4-boronic acid, and 150 mg (0.5 mol) of tri(ortho-tolyl)phosphine, and the air in the flask was replaced with nitrogen. To this mixture were added 20 mL of toluene, 20 mL of ethanol, and 15 mL (0.2 mol) of an aqueous solution of potassium carbonate (2.0 mol/L). In the flask, the mixture was degassed by being stirred under reduced pressure. After 23 mg (0.10 mmol) of palladium(II) acetate was added to this mixture, the mixture was refluxed at 80° C. After the reflux, the mixture was cooled to room temperature, and then the obtained solid was collected by suction filtration. The collected solid was dissolved in 100 mL of toluene, and this solution was filtered through Celite (produced by Wako Pure Chemical Industries, Ltd., Catalog No. 531-16855), Florisil (produced by Wako Pure Chemical Industries, Ltd., Catalog No. 540-00135), and alumina. The solid obtained by concentration of the obtained filtrate was recrystallized from toluene/hexane, so that 2.3 g of a white solid was obtained in 85% yield. The synthesis scheme of Step 1 is illustrated in the formula (a-2).

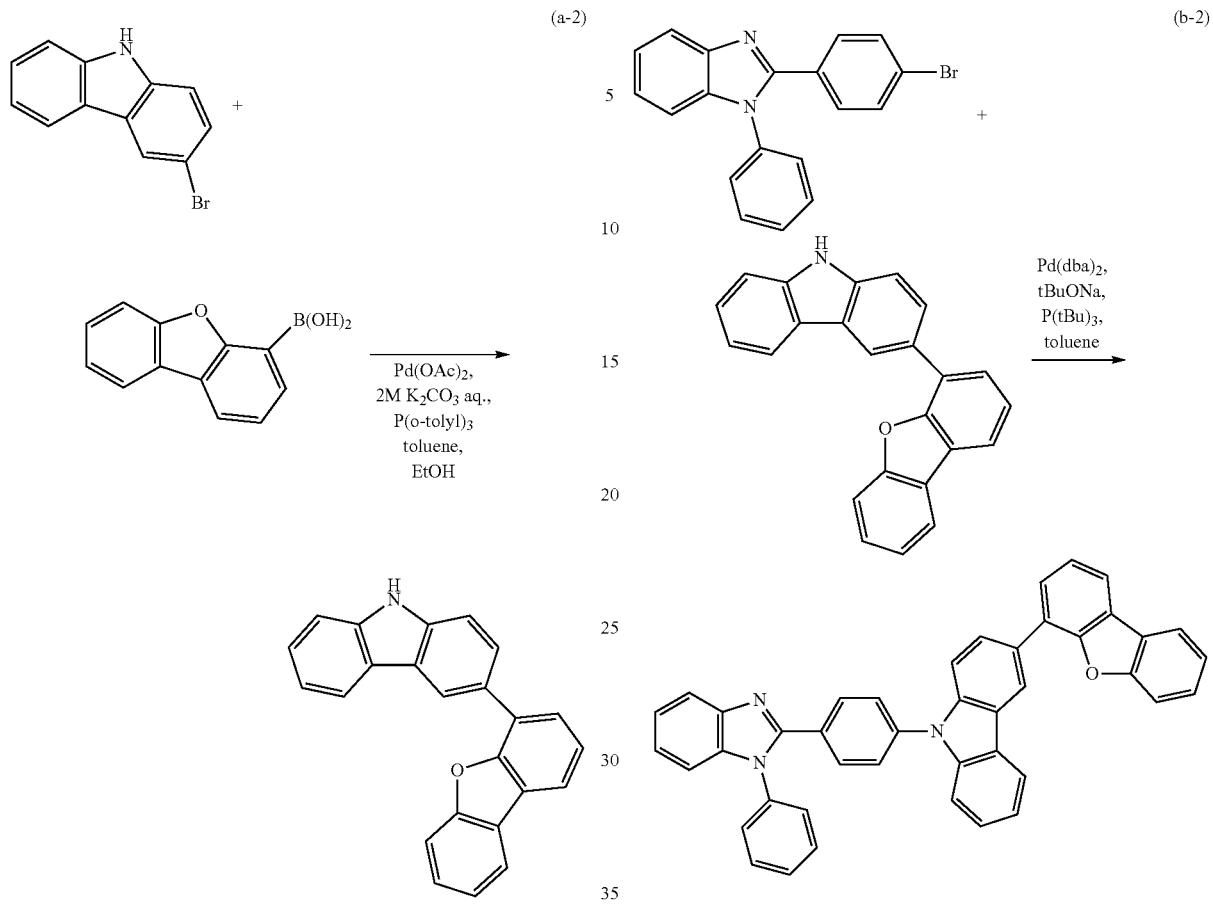

Step 2: Synthesis of 2-[4-{3-(Dibenzofuran-4-yl)-9H-carbazol-9-yl}phenyl]-1-phenylbenzimidazole (abbreviation: DBFCzBIm-II)

Into a 100 mL three-neck flask were placed 0.70 g (1.0 mmol) of 2-(4-bromophenyl)-3-phenylbenzimidazole and 0.67 g (1.0 mmol) of 4-(9H-carbazol-3-yl)dibenzofuran, and the air in the flask was replaced with nitrogen. To this mixture were added 15 mL of toluene, 0.10 mL of tri(tert-butyl) phosphine (a 10 wt % hexane solution), and 0.48 g (4.3 mmol) of sodium tert-butoxide. This mixture was degassed while being stirred under reduced pressure. This mixture was stirred at 110° C. for 20 hours. After the stirring, the mixture was washed twice with about 30 mL of water, and the mixture was separated into an organic layer and an aqueous layer. Then, the aqueous layer was subjected to extraction twice with about 30 mL of toluene. The organic layer and the solution of the extract were combined and washed once with about 100 mL of saturated brine. The obtained organic layer was dried over magnesium sulfate, and this mixture was subjected to filtration through Celite (produced by Wako Pure Chemical Industries, Ltd., Catalog No. 531-16855), Florisil (produced by Wako Pure Chemical Industries, Ltd., Catalog No. 540-00135), and alumina. The obtained filtrate was concentrated to give a brown solid. The obtained brown solid was purified by silica gel column chromatography (a developing solvent in which the ratio of ethyl acetate to toluene was 5:95), and further recrystallized from hexane/toluene, so that 0.86 g of a pale brown solid was obtained in 71% yield. The synthesis scheme of Step 2 is illustrated in the formula (b-2).

By a train sublimation method, 854 mg of the obtained pale brown solid was purified. Conditions for purification by sublimation were set as follows: the pressure was 1.8 Pa, the flow rate of argon gas was 5.0 mL/min, and the temperature of the heating was 290° C. After purification by sublimation, 0.64 g of a pale brown solid of the substance which was the object of the synthesis was recovered in a yield of 75%.

Figure 12A:
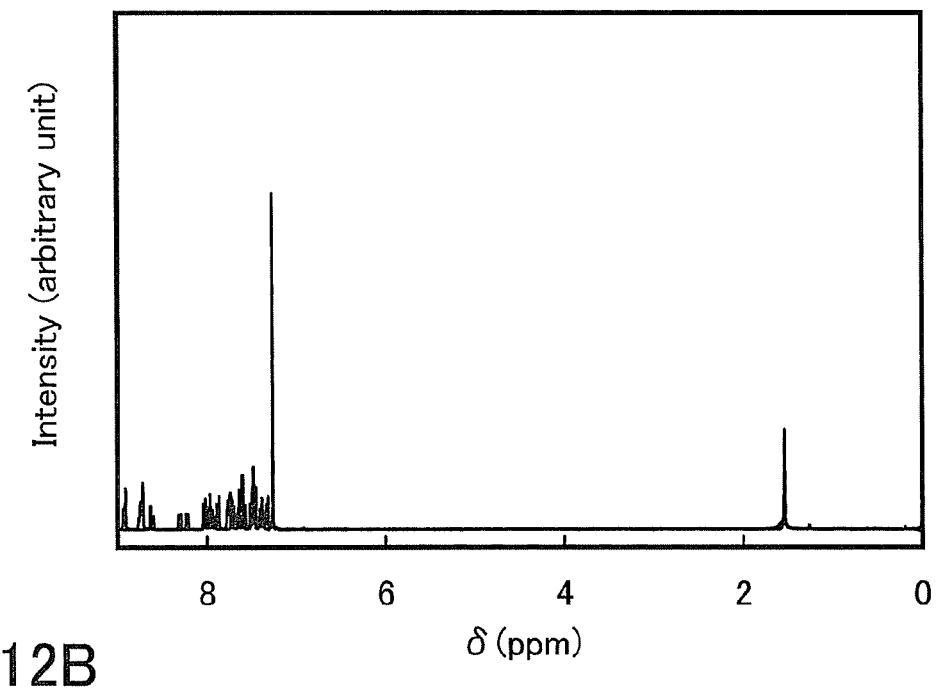
FIGS. 12A and 12B are $^1$H NMR charts of DBFCzBIm-II.
Figure 12B:
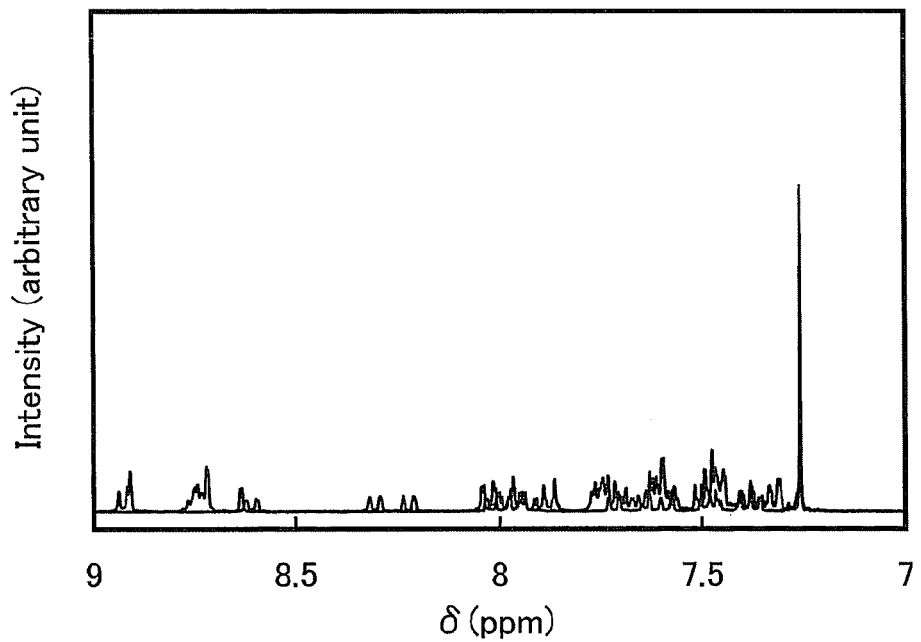

The pale brown solid after purification by sublimation was subjected to nuclear magnetic resonance ($^1$H NMR) spectroscopy. The measurement data are shown below. In addition, $^1$H NMR charts are shown in FIGS. 12A and 12B. Note that FIG. 12B is a chart where the range of from 7 ppm to 9 ppm in FIG. 12A is enlarged.

$^1$H NMR (CDCl$_3$, 300 MHz): δ=7.31-7.50 (m, 11H), 7.54-7.65 (m, 7H), 7.72 (dd, J$_1$=1.5 Hz, J$_2$=7.5 Hz, 1H), 7.88 (d, J=8.7 Hz, 2H), 7.34-8.03 (m, 4H), 8.22 (d, J=7.5 Hz, 1H), 8.63 (d, J=1.5 Hz, 1H)

The measurement results showed that DBFCzBIm-II, which is the carbazole derivative represented by the above structural formula (200), was obtained.

Figure 13A:
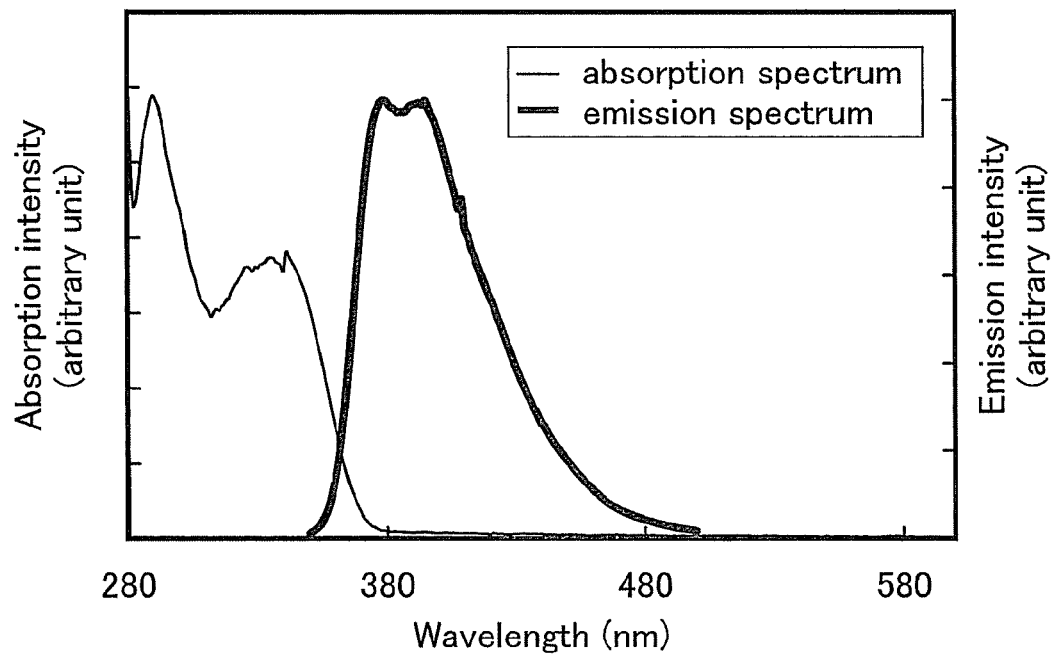
FIGS. 13A and 13B each show an absorption and emission spectra of DBFCzBIm-II.
Figure 13B:
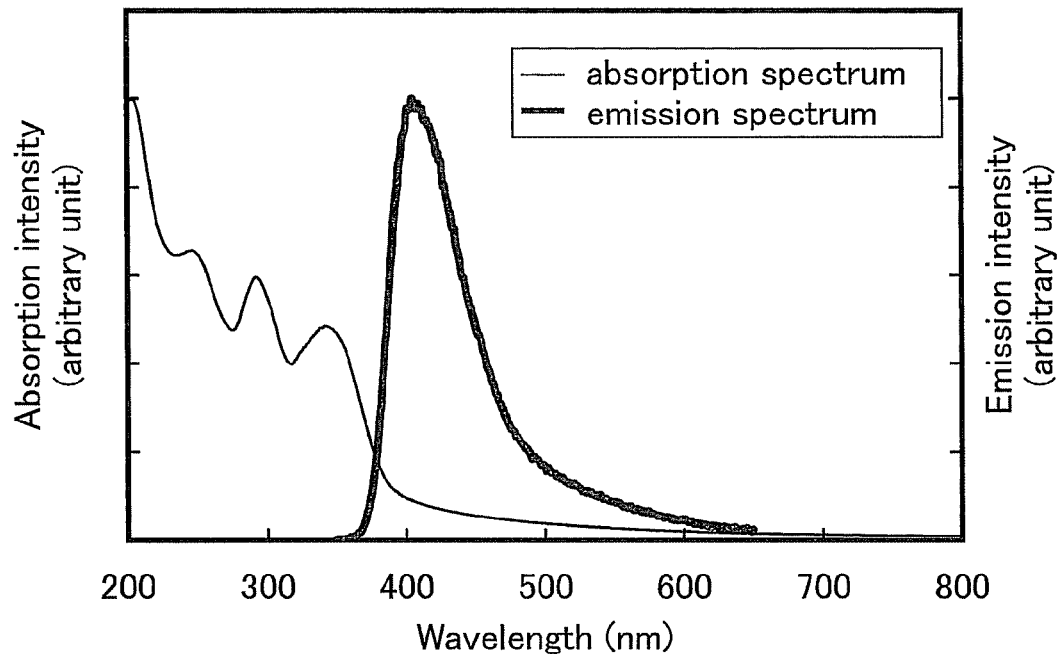

Further, an absorption and emission spectra of DBFCzBIm-II in a toluene solution of DBFCzBIm-II are shown in FIG. 13A, and an absorption and emission spectra of a thin film of DBFCzBIm-II are shown in FIG. 13B. An ultraviolet-visible spectrophotometer (V-550, produced by JASCO Corporation) was used for the measurements of the spectra. The spectra of the toluene solution were measured with a toluene solution of DBFCzBIm-II put in a quartz cell. The spectra of the thin film were measured with a sample prepared by evaporation of DBFCzBIm-II on a quartz substrate. Note that in the case of the absorption spectrum of the toluene solution, the absorption spectrum obtained by subtraction of the absorption spectra of quartz and toluene from the measured spectra is shown in the drawing, and in the case of the absorption spectrum of the thin film, the absorption spectrum obtained by subtraction of that of the quartz substrate from the measured spectra is shown in the drawing.

FIG. 13A shows that the maximum emission wavelengths of DBFCzBIm-II in a toluene solution of DBFCzBIm-II are around 380 nm and 395 nm (at an excitation wavelength of 340 nm), and FIG. 13B shows that the greatest emission wavelength of the thin film of DBFCzBIm-II is around 405 nm (at an excitation wavelength of 332 nm).

Further, the ionization potential of a thin film of DBFCzBIm-II was measured by a photoelectron spectrometer (AC-2, produced by Riken Keiki, Co., Ltd.) in the air. The obtained value of the ionization potential was converted to a negative value, so that the HOMO level of DBFCzBIm-II was −5.71 eV. From the data of the absorption spectra of the thin film in FIG. 13B, the absorption edge of DBFCzBIm-II, which was obtained from a Tauc plot with an assumption of direct transition, was 3.28 eV. Therefore, the optical band gap of DBFCzBIm-II in the solid state was estimated at 3.28 eV; from the values of the HOMO level obtained above and this band gap, the LUMO level of DBFCzBIm-II was able to be estimated at −2.43 eV. It was thus found that DBFCzBIm-II had a wide band gap of 3.28 eV in the solid state.

Further, the oxidation and reduction characteristics of DBFCzBIm-II were measured. These were examined by cyclic voltammetry (CV) measurement. Note that an electrochemical analyzer (ALS model 600A or 600C, produced by BAS Inc.) was used for the measurements.

For a solution for the CV measurements, dehydrated N,N-dimethylformamide (DMF, produced by Sigma-Aldrich Inc., 99.8%, catalog No. 22705-6) was used as a solvent, and tetra-n-butylammonium perchlorate (n-Bu$_4$NClO$_4$, produced by Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, produced by BAS Inc.) was used as a working electrode; a platinum electrode (a VC-3 Pt counter electrode (5 cm), produced by BAS Inc.) was used as an auxiliary electrode; and an Ag/Ag$^+$ electrode (an RE5 nonaqueous solvent reference electrode, produced by BAS Inc.) was used as a reference electrode. Note that the measurements were conducted at room temperature (20° C. to 25° C.). The scan rates for the CV measurements were uniformly set to 0.1 V/s.

Figure 20A:
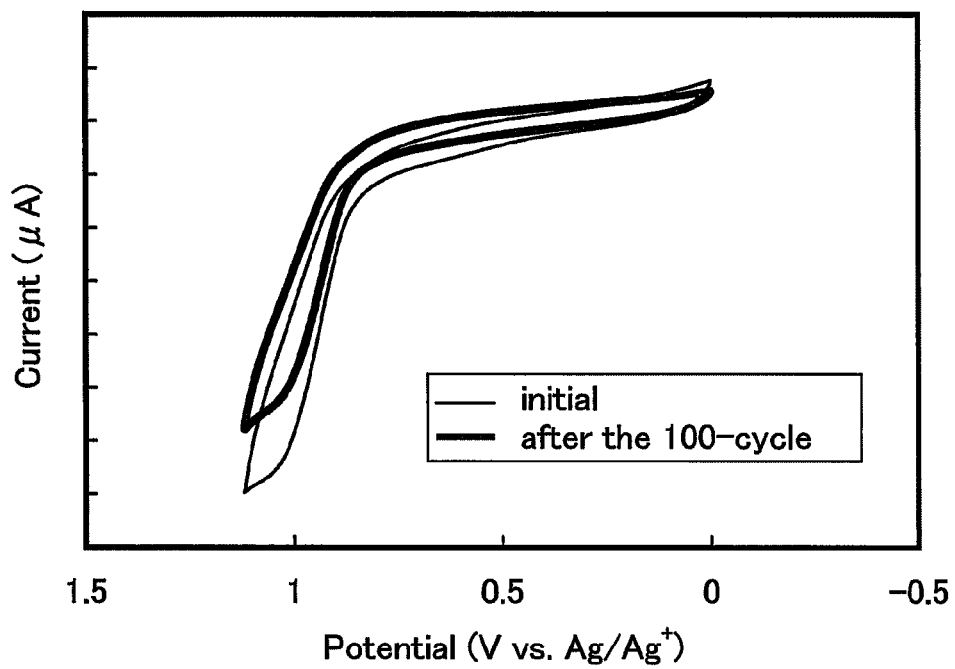
FIGS. 20A and 20B are CV charts of DBFCzBIm-II in a DMF solution of DBFCzBIm-II.
Figure 20B:
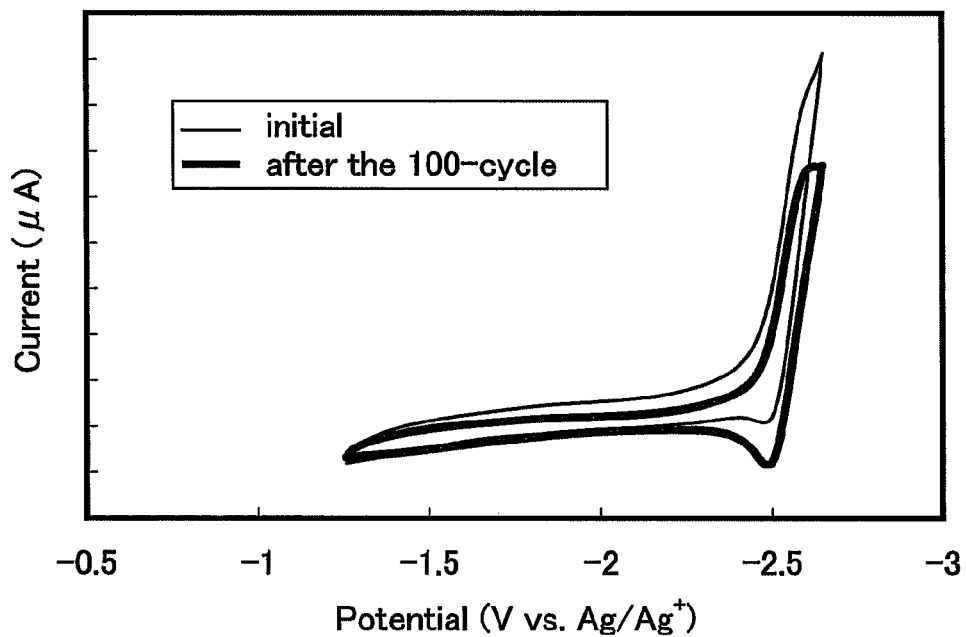

In the measurements of the oxidation characteristics, scanning in which the potential of the working electrode with respect to the reference electrode was changed from 0.00 V to 1.12 V and then changed from 1.12 V to 0.00 V was one cycle, and 100-cycle measurements were performed. In the measurements of the reduction characteristics, scanning in which the potential of the working electrode with respect to the reference electrode was changed from −1.26 V to −2.65 V and then changed from −2.65 V to −1.26 V was one cycle, and 100-cycle measurements were performed. The measurement results are shown in FIGS. 20A and 20B. Note that FIG. 20A shows a CV chart of the oxidation characteristics, and FIG. 20B shows a CV chart of the reduction characteristics.

The measurement results revealed that DBFCzBIm-II showed a property effective against repetition of redox reactions between an oxidized state and a neutral state and repetition of redox reactions between a reduced state and a neutral state, without large variations in the oxidation and reduction peaks of the oxidation and reduction characteristics even after the 100-cycle measurements.

Further, the HOMO and LUMO levels of DBFCzBIm-II were calculated also from the CV measurement results.

First, the potential energy of the reference electrode with respect to the vacuum level used was −4.94 eV, as determined in Example 1.

According to FIG. 20A showing the oxidation characteristics, the oxidation peak potential $E_{pa}$ of DBFCzBIm-II was 1.04 V. In addition, the reduction peak potential $E_{pc}$ was 0.89 V. Therefore, the half-wave potential (intermediate potential between $E_{pa}$ and $E_{pc}$) can be calculated at 0.97 V. This means that DBFCzBIm-II is oxidized by an electric energy of 0.97 [V vs. Ag/Ag$^+$], and this energy corresponds to the HOMO level. Here, since the potential energy of the reference electrode, which was used in this example, with respect to the vacuum level is −4.94 [eV] as described above, the HOMO level of DBFCzBIm-II was found to be as follows: −4.94−0.97=−5.91 [eV].

Similarly, according to FIG. 20B showing the reduction characteristics, the oxidation peak potential $E_{pa}$ of DBFCzBIm-II was −2.47 V, and the reduction peak potential $E_{pc}$ thereof was −2.62 V. Therefore, the half-wave potential (intermediate potential between $E_{pa}$ and $E_{pc}$) can be calculated at −2.55 V. This means that DBFCzBIm-II is reduced by an electric energy of −2.55 [V vs. Ag/Ag$^+$], and this energy corresponds to the LUMO level. Here, since the potential energy of the reference electrode, which was used in this example, with respect to the vacuum level is −4.94 [eV] as described above, the LUMO level of DBFCzBIm-II was found to be as follows: −4.94−(−2.55)=−2.39 [eV].

Example 3

In this example are described light-emitting elements using 2-[4-{3-(dibenzothiophen-4-yl)-9H-carbazol-9-yl}phenyl]-1-phenylbenzimidazole (abbreviation: DBTCzBIm-II, the structural formula (100)) and 2-[4-{3-(dibenzofuran-4-yl)-9H-carbazol-9-yl}phenyl]-1-phenylbenzimidazole (abbreviation: DBFCzBIm-II, the structural formula (200)), which are carbazole compounds described in Embodiment 1, as host materials of light-emitting layers each using an emission center substance that emits green phosphorescence.

The molecular structures of organic compounds used in this example are represented by the structural formulae (i) to (iv), (100), and (200) below. The element structure in FIG. 1A was a structure in which the electron-injection layer is provided between the electron-transport layer 114 and the second electrode 104.

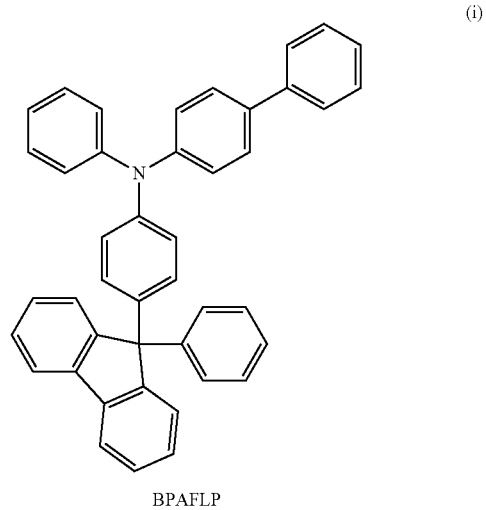

BPAFLP (i)

(ii)

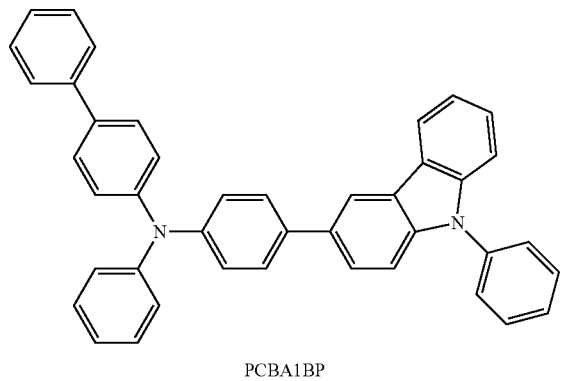

PCBA1BP (iii)

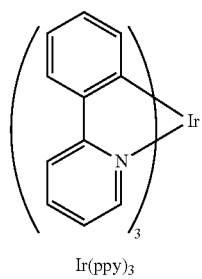

Ir(ppy)₃

(iv)

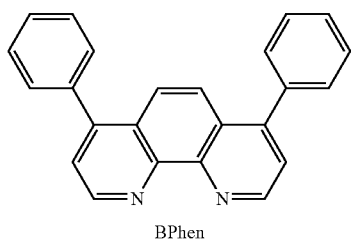

BPhen (100)

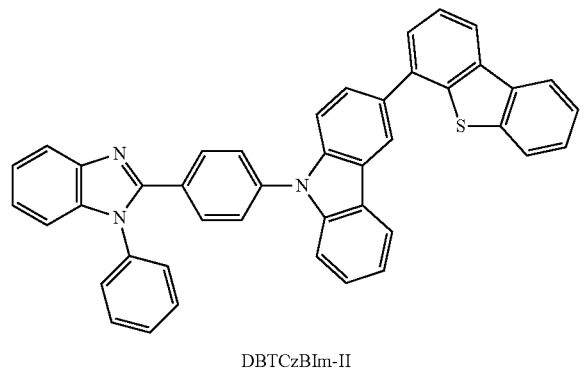

DBTCzBIm-II (200)

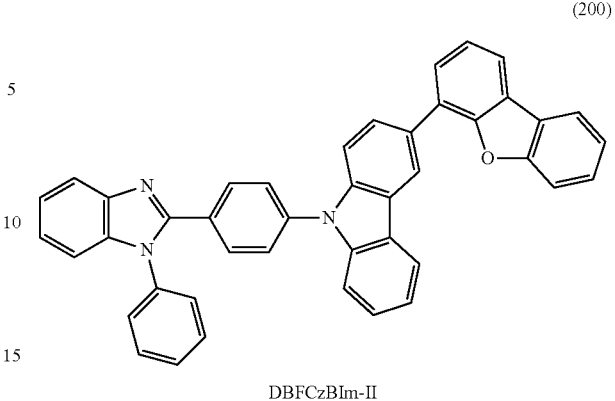

DBFCzBIm-II

[Fabrication of Light-Emitting Element 1 and Light-Emitting Element 2]

First, a glass substrate 101, over which a film of indium tin oxide containing silicon (ITSO) was fowled to a thickness of 110 nm as the first electrode 102, was prepared. A surface of the ITSO film is covered with an insulating film, and a 2 mm square portion of the surface is exposed in order that a light-emitting area be set to 2 mm×2 mm. In pretreatment for forming the light-emitting elements over the substrate, the surface of the substrate was washed with water and baked at 200° C. for one hour, and then a UV ozone treatment was performed for 370 seconds. Then, the substrate was transferred into a vacuum evaporation apparatus where the pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed to a holder provided in the vacuum evaporation apparatus such that the surface of the substrate 101 over which the ITSO film was formed faced downward.

After the pressure in the vacuum evaporation apparatus was reduced to $10^{-4}$ Pa, 4-phenyl-4'-(9-phenylfluoren-9-yl)triphenylamine (abbreviation: BPAFLP) represented by the above structural formula (i) and molybdenum (VI) oxide were co-evaporated so that the mass ratio of BPAFLP:molybdenum oxide was 2:1; thus, the hole-injection layer 111 was formed. The thickness thereof was set to 50 nm. Note that the co-evaporation is an evaporation method in which a plurality of different substances is concurrently vaporized from the respective different evaporation sources.

Next, BPAFLP was evaporated to a thickness of 10 nm, so that the hole-transport layer 112 was formed.

Further, for the light-emitting element 1, the light-emitting layer 113 was formed over the hole-transport layer 112 in such a way that DBTCzBIm-II, which is the carbazole derivative represented by the above structural formula (100) and described in Embodiment 1, 4-phenyl-4'-(9-phenyl-9H-carbazol-3-yl)triphenylamine (abbreviation: PCBA1BP) represented by the above structural formula (ii), and tris(2-phenylpyridinato-N,C²')iridium(III) (abbreviation: Ir(ppy)₃) represented by the above structural formula (iii) were evaporated to a thickness of 20 nm so that the mass ratio of DBTCzBIm-II to PCBA1BP and Ir(ppy)₃ was 1:0.25:0.06, and DBTCzBIm-II and Ir(ppy)₃ were then evaporated to a thickness of 20 nm so that the mass ratio of DBTCzBIm-II to Ir(ppy)₃ was 1:0.06. Next, DBTCzBIm-II was evaporated to a thickness of 15 nm, and then bathophenanthroline (abbreviation: BPhen) represented by the above structural formula (iv)

was evaporated to a thickness of 15 nm, so that the electron-transport layer 114 was formed.

For the light-emitting element 2, the light-emitting layer 113 was formed over the hole-transport layer 112 in such a way that DBFCzBIm-II, which is the carbazole derivative represented by the above structural formula (200) and described in Embodiment 1, PCBA1BP, and Ir(ppy)$_3$ were evaporated to a thickness of 20 nm so that the mass ratio of DBFCzBIm-II to PCBA1BP and Ir(ppy)$_3$ was 1:0.25:0.06, and DBFCzBIm-II and Ir(ppy)$_3$ were then evaporated to a thickness of 20 nm so that the mass ratio of DBFCzBIm-II to Ir(ppy)$_3$ was 1:0.06. Next, DBFCzBIm-II was evaporated to a thickness of 15 nm, and BPhen represented by the above structural formula (iv) was evaporated to a thickness of 15 nm, so that the electron-transport layer 114 was faulted.

Further, lithium fluoride was evaporated to a thickness of 1 nm over the electron-transport layer 114, so that the electron-injection layer was formed. Lastly, an aluminum film was formed to a thickness of 200 nm as the second electrode 104 functioning as a cathode. Accordingly, the light-emitting elements 1 and 2 were completed. Note that in the above evaporation processes, evaporation was all performed by a resistance heating method.

[Operation Characteristics of Light-Emitting Elements 1 and 2]

The light-emitting elements 1 and 2 thus obtained were sealed in a glove box under a nitrogen atmosphere without being exposed to the air. Then, the operation characteristics of these light-emitting elements were measured. Note that the measurements were carried out at room temperature (in an atmosphere kept at 25° C.).

Figure 14:
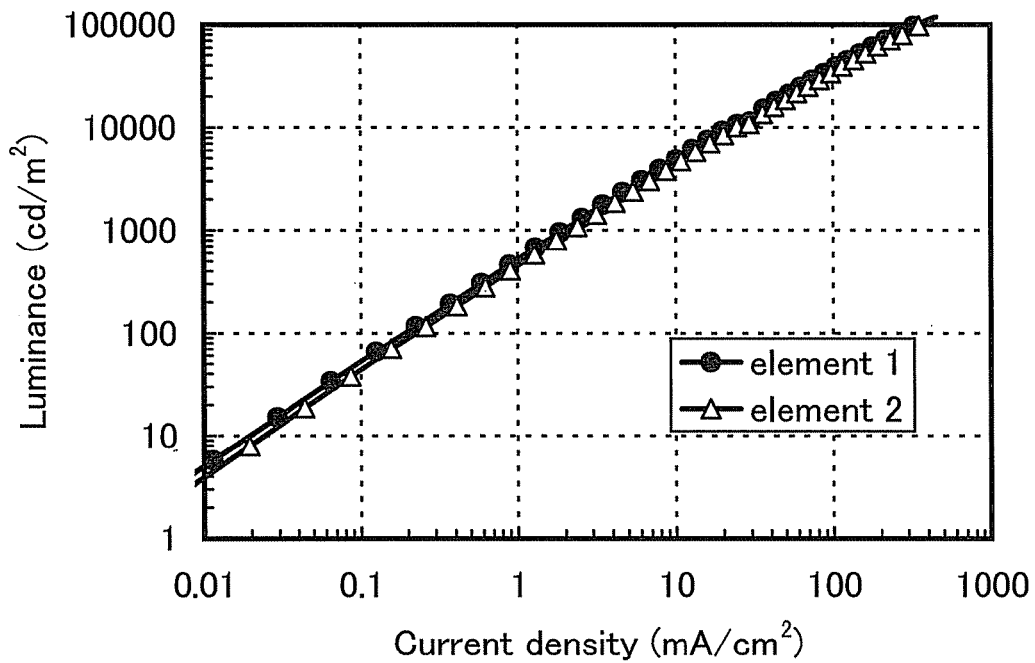
FIG. 14 shows luminance versus current density characteristics of a light-emitting element 1 and a light-emitting element 2.
Figure 15:
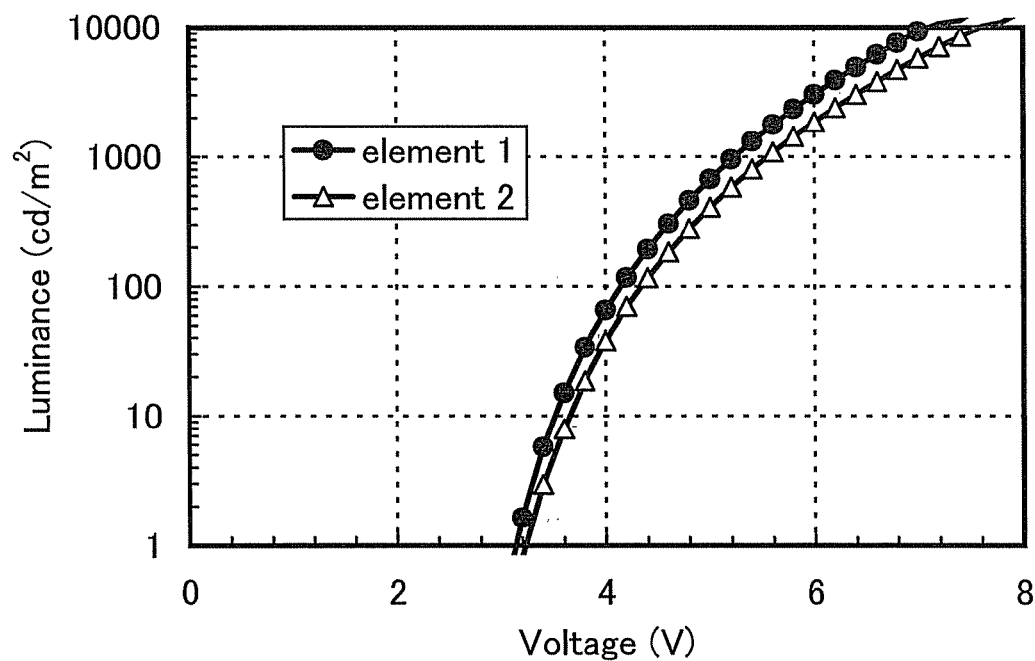
FIG. 15 shows luminance versus voltage characteristics of the light-emitting elements 1 and 2.
Figure 16:
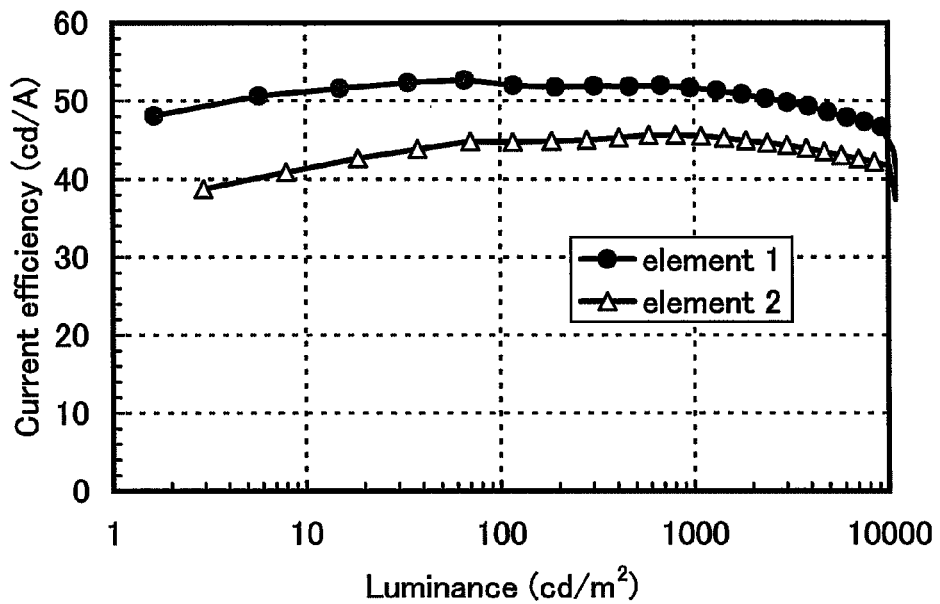
FIG. 16 shows current efficiency versus luminance characteristics of the light-emitting elements 1 and 2.

FIG. 14 shows luminance versus current density characteristics of the light-emitting elements, FIG. 15 shows luminance versus voltage characteristics thereof, and FIG. 16 shows current efficiency versus luminance characteristics thereof. In FIG. 14, the vertical axis represents luminance (cd/m$^2$), and the horizontal axis represents current density (mA/cm$^2$). In FIG. 15, the vertical axis represents luminance (cd/m$^2$), and the horizontal axis represents voltage (V). In FIG. 16, the vertical axis represents current efficiency (cd/A), and the horizontal axis represents luminance (cd/m$^2$).

FIG. 16 reveals the favorable luminance versus current efficiency characteristics of the light-emitting elements, in each of which the carbazole derivative represented by the general formula (G1) is used for the host material of the light-emitting layer for emitting green phosphorescence; thus, the elements are found to be light-emitting elements having high emission efficiency. This is because each carbazole derivative represented by the general formula (G1) has a wide band gap and high triplet excitation energy, and accordingly even a light-emitting substance that emits green phosphorescence can be effectively excited. In addition, FIG. 15 reveals the favorable luminance versus voltage characteristics of the light-emitting elements, in each of which the carbazole derivative represented by the general formula (G1) is used for the host material of the light-emitting layer for emitting green phosphorescence; thus, the elements are found to be light-emitting elements having low driving voltage. This indicates that each carbazole derivative represented by the general formula (G1) has an excellent carrier-transport property.

Figure 17:
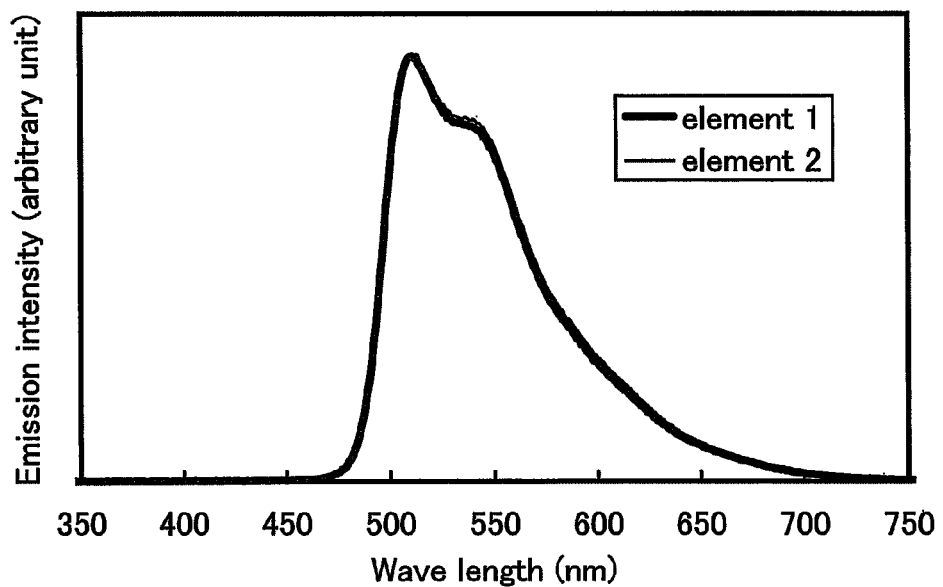
FIG. 17 shows emission spectra of the light-emitting elements 1 and 2.

FIG. 17 shows emission spectra obtained when a current of 1 mA was made to flow in the fabricated light-emitting elements 1 and 2. In FIG. 17, the vertical axis represents emission intensity (arbitrary unit), and the horizontal axis represents wavelength (nm). The emission intensity is shown as a value relative to the greatest emission intensity assumed to be 1. FIG. 17 reveals that the light-emitting elements 1 and 2 each emit green light that originates from Ir(ppy)$_3$, which was the emission center substance.

Figure 18:
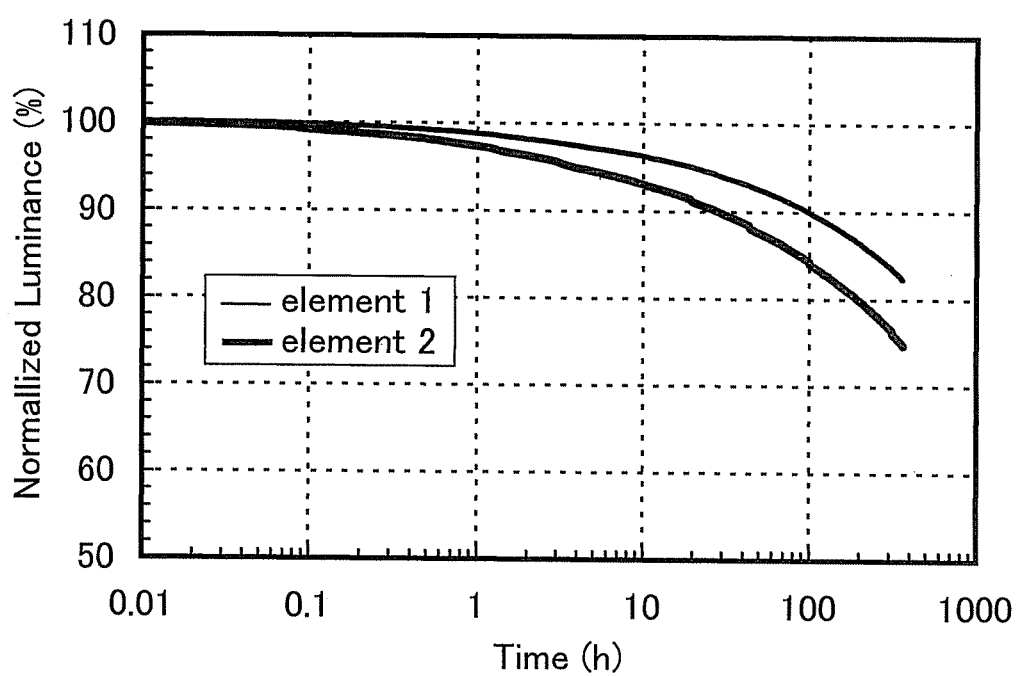
FIG. 18 shows changes in normalized luminance versus time characteristics of the light-emitting elements 1 and 2.

Next, with an initial luminance set to 1000 cd/m$^2$, these elements were driven under a condition where the current density was constant, and changes in luminance with respect to the driving time were examined. FIG. 18 shows the normalized luminance versus time characteristics. FIG. 18 reveals the favorable characteristics of the light-emitting elements 1 and 2, and thus they are found to be light-emitting elements having high reliability.

Reference Example 1

A method of synthesizing 4-phenyl-4'-(9-phenylfluoren-9-yl)triphenylamine (abbreviation: BPAFLP) (structural formula (I)) used in the above example will be specifically described. A structure of BPAFLP is illustrated below.

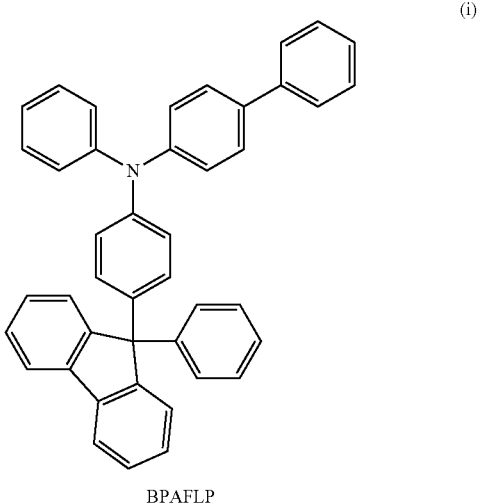 [SMILES: c1ccc(-c2ccc(N(c3ccccc3)c3ccc(C4(c5ccccc5)c5ccccc5-c5ccccc54)cc3)cc2)cc1]

BPAFLP

Step 1: Method of Synthesizing 9-(4-Bromophenyl)-9-phenylfluorene

In a 100 mL three-neck flask, 1.2 g (50 mmol) of magnesium was heated and stirred for 30 minutes under reduced pressure to be activated. This was cooled to room temperature, and the flask was made to contain a nitrogen atmosphere. Then, several drops of dibromoethane were added, so that foam formation and heat generation were confirmed. To this, 12 g (50 mmol) of 2-bromobiphenyl dissolved in 10 mL of diethyl ether was slowly added dropwise, and then the mixture was heated and stirred under reflux for 2.5 hours, so that a Grignard reagent was prepared.

Into a 500 mL three-neck flask were placed 10 g (40 mmol) of 4-bromobenzophenone and 100 mL of diethyl ether. To this mixture, the Grignard reagent which was synthesized in advance was slowly added dropwise, and then the mixture was heated and stirred under reflux for 9 hours.

After reaction, this mixture solution was filtered to give a residue. The obtained residue was dissolved in 150 mL of ethyl acetate, 1N-hydrochloric acid was added to the mixture until it was made acid, and the mixture was then stirred for 2 hours. The organic layer portion of this liquid was washed with water, and magnesium sulfate was added thereto to remove moisture. This suspension was filtered, and the obtained filtrate was concentrated to give an oily substance.

Into a 500 mL recovery flask were placed this oily substance, 50 mL of glacial acetic acid, and 1.0 mL of hydrochloric acid. The mixture was stirred and heated at 130° C. for 1.5 hours under a nitrogen atmosphere.

After the reaction, this mixture solution was filtered to give a residue. The obtained residue was washed with water, an aqueous solution of sodium hydroxide, water, and methanol in this order. Then, the mixture was dried, so that the substance which was the object of the synthesis was obtained as 11 g of a white powder in 69% yield. A reaction scheme of the above synthesis method is illustrated in the following scheme (J-1).

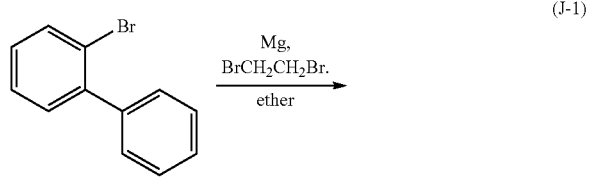

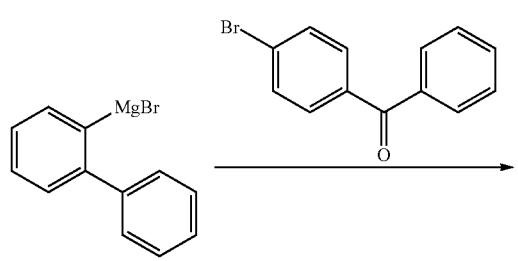

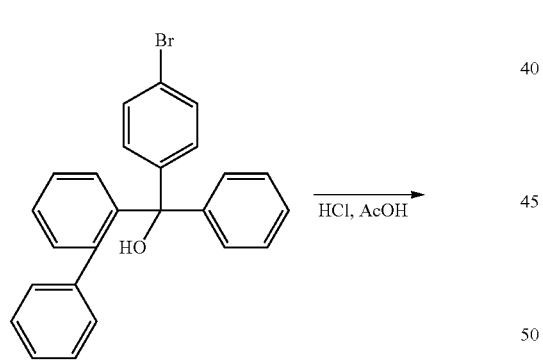

Step 2: Method of Synthesizing 4-Phenyl-4'-(9-phenylfluoren-9-yl)triphenylamine (abbreviation: BPAFLP)

Into a 100 mL three-neck flask were placed 3.2 g (8.0 mmol) of 9-(4-bromophenyl)-9-phenylfluorene, 2.0 g (8.0 mmol) of 4-phenyl-diphenylamine, 1.0 g (10 mmol) of sodium tert-butoxide, and 23 mg (0.04 mmol) of bis(dibenzylideneacetone)palladium(0), and the air in the flask was replaced with nitrogen. Then, 20 mL of dehydrated xylene was added to this mixture. After the mixture was degassed by being stirred under reduced pressure, 0.2 mL (0.1 mmol) of tri(tert-butyl)phosphine (a 10 wt % hexane solution) was added to the mixture. This mixture was stirred and heated at 110° C. for 2 hours under a nitrogen atmosphere.

After the reaction, 200 mL of toluene was added to this mixture, and this suspension was filtered through Florisil (produced by Wako Pure Chemical Industries, Ltd., Catalog No. 540-00135), Celite (produced by Wako Pure Chemical Industries, Ltd., Catalog No. 531-16855), and alumina. The obtained filtrate was concentrated, and the resulting substance was purified by silica gel column chromatography (a developing solvent in which the ratio of toluene to hexane was 1:4). The obtained fraction was concentrated, and acetone and methanol were added to the mixture. The mixture was irradiated with ultrasonic waves and then recrystallized, so that the substance which was the object of the synthesis was obtained as 4.1 g of a white powder in 92% yield. A reaction scheme of the above synthesis method is illustrated in the following scheme (J-2).

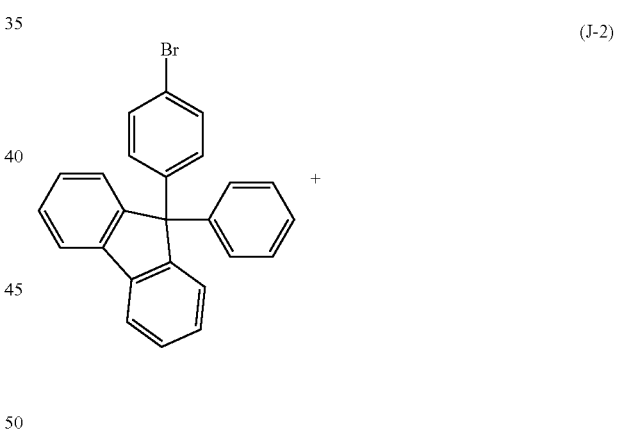

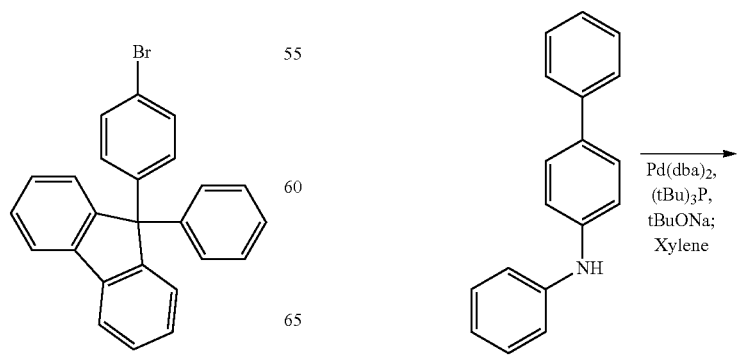

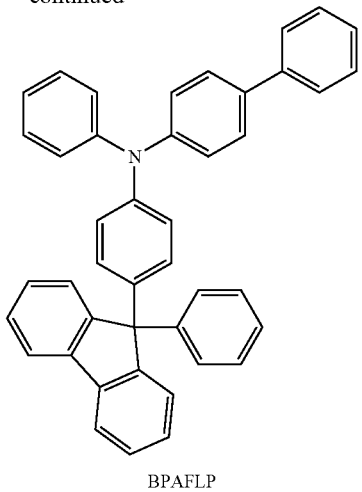

BPAFLP

The Rf values of the substance that was the object of the synthesis, 9-(4-bromophenyl)-9-phenylfluorene, and 4-phenyl-diphenylamine were respectively 0.41, 0.51, and 0.27, which were found by silica gel thin layer chromatography (TLC) (a developing solvent in which the ratio of ethyl acetate to hexane was 1:10).

The compound obtained in Step 2 above was subjected to nuclear magnetic resonance (NMR) spectroscopy. The measurement data are shown below. The measurement results indicate that the obtained compound was BPAFLP, which is a fluorene derivative.

$^1$H NMR (CDCl$_3$, 300 MHz): δ (ppm)=6.63-7.02 (m, 3H), 7.06-7.11 (m, 6H), 7.19-7.45 (m, 18H), 7.53-7.55 (m, 2H), 7.75 (d, J=6.9, 2H).

This application is based on Japanese Patent Application serial no. 2010-267060 filed with the Japan Patent Office on Nov. 30, 2010, the entire contents of which are hereby incorporated by reference.

What is claimed is:

1. A carbazole compound represented by a general formula (G1):

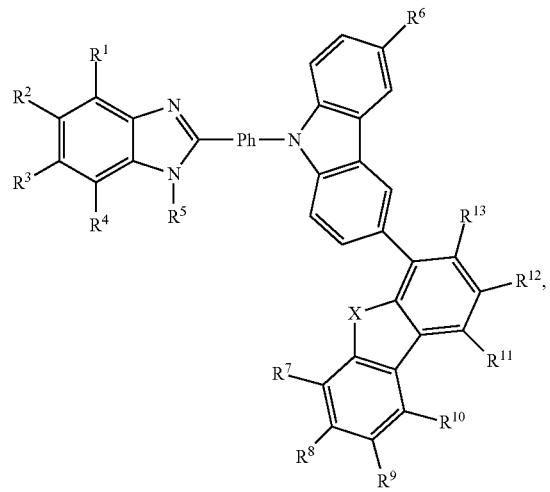

(G1)

wherein:

R$^1$ to R$^4$ separately represent any one of hydrogen, an alkyl group having 1 to 4 carbon atoms, a phenyl group, and a tolyl group;

R$^5$ represents an aryl group having 6 to 12 carbon atoms;

R$^6$ to R$^{13}$ separately represent any one of hydrogen, an alkyl group having 1 to 4 carbon atoms, and an aryl group having 6 to 12 carbon atoms;

Ph represents a substituted or unsubstituted phenylene group; and

X represents a sulfur atom or an oxygen atom.

2. The carbazole compound according to claim 1, wherein a substituent of the substituted phenylene group is an alkyl group having 1 to 4 carbon atoms.

3. The carbazole compound according to claim 1, wherein R$^6$ to R$^{13}$ separately represent any one of a phenyl group, a naphthyl group, a biphenyl group, and a tolyl group.

4. The carbazole compound according to claim 1, wherein R$^5$ represents any one of a phenyl group, a naphthyl group, a biphenyl group, and a tolyl group.

5. The carbazole compound according to claim 1, wherein the carbazole compound is represented by a general formula (G2):

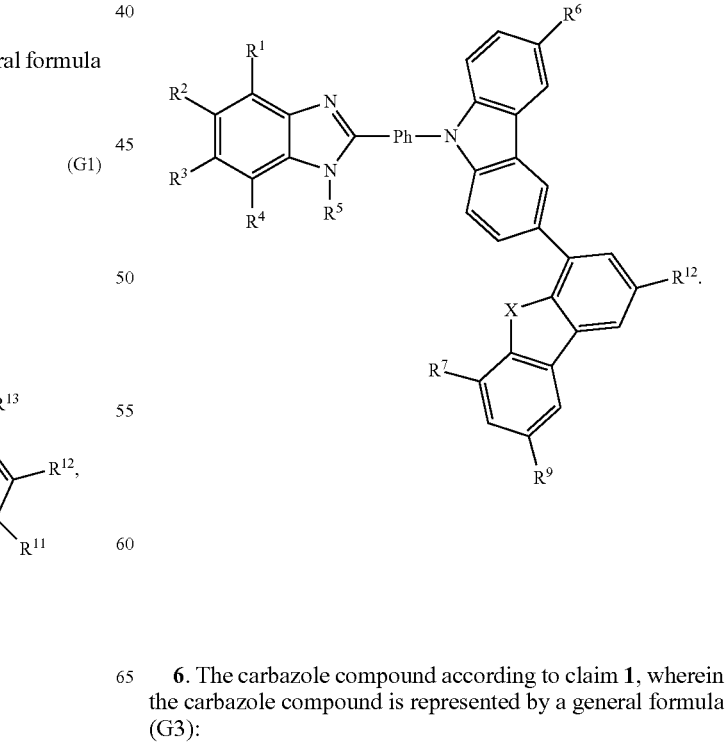

(G2)

6. The carbazole compound according to claim 1, wherein the carbazole compound is represented by a general formula (G3):

(G3)

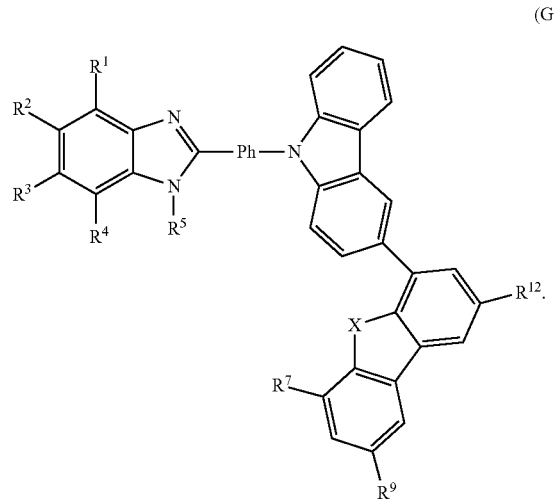

7. The carbazole compound according to claim 1, wherein the carbazole compound is represented by a general formula (G4):

(G5)

9. The carbazole compound according to claim 1, wherein the carbazole compound is represented by a general formula (G6):

(G4)

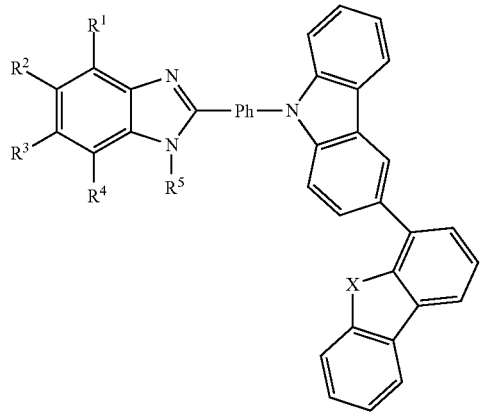

8. The carbazole compound according to claim 1, wherein the carbazole compound is represented by a general formula (G5):

(G6)

10. The carbazole compound according to claim 1, wherein the carbazole compound is represented by a general formula (G7):

(G7)

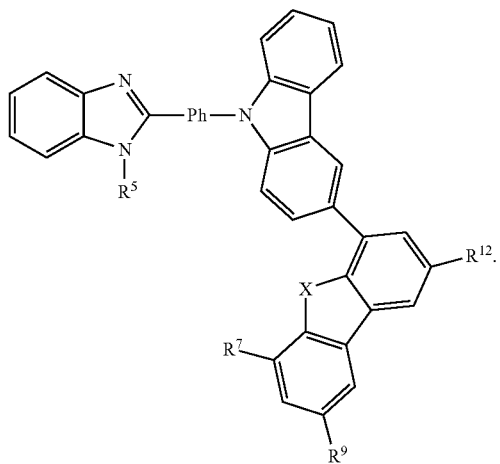

11. The carbazole compound according to claim 1, wherein the carbazole compound is represented by a general formula (G8):

(G8)

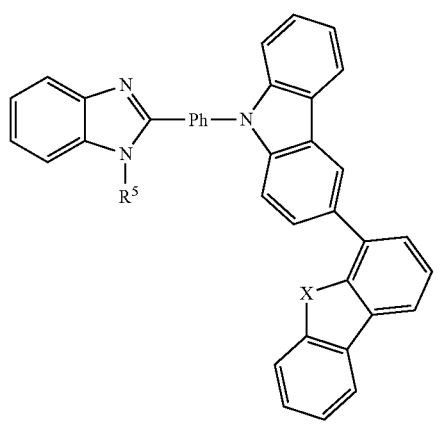

12. The carbazole compound according to claim 1, wherein the carbazole compound is represented by a general formula (G9):

(G9)

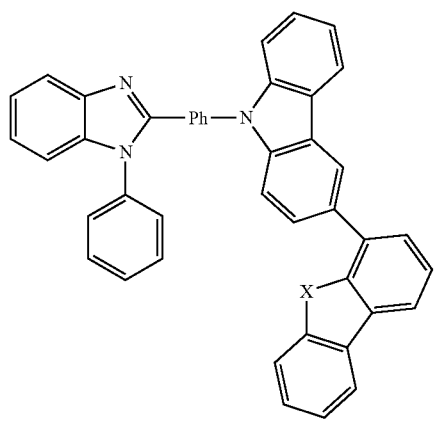

13. The carbazole compound according to claim 1, wherein the carbazole compound is represented by a general formula (G10):

(G10)

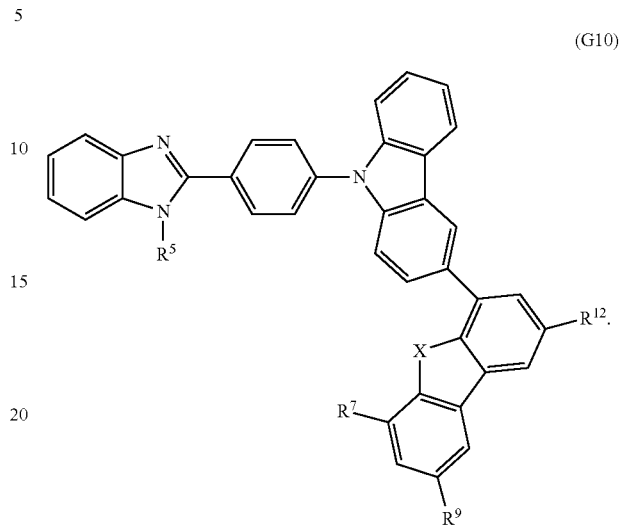

14. The carbazole compound according to claim 1, wherein the carbazole compound is represented by a general formula (G11):

(G11)

15. An organic semiconductor material comprising the carbazole compound according to claim 1.

16. A light-emitting element material comprising the carbazole compound according to claim 1.

17. A light-emitting element comprising:
a pair of electrodes; and
a layer containing the carbazole compound according to claim 1 between the pair of electrodes.

18. A light-emitting device comprising the light-emitting element according to claim 17.

19. An electronic device comprising the light-emitting device according to claim 18.

20. A lighting device comprising the light-emitting device according to claim 18.

* * * * *

UNITED STATES PATENT AND TRADEMARK OFFICE
CERTIFICATE OF CORRECTION

PATENT NO. : 8,697,885 B2  
APPLICATION NO. : 13/305081  
DATED : April 15, 2014  
INVENTOR(S) : Sachiko Kawakami et al.

Page 1 of 1

It is certified that error appears in the above-identified patent and that said Letters Patent is hereby corrected as shown below:

In the Specification:

Column 1, Line 48; Change "light-emitting, element," to --light-emitting element,--.

Column 58, Line 54; Change "quality; and" to --quality, and--.

Column 62, Line 47; Change "foamed" to --formed--.

Column 66, Line 5; Change "(2-thenyl)" to --(2-thenoyl)--.

Column 66, Line 62; Change "spino" to --spiro--.

Column 68, Line 62; Change "found" to --formed--.

Column 90, Line 22; Change "fowled" to --formed--.

Column 91, Line 15; Change "faulted." to --formed.--.

Column 92, Lines 15 to 16; Change "(structural formula(I))" to --(structural formula(i))--.

Signed and Sealed this  
Twenty-third Day of September, 2014

Michelle K. Lee  
*Deputy Director of the United States Patent and Trademark Office*